(12) United States Patent
Wilding et al.

(10) Patent No.: US 11,608,343 B2
(45) Date of Patent: Mar. 21, 2023

(54) SUBSTITUTED PYRIMIDO[5,4-D]PYRIMIDINES AS HER2 INHIBITORS

(71) Applicant: Boehringer Ingelheim International GmbH, Ingelheim am Rhein (DE)

(72) Inventors: Birgit Wilding, Vienna (AT); Dietrich Boese, Erzhausen (DE); Harald Engelhardt, Ebreichsdorf (AT); Julian Fuchs, Vienna (AT); Ralph Neumueller, Moedling (AT); Mark Petronczki, Vienna (AT); Dirk Scharn, Vienna (AT); Matthias Treu, Vienna (AT)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 106 days.

(21) Appl. No.: 17/223,132

(22) Filed: Apr. 6, 2021

(65) Prior Publication Data
US 2021/0332054 A1    Oct. 28, 2021

(30) Foreign Application Priority Data
Apr. 24, 2020   (EP) .................................... 20171221

(51) Int. Cl.
| A61K 31/519 | (2006.01) |
| C07D 487/04 | (2006.01) |
| A61K 47/26 | (2006.01) |
| A61K 47/32 | (2006.01) |
| A61K 47/36 | (2006.01) |
| C07D 519/00 | (2006.01) |

(52) U.S. Cl.
CPC ............ *C07D 487/04* (2013.01); *A61K 47/26* (2013.01); *A61K 47/32* (2013.01); *A61K 47/36* (2013.01); *C07D 519/00* (2013.01)

(58) Field of Classification Search
CPC ............................ A61K 31/519; C07D 487/04
USPC ........................................ 514/262.1; 544/256
See application file for complete search history.

(56) References Cited

FOREIGN PATENT DOCUMENTS

| WO | 1997032880 A1 | 9/1997 |
| WO | 2003049740 A1 | 6/2003 |
| WO | 2005044302 A1 | 5/2005 |
| WO | 2007059257 A2 | 5/2007 |
| WO | 2015175632 A1 | 11/2015 |
| WO | 2015195228 A1 | 12/2015 |
| WO | 2016183278 A1 | 11/2016 |
| WO | 2019042409 A1 | 3/2019 |
| WO | 2019046775 A1 | 3/2019 |
| WO | 2021156178 A1 | 8/2021 |
| WO | 2021156180 A1 | 8/2021 |
| WO | 2021213800 A1 | 10/2021 |

OTHER PUBLICATIONS

Arteaga et al., "ERBB Receptors: From Oncogene Discovery to Basic Science to Mechanism-Based Cancer Therapeutics", Cancer Cell, 2014, vol. 25, No. 3, pp. 282-303.
Balent et al., "Metabolic Considerations in Prodrug Design", Burger's Medicinal Chemistry and Drug Discovery, 1995, vol. 1, pp. 948-982.
Burger's Medicinal Chemistry and Drug Discovery, 5th Ed. M. Wolff (ed), John Wiley & Sons, 1995, vol. 1, pp. 172-178.
Burger's Medicinal Chemistry and Drug Discovery, 5th Ed. M. Wolff (ed), John Wiley & Sons, 1995, vol. 1, pp. 949-982.
Citri et al., "EGF-ERBB signalling: towards the systems level", Nature Reviews Molecular Cell Biology, 2006, vol. 7, No. 7, pp. 505-516.
Connell et al., "Activating HER2 mutations as emerging targets in multiple solid cancers", ESMO Open, 2017, vol. 2, No. 5, pp. e000279.
Del Bello et al., "Identification of 2-aminopyrimidine derivatives as inhibitors of the canonical Wnt signaling pathway", Bioorganic & Medicinal Chemistry, 2015, vol. 23, No. 17, pp. 5725-5733.
Hynes et al., "ErbB receptors and signaling pathways in cancer", Current Opinion in Cell Biology, 2009, vol. 21, No. 2, pp. 177-184.
International Search Report and Written Opinion for application PCT/EP2021/059015, dated Apr. 23, 2021.
Ishikawa et al., "Design and Synthesis of Novel Human Epidermal Growth Factor Receptor 2 (HER2)/Epidermal Growth Factor Receptor (EGFR) Dual Inhibitors Bearing a Pyrrolo[3,2-d]pyrimidine Scaffold", Journal of Medicinal Chemistry, 2011, vol. 54, No. 23, pp. 8030-8050.
McDaniel et al., "Discovery of N (4-(2,4-Difluorophenoxy)-3-(6-methyl-7-oxo-6,7-dihydro 1H pyrrolo[2,3 c]pyridin-4-yl) phenyl)ethanesulfonamide (ABBV-075/Mivebresib), a Potent and Orally Available Bromodomain and Extraterminal Domain (BET) Family Bromodomain Inhibitor", Journal of Medicinal Chemistry, 2017, vol. 60, No. 20, pp. 3369-8384.
Notari, "Theory and Practice of Prodrug Kinetics", Prodrug Kinetics, 1985, vol. 112, pp. 309-396.

(Continued)

*Primary Examiner* — Douglas M Willis
(74) *Attorney, Agent, or Firm* — Mary Breen Smith

(57) ABSTRACT

The present invention relates to new [1,3]diazino[5,4-d]pyrimidines and derivatives of Formula (I)

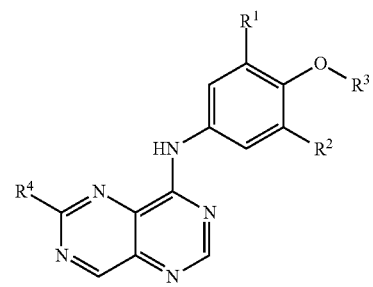

wherein the groups $R^1$, $R^2$, $R^3$ and $R^4$ have the meanings given in the claims and specification, their use as inhibitors of HER2 and its mutants, pharmaceutical compositions which contain such compounds and their use as medicaments, especially as agents for treatment and/or prevention of oncological diseases.

34 Claims, No Drawings

(56) References Cited

OTHER PUBLICATIONS

Perera et al., "HER2YVMA drives rapid development of adenosquamous lung tumors in mice that are sensitive to BIBW2992 and rapamycin combination therapy", PNAS, 2009, vol. 106, pp. 474-479.

Stephens et al., "Intragenic ERBB2 kinase mutations in tumours", NATURE, 2004, vol. 431, No. 7008, pp. 525-526.

Testa, "Drug Metabolism", Burger's Medicinal Chemistry and Drug Discovery, 1995, vol. 1, pp. 129-178.

Wan et al., "An Efficient Direct Amination of Cyclic Amides and Cyclic Ureas†", Organic Letters, 2006, vol. 8, No. 11, pp. 2425-2428.

Wang et al., "Facile and efficient synthesis and biological evaluation of 4-anilinoquinazoline derivatives as EGFR inhibitors", Bioorganic & Medicinal Chemistry Letters, 2016, vol. 26, No. 11, pp. 2589-2593.

Wang et al., "HER2 kinase domain mutation results in constitutive phosphorylation and activation of HER2 and EGFR and resistance to EGFR tyrosine kinase inhibitors", Cancer Cell, 2006, vol. 10, No. 1, pp. 25-38.

Wang, "ErbB Receptor Signaling, Methodsand Protocols", Methods in Molecular Biology, 2017, vol. 1652, pp. 3-35.

Zhang et al., "Enrichment of novel quinazoline derivatives with high antitumor activity in mitochondria tracked by its self-fluorescence", European Journal of Medicinal Chemistry, 2019, vol. 178, pp. 417-432.

SUBSTITUTED PYRIMIDO[5,4-D]PYRIMIDINES AS HER2 INHIBITORS

BACKGROUND OF THE INVENTION

Field of the Invention

The present invention relates to new [1,3]diazino[5,4-d]pyrimidines and derivatives of Formula (I)

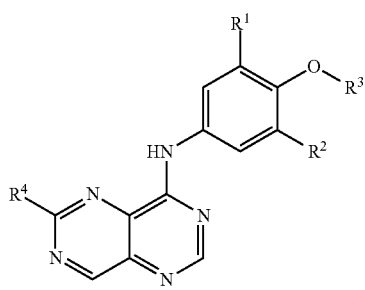

wherein the groups $R^1$, $R^2$, $R^3$ and $R^4$ have the meanings given in the claims and specification, their use as inhibitors of HER2 and its mutants, pharmaceutical compositions which contain such compounds and their use as medicaments, especially as agents for treatment and/or prevention of oncological diseases.

The family of ERBB transmembrane receptor tyrosine kinases (RTKs) consists of the four members EGFR (ERBB1), HER2 (Neu, ERBB2), HER3 (ERBB3) and HER4 (ERBB4), which fulfill essential functions during development (Citri et al., Nat. Rev. Mol. Cell Biol., 2006, 7(7), 505-516; Hynes et al., Curr. Opin. Cell Biol., 2009, 21(2), 177-184; Wang, Z., Methods Mol. Biol., 2017, 1652, 3-35). ERBB signaling is initiated upon binding of the extracellular domains of EGFR, HER3 or HER4 to their respective ligands and subsequent homo- or heterodimerization of ERBB family members. HER2, for which no ligand has been identified, is the preferred dimerization partner for the other ERBB members. Once an active ligand-receptor complex has been formed, the intracellular tyrosine kinase domains of EGFR, HER2, HER3 or HER4 are activated by auto- or transphosphorylation and subsequently elicit a signal transduction cascade most notably engaging the mitogen-activated protein (MAP) kinase and/or the phosphoinositide 3-kinase (PI3K) pathways (Citri et al., Nat. Rev. Mol. Cell. Biol., 2006, 7(7), 505-516; Hynes et al., Curr. Opin. Cell Biol., 2009, 21(2), 177-184; Wang, Z., Methods Mol. Biol., 2017, 1652, 3-35).

Aberrant ERBB signaling is implicated in several pathophysiological conditions including cancer or neurological diseases. In cancer, ERBB signaling is hyper-activated through mutations that render the RTK constitutively active by promoting dimerization or shifting the equilibrium towards the active conformer of the kinase and/or through amplification and consequent over-expression of the RTK. Both oncogenic mechanisms increase the net output of ERBB signaling and thereby promote cell survival, cell growth and proliferation (Arteaga et al., Cancer Cell, 2014, 25(3), 282-303).

Aberrant HER2 signaling is observed in a wide variety of human malignancies. Oncogenic mutations are described for the extracellular, (juxta-) membrane and intracellular regions of the protein. Collectively these mutations render HER2 constitutively active, fueling cancer initiation, tumor maintenance and growth (Connell et al., ESMO Open, 2017, 2(5), e000279). Similarly, HER2 overexpression increases HER2 signaling and underlies neoplastic transformation and tumor maintenance in a variety of indications including breast, gastric or lung cancer.

Consequently, interference with HER2 oncogenic signaling results in inhibition of tumor growth. Targeted therapies include HER2 directed antibodies (including trastuzumab and pertuzumab), HER2 directed antibody-drug conjugates (trastuzumab-DM1 (T-DM1, ado-trastuzumab emtansine)) and small molecules inhibiting the HER2 kinase domain (afatinib, neratinib, lapatinib).

Altogether, tumors driven by HER2 oncogenic mutations or HER2 wild type over-expression (for example due to gene amplification) might benefit from a HER2 specific tyrosine kinase inhibitor (TKI). Collectively, HER2 alterations affect up to 6-7% of all human cancers and an EGFR wild type sparing TKI (tyrosine kinase inhibitor) could emerge as an effective therapeutic option.

Even though there are HER2 wild type inhibitors that are selective over EGFR wild type, such as tucatinib, these inhibitors do not have efficacy on HER2 carrying exon 20 mutations. Other selective wild type HER2 inhibitors have been disclosed in prior art documents WO 2003/049740, WO 2007/059257, WO 2005/044302.

HER2 exon 20 mutations constitute a subset of HER2 gain-of-function mutations that result in enhanced kinase activity (Wang et al. Cancer Cell, 2006, 10(1), 25-38). This enhanced HER2 kinase activity feeds into downstream signaling cascades that stimulate neoplastic transformation through promoting growth, proliferation and survival of the mutant cells.

Studies in genetically engineered mouse models have demonstrated that the most prevalent HER2 exon 20 mutation in NSCLC, the duplication of the 4 amino acids YVMA (p.A775_G776insYVMA), is required and sufficient to drive oncogenic growth (Perera et al., Proc. Natl. Acad. Sci. USA, 2009, 106(2), 474-479). Withdrawal of HER2-YVMA expression is associated with tumor shrinkage, suggesting that this oncogenic variant of HER2 is required for tumor maintenance (Perera et al. 2009). In addition, this study demonstrated that in a mouse model, the pan-ERBB blocker Afatinib is efficacious in vivo and can interfere with oncogenic signaling of HER2-YVMA (Perera et al. 2009).

Oncogenic mutations in HER2 in NSCLC predominantly affect the tyrosine kinase domain of HER2 and cluster in exon 20 of the ERBB2 gene (Stephens et al., Nature, 2004, 431(7008), 525-526). 2-4% of lung cancer patients are estimated to carry activating mutations in HER2 exon 20. Clinically approved ERBB targeting tyrosine kinase inhibitors are not efficacious in these patients, as they are limited by EGFR wild type-mediated dose limiting toxicity. Afatinib and other pan-ERBB blockers have shown limited efficacy in HER2 exon 20 mutated NSCLC patients, mainly due to limitations in reaching an efficacious dose. In particular, EGFR wild type mediated toxicity limits efficacious dosing.

Allitinib, ibrutinib, neratinib, poziotinib and pyrotinib are known pan-ERBB inhibitors of mutant HER2 exon 20. Further inhibitors of mutant HER2 exon 20 have been disclosed in prior art documents WO 2015/175632, WO 2015/195228, WO 2016/183278 and WO 2019/046775.

There is a high unmet medical need for compounds that selectively target HER2 exon 20 mutant proteins while sparing EGFR wild type to overcome the disadvantages of EGFR wild type mediated dose limiting toxicity.

It has been found that the compounds of the present invention bind to the tyrosine kinase domain of wild type and mutant HER2 exon 20 in an orthosteric and covalent manner while sparing EGFR wild type and act as selective inhibitors of wild type HER2 and mutant HER2 carrying mutations in exon 20.

SUMMARY OF THE INVENTION

The aim of the present invention is to provide new inhibitors of mutant HER2 exon 20 that are selective over EGFR wild type. The compounds of the invention act as selective inhibitors of HER2 exon 20 and show an improved wild type EGFR sparing efficacy profile in addition to high selectivity over EGFR wild type compared to prior art compounds. Furthermore, some compounds of the present invention show an improved pharmacokinetic and pharmacological profile, such as good metabolic stability.

The compounds of the invention are useful for the prevention and/or treatment of a disease and/or condition characterised by excessive or abnormal cell proliferation, especially in the treatment and/or prevention of cancer.

DETAILED DESCRIPTION OF THE INVENTION

The present invention relates to new [1,3]diazino[5,4-d] pyrimidines and derivatives of Formula (I)

(I)

wherein
$R^1$ is selected from the group consisting of hydrogen, —$CH_3$, —CCH, —$OCH_3$ and halogen;
$R^2$ is hydrogen or halogen;
$R^3$ is selected from the group consisting of formula (i.1), (i.2), (i.3) and (i.4);

(i.1)

(i.2)

(i.3)

(i.4)

$R^4$ is selected from the group consisting of $R^{4.a}$ a and $R^{4.b}$ $R^{4.a}$ $R^{4.b}$ wherein
Q denotes 4-6 membered heterocyclyl containing 1 N-atom, wherein one carbon atom of the ring is optionally substituted by methyl;
Z denotes 4-6 membered heterocyclyl containing 1 N-atom, wherein one carbon atom of the ring is optionally substituted by methyl;
$R^5$ is H or $CH_3$;
and at least one of $R^1$ and $R^2$ is not hydrogen.

PREFERRED EMBODIMENTS

In another embodiment of the present invention $R^1$ is selected from the group consisting of —$CH_3$, —CCH, —$OCH_3$ and halogen.

In another embodiment of the present invention $R^1$ is selected from the group consisting of —$CH_3$, —CCH, —$OCH_3$, chlorine and fluorine.

In another embodiment of the present invention $R^1$ is —$CH_3$.

In another embodiment of the present invention $R^1$ is —CCH.

In another embodiment of the present invention $R^1$ is —$OCH_3$.

In another embodiment of the present invention $R^1$ is chlorine.

In another embodiment of the present invention $R^1$ is fluorine.

In another embodiment of the present invention $R^1$ is hydrogen.

In another embodiment of the present invention $R^2$ is selected from the group consisting of hydrogen fluorine and chlorine.

In another embodiment of the present invention $R^2$ is hydrogen.

In another embodiment of the present invention $R^2$ is halogen.

In another embodiment of the present invention $R^2$ is fluorine or chlorine.

In another embodiment of the present invention $R^2$ is fluorine.

In another embodiment of the present invention $R^2$ is chlorine.

In another embodiment of the present invention $R^3$ is selected from the group consisting of formula (i.1), (i.2), (i.3) and (i.4).

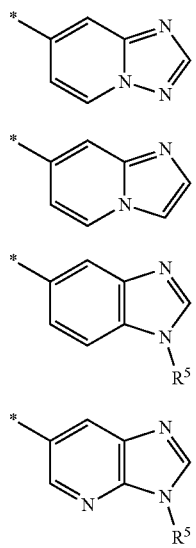

(i.1)

(i.2)

(i.3)

(i.4)

In another embodiment of the present invention $R^3$ is a group consisting of formula (i.1) or (i.3).
In another embodiment of the present invention $R^3$ is a group consisting of formula (i.2) or (i.4).
In another embodiment of the present invention $R^3$ is a group consisting of formula (i.1) or (i.2).
In another embodiment of the present invention $R^3$ is a group consisting of formula (i.1) or (i.4).
In another embodiment of the present invention $R^3$ is a group consisting of formula (i.2) or (i.3).
In another embodiment of the present invention $R^3$ is a group consisting of formula (i.3) or (i.4).
In another embodiment of the present invention $R^3$ is a group of formula (i.1).
In another embodiment of the present invention $R^3$ is a group of formula (i.2).
In another embodiment of the present invention $R^3$ is a group of formula (i.3).
In another embodiment of the present invention $R^3$ is a group of formula (i.4).
In another embodiment of the present invention $R^4$ is $R^{4.a}$, wherein $R^{4.a}$ is

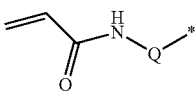

$R^{4.a}$

In another embodiment of the present invention $R^{4.a}$ is $R^{4.a.1}$ wherein $R^{4.a.1}$ is

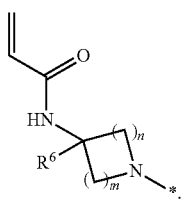

$R^{4.a.1}$

In another embodiment of the present invention $R^4$ is $R^{4.b}$, wherein $R^{4.b}$ is

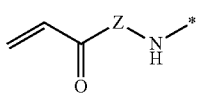

$R^{4.b}$

In another embodiment of the present invention $R^{4.b}$ is $R^{4.b.1}$ wherein $R^{4.b.1}$ is

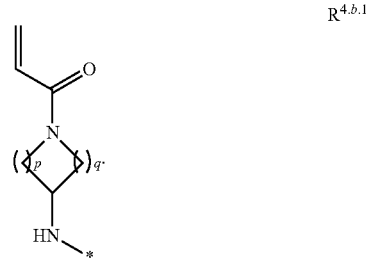

$R^{4.b.1}$

In another embodiment of the present invention $R^5$ is H.
In another embodiment of the present invention $R^5$ is $CH_3$.
In another embodiment of the present invention $R^6$ is H.
In another embodiment of the present invention $R^6$ is $CH_3$.
In another embodiment of the present invention m is 1.
In another embodiment of the present invention m is 2.
In another embodiment of the present invention n is 1
In another embodiment of the present invention n is 2.
In another embodiment of the present invention p is 1.
In another embodiment of the present invention p is 2.
In another embodiment of the present invention q is 1.
In another embodiment of the present invention q is 2.
In another embodiment of the present invention Q denotes 4-6 membered saturated heterocyclyl containing 1 N-atom, wherein one carbon atom of the ring is optionally substituted by methyl.
In another embodiment of the present invention Q denotes 4-6 membered partially unsaturated heterocyclyl containing 1 N-atom, wherein one carbon atom of the ring is optionally substituted by methyl.
In another embodiment of the present invention Q denotes azetidinyl.
In another embodiment of the present invention Q denotes pyrrolidinyl.
In another embodiment of the present invention Q denotes piperidinyl.
In another embodiment of the present invention Q denotes azetidinyl, wherein one carbon atom of the ring is substituted by methyl.
In another embodiment of the present invention Q denotes pyrrolidinyl, wherein one carbon atom of the ring is substituted by methyl.
In another embodiment of the present invention Q denotes piperidinyl, wherein one carbon atom of the ring is substituted by methyl.
In another embodiment of the present invention Z denotes 4-6 membered saturated heterocyclyl containing 1 N-atom, wherein one carbon atom of the ring is optionally substituted by methyl.

In another embodiment of the present invention Z denotes 4-6 membered partially unsaturated heterocyclyl containing 1 N-atom, wherein one carbon atom of the ring is optionally substituted by methyl.

In another embodiment of the present invention Z denotes azetidinyl.

In another embodiment of the present invention Z denotes pyrrolidinyl.

In another embodiment of the present invention Z denotes piperidinyl.

In another embodiment of the present invention Z denotes azetidinyl, wherein one carbon atom of the ring is substituted by methyl.

In another embodiment of the present invention Z denotes pyrrolidinyl, wherein one carbon atom of the ring is substituted by methyl.

In another embodiment of the present invention Z denotes piperidinyl, wherein one carbon atom of the ring is substituted by methyl.

In another embodiment of the present invention Q and Z denote 4-6 membered saturated heterocyclyl containing 1 N-atom, wherein one carbon atom of the ring is optionally substituted by methyl.

In another embodiment of the present invention Q and Z denote 4-6 membered partially unsaturated heterocyclyl containing 1 N-atom, wherein one carbon atom of the ring is optionally substituted by methyl.

Any and each of the definitions of $R^1$, $R^2$, $R^3$, $R^4$, $R^{4.a}$, $R^{4.a.1}$, $R^{4.b}$, $R^{4.b.1}$, $R^5$, $R^6$, m, n, p, q, Q and Z may be combined with each other.

A preferred embodiment of the current invention are the above compounds of Formula (I), selected from the group consisting of examples I-01 to I-19.

| Example | Structure |
|---------|-----------|
| I-01 | 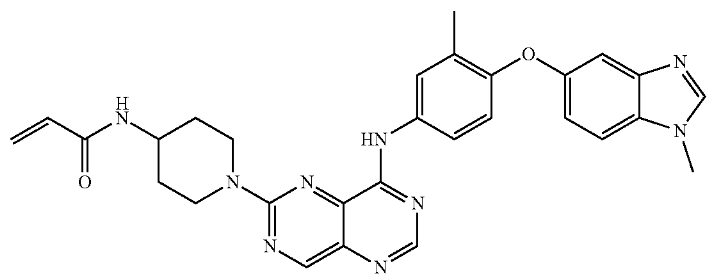 [SMILES: C=CC(=O)NC1CCN(c2ncc3ncnc(Nc4ccc(Oc5ccc6c(c5)ncn6C)c(C)c4)c3n2)CC1] |
| I-02 | 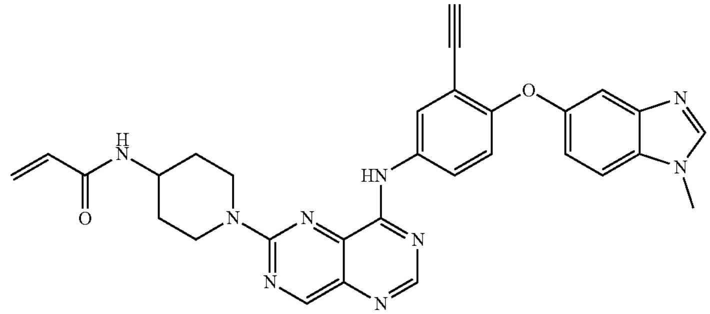 [SMILES: C#Cc1cc(Nc2ncnc3cnc(N4CCC(NC(=O)C=C)CC4)nc23)ccc1Oc1ccc2c(c1)ncn2C] |
| I-03 | 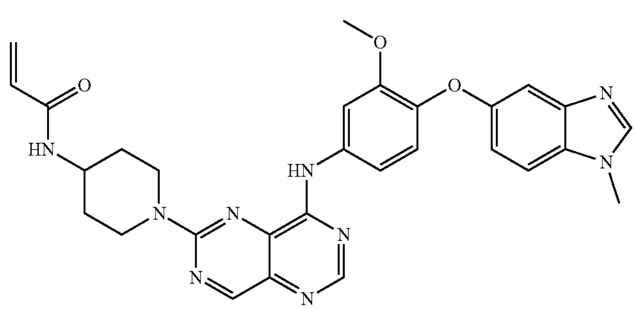 [SMILES: C=CC(=O)NC1CCN(c2ncc3ncnc(Nc4ccc(Oc5ccc6c(c5)ncn6C)c(OC)c4)c3n2)CC1] |

-continued
| Example | Structure |
|---|---|
| I-04 | 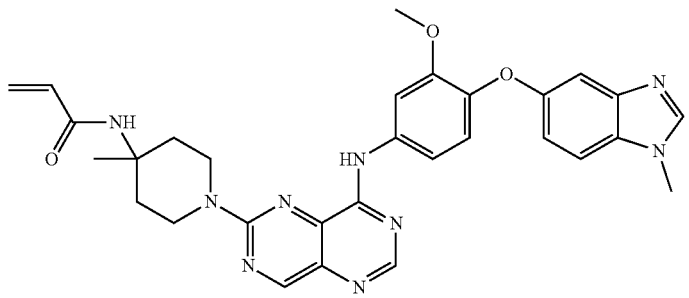 [SMILES: C=CC(=O)NC1(C)CCN(c2ncc3ncnc(Nc4ccc(Oc5ccc6c(c5)ncn6C)c(OC)c4)c3n2)CC1] |
| I-05 | 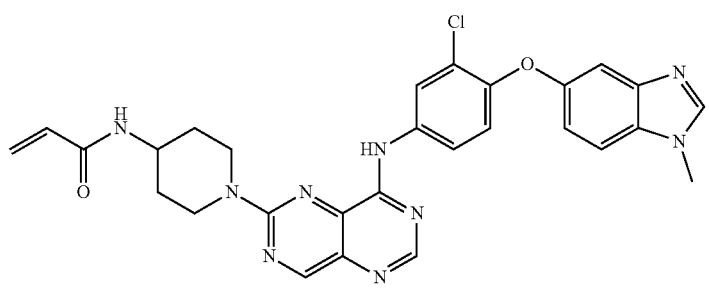 [SMILES: C=CC(=O)NC1CCN(c2ncc3ncnc(Nc4ccc(Oc5ccc6c(c5)ncn6C)c(Cl)c4)c3n2)CC1] |
| I-06 | 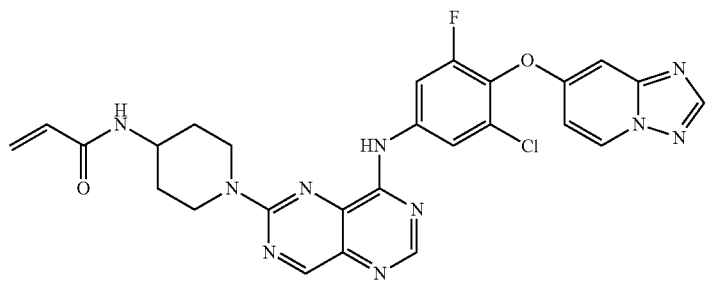 [SMILES: C=CC(=O)NC1CCN(c2ncc3ncnc(Nc4cc(F)c(Oc5ccn6ncnc6c5)c(Cl)c4)c3n2)CC1] |
| I-07 | 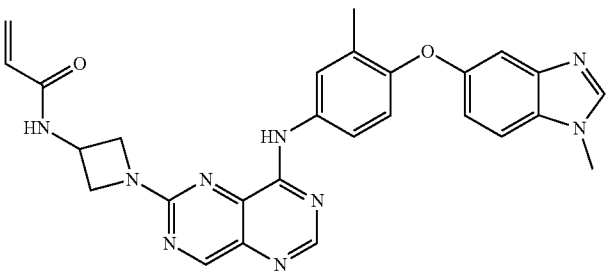 [SMILES: C=CC(=O)NC1CN(c2ncc3ncnc(Nc4ccc(Oc5ccc6c(c5)ncn6C)c(C)c4)c3n2)C1] |
| I-08 | 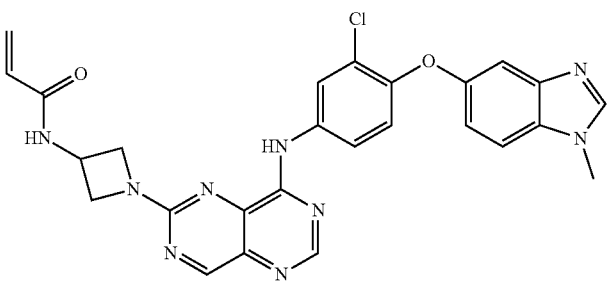 [SMILES: C=CC(=O)NC1CN(c2ncc3ncnc(Nc4ccc(Oc5ccc6c(c5)ncn6C)c(Cl)c4)c3n2)C1] |

| Example | Structure |
|---|---|
| I-09 | 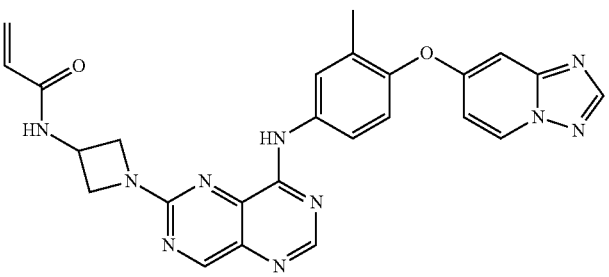 [SMILES: C=CC(=O)NC1CN(c2ncc3ncnc(Nc4ccc(Oc5ccn6ncnc6c5)c(C)c4)c3n2)C1] |
| I-10 | 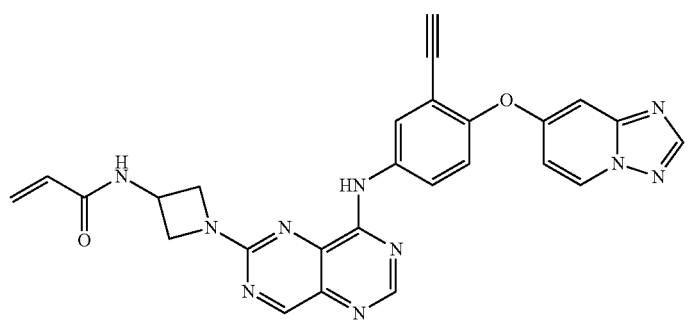 [SMILES: C#Cc1cc(Nc2ncnc3cnc(N4CC(NC(=O)C=C)C4)nc23)ccc1Oc1ccn2ncnc2c1] |
| I-11 | 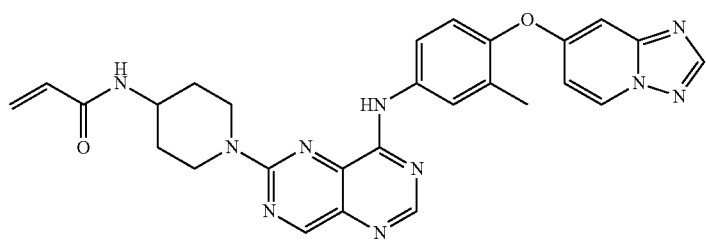 [SMILES: C=CC(=O)NC1CCN(c2ncc3ncnc(Nc4ccc(Oc5ccn6ncnc6c5)c(C)c4)c3n2)CC1] |
| I-12 | 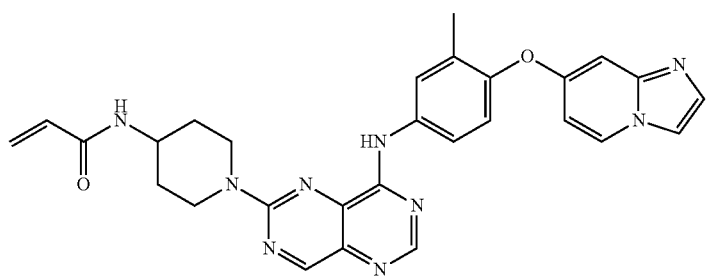 [SMILES: C=CC(=O)NC1CCN(c2ncc3ncnc(Nc4ccc(Oc5ccn6ccnc6c5)c(C)c4)c3n2)CC1] |
| I-13 | 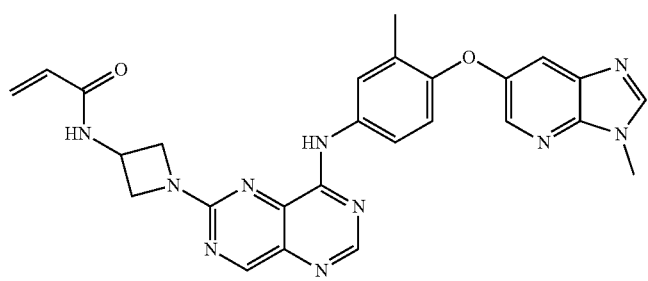 [SMILES: C=CC(=O)NC1CN(c2ncc3ncnc(Nc4ccc(Oc5cnc6c(c5)ncn6C)c(C)c4)c3n2)C1] |

-continued
| Example | Structure |
|---------|-----------|
| I-14 | 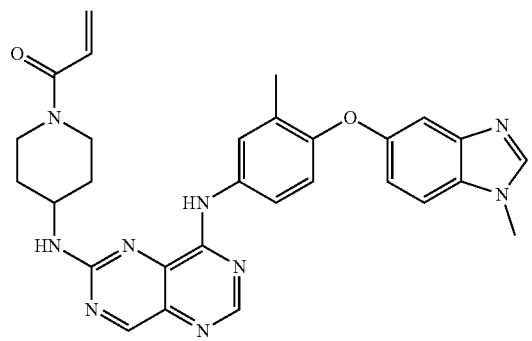 [SMILES: C=CC(=O)N1CCC(Nc2ncc3ncnc(Nc4ccc(Oc5ccc6c(c5)ncn6C)c(C)c4)c3n2)CC1] |
| I-15 | 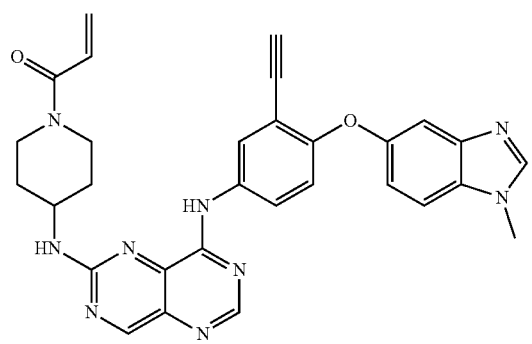 [SMILES: C#Cc1cc(Nc2ncnc3cnc(NC4CCN(C(=O)C=C)CC4)nc23)ccc1Oc1ccc2c(c1)ncn2C] |
| I-16 | 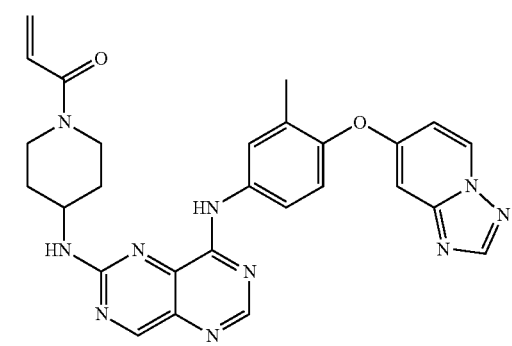 [SMILES: C=CC(=O)N1CCC(Nc2ncc3ncnc(Nc4ccc(Oc5ccn6ncnc6c5)c(C)c4)c3n2)CC1] |
| I-17 | 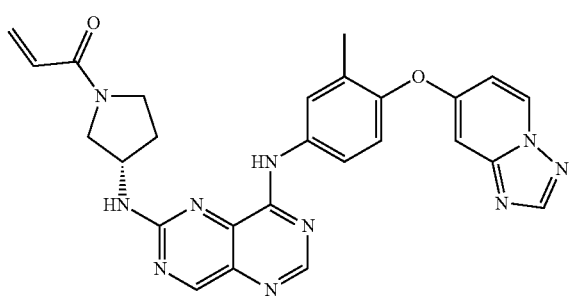 [SMILES: C=CC(=O)N1CC[C@H](Nc2ncc3ncnc(Nc4ccc(Oc5ccn6ncnc6c5)c(C)c4)c3n2)C1] |
| I-18 | 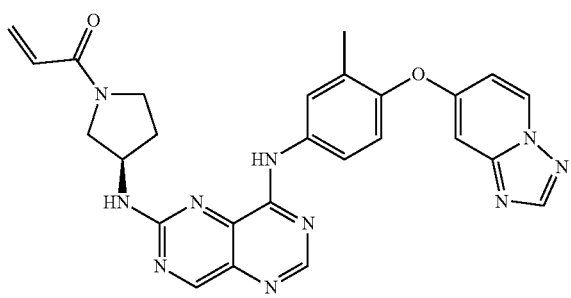 [SMILES: C=CC(=O)N1CC[C@@H](Nc2ncc3ncnc(Nc4ccc(Oc5ccn6ncnc6c5)c(C)c4)c3n2)C1] |

| Example | Structure |
| --- | --- |
| I-19 | (structure) | or a pharmaceutically acceptable salt thereof.

A further preferred embodiment of the current invention are the above compounds of Formula (I), selected from the group consisting of examples I-01 to I-19.

A further preferred embodiment of the current invention are pharmaceutically acceptable salts of the above compounds of Formula (I), selected from the group consisting of examples I-01 to I-19.

A further preferred embodiment of the current invention are the above compounds of Formula (I), selected from the group consisting of examples I-01 to I-13.

A further preferred embodiment of the current invention are pharmaceutically acceptable salts of the above compounds of Formula (I), selected from the group consisting of examples I-01 to I-13.

A further preferred embodiment of the current invention are the above compounds of Formula (I), selected from the group consisting of examples I-14 to I-19.

A further preferred embodiment of the current invention are pharmaceutically acceptable salts of the above compounds of Formula (I), selected from the group consisting of examples I-14 to I-19.

A further preferred embodiment of the current invention is the compound of example I-01.

A further preferred embodiment of the current invention is the compound of example I-02.

A further preferred embodiment of the current invention is the compound of example I-03.

A further preferred embodiment of the current invention is the compound of example I-04.

A further preferred embodiment of the current invention is the compound of example I-05.

A further preferred embodiment of the current invention is the compound of example I-06.

A further preferred embodiment of the current invention is the compound of example I-07.

A further preferred embodiment of the current invention is the compound of example I-08.

A further preferred embodiment of the current invention is the compound of example I-09.

A further preferred embodiment of the current invention is the compound of example I-10.

A further preferred embodiment of the current invention is the compound of example I-11.

A further preferred embodiment of the current invention is the compound of example I-12.

A further preferred embodiment of the current invention is the compound of example I-13.

A further preferred embodiment of the current invention is the compound of example I-14.

A further preferred embodiment of the current invention is the compound of example I-15.

A further preferred embodiment of the current invention is the compound of example I-16.

A further preferred embodiment of the current invention is the compound of example I-17.

A further preferred embodiment of the current invention is the compound of example I-18.

A further preferred embodiment of the current invention is the compound of example I-19.

A further preferred embodiment of the current invention are pharmaceutically acceptable salts of the compound of example I-01.

A further preferred embodiment of the current invention are pharmaceutically acceptable salts of the compound of example I-02.

A further preferred embodiment of the current invention are pharmaceutically acceptable salts of the compound of example I-03.

A further preferred embodiment of the current invention are pharmaceutically acceptable salts of the compound of example I-04.

A further preferred embodiment of the current invention are pharmaceutically acceptable salts of the compound of example I-05.

A further preferred embodiment of the current invention are pharmaceutically acceptable salts of the compound of example I-06.

A further preferred embodiment of the current invention are pharmaceutically acceptable salts of the compound of example I-07.

A further preferred embodiment of the current invention are pharmaceutically acceptable salts of the compound of example I-08.

A further preferred embodiment of the current invention are pharmaceutically acceptable salts of the compound of example I-09.

A further preferred embodiment of the current invention are pharmaceutically acceptable salts of the compound of example I-10.

A further preferred embodiment of the current invention are pharmaceutically acceptable salts of the compound of example I-11.

A further preferred embodiment of the current invention are pharmaceutically acceptable salts of the compound of example I-12.

A further preferred embodiment of the current invention are pharmaceutically acceptable salts of the compound of example I-13.

A further preferred embodiment of the current invention are pharmaceutically acceptable salts of the compound of example I-14.

A further preferred embodiment of the current invention are pharmaceutically acceptable salts of the compound of example I-15.

A further preferred embodiment of the current invention are pharmaceutically acceptable salts of the compound of example I-16.

A further preferred embodiment of the current invention are pharmaceutically acceptable salts of the compound of example I-17.

A further preferred embodiment of the current invention are pharmaceutically acceptable salts of the compound of example I-18.

A further preferred embodiment of the current invention are pharmaceutically acceptable salts of the compound of example I-19.

Another embodiment of the present invention is a pharmaceutical composition comprising a therapeutically effective amount of at least one compound of Formula (I) or a pharmaceutically acceptable salt thereof and one or more pharmaceutically acceptable excipients.

Another embodiment of the present invention is a compound of Formula (I) or a pharmaceutically acceptable salt thereof for use as a medicament.

Another embodiment of the present invention is the use of a compound of Formula (I) or a pharmaceutically acceptable salt thereof for treating a patient suffering from cancer including brain cancer, breast cancer, biliary cancer, bladder cancer, cervical cancer, colorectal cancer, endometrial cancer, skin cancer, esophagus tumor, head and neck tumor, gastrointestinal cancer, gallbladder tumor, kidney cancer, liver cancer, lung cancer or prostate cancer.

Another embodiment of the present invention is the use of a compound of Formula (I) or a pharmaceutically acceptable salt thereof for treating a patient suffering from breast cancer, bladder cancer, colorectal cancer, gastrointestinal cancer, esophageal cancer or lung cancer.

Another embodiment of the present invention is the use of a compound of Formula (I) or a pharmaceutically acceptable salt thereof for treating a patient suffering from cancers/tumors/carcinomas of the lung: e.g. non-small cell lung cancer (NSCLC) (squamous cell carcinoma, spindle cell carcinoma, adenocarcinoma, large cell carcinoma, clear cell carcinoma, bronchioalveolar), small cell lung cancer (SCLC) (oat cell cancer, intermediate cell cancer, combined oat cell cancer).

Another embodiment of the present invention is the use of a compound of Formula (I) or a pharmaceutically acceptable salt thereof for treating a patient suffering from NSCLC.

Another embodiment of the present invention is a pharmaceutical composition comprising additionally to a compound of Formula (I), a pharmaceutically active compound selected from the group consisting of a cytostatic and a cytotoxic active substance.

The present invention further relates to hydrates, solvates, polymorphs, metabolites and prodrugs of compounds of Formula (I) thereof.

In another embodiment the invention relates to a pharmaceutically acceptable salt of a compound of Formula (I).

In another aspect, the invention relates to a method of inhibiting wild type and/or mutant HER2 in a cell, comprising contacting the cell with a compound of Formula (I). In another embodiment, the invention relates to a method of inhibiting HER2 carrying exon 20 mutations in a cell, preferably comprising contacting the cell with a compound of Formula (I).

In another aspect, the invention relates to a method of inhibiting phosphorylation of wild type and/or mutant HER2 in a cell, comprising contacting the cell with a compound of Formula (I). In another embodiment, the invention relates to a method of inhibiting phosphorylation of HER2 exon 20 mutant in a cell, comprising contacting the cell with a compound of Formula (I).

In another aspect, the invention relates to the use of a compound of Formula (I)—or a pharmaceutically acceptable salt thereof—for the treatment and/or prevention of a disease and/or condition, wherein the inhibition of wild type and/or mutant HER2 is of therapeutic benefit. In another embodiment, the invention relates to the use of a compound of Formula (I)—or a pharmaceutically acceptable salt thereof—for the treatment and/or prevention of a disease and/or condition, wherein the inhibition of HER2 exon 20 mutant protein is of therapeutic benefit.

In another aspect, the invention relates to a compound of Formula (I)—or a pharmaceutically acceptable salt thereof—for use in a method for inhibiting wild type and/or mutant HER2, in a human subject in need thereof, comprising administering to the subject a therapeutically effective amount of compound of Formula (I)—or a pharmaceutically acceptable salt thereof. In another embodiment, the invention relates to a compound of Formula (I)—or a pharmaceutically acceptable salt thereof—for use in a method for inhibiting HER2 exon 20 mutant, in a human subject in need thereof, comprising administering to the subject a therapeutically effective amount of compound of Formula (I)—or a pharmaceutically acceptable salt thereof.

In another aspect, the invention relates a compound of Formula (I)—or a pharmaceutically acceptable salt thereof—for use as a medicament.

In another aspect, the invention relates to a compound of Formula (I),—or a pharmaceutically acceptable salt thereof—for the treatment and/or prevention of cancer. In another embodiment, the invention relates to a compound of Formula (I)—or a pharmaceutically acceptable salt thereof—for the treatment and/or prevention of cancer, wherein the cancer is with HER2 overexpression and/or HER2 amplification. In another embodiment, the invention relates to a compound of Formula (I)—or a pharmaceutically acceptable salt thereof—for the treatment and/or prevention of cancer, wherein the cancer is HER2 exon 20 mutant cancer. In another embodiment, the invention relates to a compound of Formula (I)—or a pharmaceutically acceptable salt thereof—for the treatment and/or prevention of cancer, wherein the HER2 overexpressed, HER2 amplified and/or HER2 exon 20 mutant cancer is selected from brain cancer, breast cancer, biliary cancer, bladder cancer, cervical cancer, colorectal cancer, endometrial cancer, skin cancer, esophagus tumor, head and neck tumor, gastrointestinal cancer, gallbladder tumor, kidney cancer, liver cancer, lung cancer and prostate cancer.

In another aspect, the invention relates to a method of treating and/or preventing above mentioned diseases and conditions comprising administering a therapeutically effective amount of a compound of Formula (I)—or a pharmaceutically acceptable salt thereof—to a human.

In another aspect, the present invention relates to a compound of Formula (I)—or a pharmaceutically acceptable salt thereof—for use in the treatment and/or prevention of above mentioned diseases and conditions.

In another aspect the present invention relates to the use of a compound of Formula (I)—or a pharmaceutically acceptable salt thereof—for the preparation of a medicament for the treatment and/or prevention of above mentioned diseases and conditions.

Furthermore, the following cancers, tumors and other proliferative diseases may be treated with compounds of the invention, without being restricted thereto:

Cancers/tumors/carcinomas of the head and neck: e.g. tumors/carcinomas/cancers of the nasal cavity, paranasal sinuses, nasopharynx, oral cavity (including lip, gum, alveolar ridge, retromolar trigone, floor of mouth, tongue, hard palate, buccal mucosa), oropharynx (including base of tongue, tonsil, tonsillar pilar, soft palate, tonsillar fossa, pharyngeal wall), middle ear, larynx (including supraglottis, glottis, subglottis, vocal cords), hypopharynx, salivary glands (including minor salivary glands);

cancers/tumors/carcinomas of the lung: e.g. non-small cell lung cancer (NSCLC) (squamous cell carcinoma, spindle cell carcinoma, adenocarcinoma, large cell carcinoma, clear cell carcinoma, bronchioalveolar), small cell lung cancer (SCLC) (oat cell cancer, intermediate cell cancer, combined oat cell cancer);

neoplasms of the mediastinum: e.g. neurogenic tumors (including neurofibroma, neurilemoma, malignant schwannoma, neurosarcoma, ganglioneuroblastoma, ganglioneuroma, neuroblastoma, pheochromocytoma, paraganglioma), germ cell tumors (including seminoma, teratoma, non-seminoma), thymic tumors (including thymoma, thymolipoma, thymic carcinoma, thymic carcinoid), mesenchymal tumors (including fibroma, fibrosarcoma, lipoma, liposarcoma, myxoma, mesothelioma, leiomyoma, leiomyosarcoma, rhabdomyosarcoma, xanthogranuloma, mesenchymoma, hemangioma, hemangioendothelioma, hemangiopericytoma, lymphangioma, lymphangiopericytoma, lymphangiomyoma);

cancers/tumors/carcinomas of the gastrointestinal (GI) tract: e.g. tumors/carcinomas/cancers of the esophagus, stomach (gastric cancer), pancreas, liver and biliary tree (including hepatocellular carcinoma (HCC), e.g. childhood HCC, fibrolamellar HCC, combined HCC, spindle cell HCC, clear cell HCC, giant cell HCC, carcinosarcoma HCC, sclerosing HCC; hepatoblastoma; cholangiocarcinoma; cholangiocellular carcinoma; hepatic cystadenocarcinoma; angiosarcoma, hemangioendothelioma, leiomyosarcoma, malignant schwannoma, fibrosarcoma, Klatskin tumor), gall bladder, extrahepatic bile ducts, small intestine (including duodenum, jejunum, ileum), large intestine (including cecum, colon, rectum, anus; colorectal cancer, gastrointestinal stroma tumor (GIST)), genitourinary system (including kidney, e.g. renal pelvis, renal cell carcinoma (RCC), nephroblastoma (Wilms' tumor), hypernephroma, Grawitz tumor; ureter; urinary bladder, e.g. urachal cancer, urothelial cancer; urethra, e.g. distal, bulbomembranous, prostatic; prostate (androgen dependent, androgen independent, castration resistant, hormone independent, hormone refractory), penis);

cancers/tumors/carcinomas of the testis: e.g. seminomas, non-seminomas;

Gynecologic cancers/tumors/carcinomas: e.g. tumors/carcinomas/cancers of the ovary, fallopian tube, peritoneum, cervix, vulva, vagina, uterine body (including endometrium, fundus);

cancers/tumors/carcinomas of the breast: e g mammary carcinoma (infiltrating ductal, colloid, lobular invasive, tubular, adenocystic, papillary, medullary, mucinous), hormone receptor positive breast cancer (estrogen receptor positive breast cancer, progesterone receptor positive breast cancer), HER2 positive breast cancer, triple negative breast cancer, Paget's disease of the breast;

cancers/tumors/carcinomas of the endocrine system: e.g. tumors/carcinomas/cancers of the endocrine glands, thyroid gland (thyroid carcinomas/tumors; papillary, follicular, anaplastic, medullary), parathyroid gland (parathyroid carcinoma/tumor), adrenal cortex (adrenal cortical carcinoma/tumors), pituitary gland (including prolactinoma, craniopharyngioma), thymus, adrenal glands, pineal gland, carotid body, islet cell tumors, paraganglion, pancreatic endocrine tumors (PET; nonfluorineunctional PET, PPoma, gastrinoma, insulinoma, VIPoma, glucagonoma, somatostatinoma, GRFoma, ACTHoma), carcinoid tumors;

sarcomas of the soft tissues: e.g. fibrosarcoma, fibrous histiocytoma, liposarcoma, leiomyosarcoma, rhabdomyosarcoma, angiosarcoma, lymphangiosarcoma, Kaposi's sarcoma, glomus tumor, hemangiopericytoma, synovial sarcoma, giant cell tumor of tendon sheath, solitary fibrous tumor of pleura and peritoneum, diffuse mesothelioma, malignant peripheral nerve sheath tumor (MPNST), granular cell tumor, clear cell sarcoma, melanocytic schwannoma, plexosarcoma, neuroblastoma, ganglioneuroblastoma, neuroepithelioma, extraskeletal Ewing's sarcoma, paraganglioma, extraskeletal chondrosarcoma, extraskeletal osteosarcoma, mesenchymoma, alveolar soft part sarcoma, epithelioid sarcoma, extrarenal rhabdoid tumor, desmoplastic small cell tumor; sarcomas of the bone: e.g. myeloma, reticulum cell sarcoma, chondrosarcoma (including central, peripheral, clear cell, mesenchymal chondrosarcoma), osteosarcoma (including parosteal, periosteal, high-grade surface, small cell, radiation-induced osteosarcoma, Paget's sarcoma), Ewing's tumor, malignant giant cell tumor, adamantinoma, (fibrous) histiocytoma, fibrosarcoma, chordoma, small round cell sarcoma, hemangioendothelioma, hemangiopericytoma, osteochondroma, osteoid osteoma, osteoblastoma, eosinophilic granuloma, chondroblastoma;

mesothelioma: e.g. pleural mesothelioma, peritoneal mesothelioma;

cancers of the skin: e.g. basal cell carcinoma, squamous cell carcinoma, Merkel's cell carcinoma, melanoma (including cutaneous, superficial spreading, lentigo maligna, acral lentiginous, nodular, intraocular melanoma), actinic keratosis, eyelid cancer; neoplasms of the central nervous system and brain: e.g. astrocytoma (cerebral, cerebellar, diffuse, fibrillary, anaplastic, pilocytic, protoplasmic, gemistocytary), glioblastoma, gliomas, oligodendrogliomas, oligoastrocytomas, ependymomas, ependymoblastomas, choroid plexus tumors, medulloblastomas, meningiomas, schwannomas, hemangioblastomas, hemangiomas, hemangiopericytomas, neuromas, ganglioneuromas, neuroblastomas, retinoblastomas, neurinomas (e.g. acoustic), spinal axis tumors; lymphomas and leukemias: e.g. B-cell non-Hodgkin lymphomas (NHL) (including small lymphocytic lymphoma (SLL), lymphoplasmacytoid lymphoma (LPL), mantle cell lymphoma (MCL), follicular lymphoma (FL), diffuse large cell lymphoma (DLCL), Burkitt's lymphoma (BL)), T-cell non-Hodgkin lymphomas (including anaplastic large cell lymphoma (ALCL), adult T-cell leukemia/lymphoma (ATLL), cutaneous T-cell lymphoma (CTCL), peripheral T-cell lymphoma (PTCL)), lymphoblastic T-cell lymphoma (T-LBL), adult T-cell lymphoma, lymphoblastic B-cell lymphoma (B-LBL), immunocytoma, chronic B-cell lymphocytic leukemia (BchlorineL), chronic T-cell lymphocytic leukemia (TchlorineL) B-cell small lymphocytic lymphoma (B-SLL), cutaneous T-cell lymphoma (CTLC), primary central nervous system lymphoma (PCNSL), immunoblastoma, Hodgkin's disease (HD) (including nodular lymphocyte predominance HD (NLPHD), nodular sclerosis HD (NSHD), mixed-cellularity HD (MCHD), lymphocyte-rich classic HD, lymphocyte-depleted HD (LDHD)), large granular lymphocyte leukemia (LGL), chronic myelogenous leukemia (CML), acute myelogenous/myeloid leukemia (AML), acute lymphatic/lymphoblastic leukemia (ALL), acute promyelocytic leukemia (APL), chronic lymphocytic/lymphatic leukemia (CLL), prolymphocytic leukemia (PLL), hairy cell leukemia, chronic myelogenous/myeloid leukemia (CML), myeloma, plasmacytoma, multiple myeloma (MM), plasmacytoma, myelodysplastic syndromes (MDS), chronic myelomonocytic leukemia (CMML);

cancers of unknown primary site (CUP).

All cancers/tumors/carcinomas mentioned above which are characterized by their specific location/origin in the body are meant to include both the primary tumors and the metastatic tumors derived therefrom.

All cancers/tumors/carcinomas mentioned above may be further differentiated by their histopathological classification:

Epithelial cancers, e.g. squamous cell carcinoma (SCC) (carcinoma in situ, superficially invasive, verrucous carcinoma, pseudosarcoma, anaplastic, transitional cell, lymphoepithelial), adenocarcinoma (AC) (well-differentiated, mucinous, papillary, pleomorphic giant cell, ductal, small cell, signet-ring cell, spindle cell, clear cell, oat cell, colloid, adenosquamous, mucoepidermoid, adenoid cystic), mucinous cystadenocarcinoma, acinar cell carcinoma, large cell carcinoma, small cell carcinoma, neuroendocrine tumors (small cell carcinoma, paraganglioma, carcinoid); oncocytic carcinoma; Nonepithilial cancers, e.g. sarcomas (fibrosarcoma, chondrosarcoma, rhabdomyosarcoma, leiomyosarcoma, hemangiosarcoma, giant cell sarcoma, lymphosarcoma, fibrous histiocytoma, liposarcoma, angiosarcoma, lymphangiosarcoma, neurofibrosarcoma), lymphoma, melanoma, germ cell tumors, hematological neoplasms, mixed and undifferentiated carcinomas.

In another aspect, the present invention relates to a compound of Formula (I)—or a pharmaceutically acceptable salt thereof—for use in the treatment and/or prevention of cancer, wherein the compound is to be administered in combination with a cytostatic and/or cytotoxic active substance and/or in combination with radiotherapy and/or immunotherapy.

In another aspect, the present invention relates to a combination of compound of Formula (I)—or a pharmaceutically acceptable salt thereof—with a cytostatic and/or cytotoxic active substance and/or in combination with radiotherapy and/or immunotherapy for use in the treatment and/or prevention of cancer.

In another aspect, the present invention relates to a method of treating and/or preventing cancer, wherein said method comprises administering a compound of Formula (I)—or a pharmaceutically acceptable salt thereof—in combination with a cytostatic and/or cytotoxic active substance and/or in combination with radiotherapy and/or immunotherapy and/or targeted therapy.

The compounds of the invention may be used on their own or in combination with one or several other pharmacologically active substances such as state-of-the-art or standard-of-care compounds, such as e.g. cell proliferation inhibitors, anti-angiogenic substances, steroids or immune modulators/checkpoint inhibitors, and the like.

Pharmacologically active substances which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors and/or of their corresponding receptors (growth factors such as for example platelet derived growth factor (PDGF), fibroblast growth factor (FGF), vascular endothelial growth factor (VEGF), epidermal growth factor (EGF), insuline-like growth factors (IGF), human epidermal growth factor (HER, e.g. HER2, HER3, HER4) and hepatocyte growth factor (HGF) and/or their corresponding receptors), inhibitors are for example (anti-)growth factor antibodies, (anti-)growth factor receptor antibodies and tyrosine kinase inhibitors, such as for example cetuximab, gefitinib, afatinib, nintedanib, imatinib, lapatinib, bosutinib, bevacizumab, pertuzumab and trastuzumab); antimetabolites (e.g. antifolates such as methotrexate, raltitrexed, pyrimidine analogues such as 5fluorouracil (5fluorineU), ribonucleoside and deoxyribonucleoside analogues, capecitabine and gemcitabine, purine and adenosine analogues such as mercaptopurine, thioguanine, cladribine and pentostatin, cytarabine (ara C), fludarabine); antitumour antibiotics (e.g. anthracyclins such as doxorubicin, doxil (pegylated liposomal doxorubicin hydrochloride, myocet (non-pegylated liposomal doxorubicin), daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); angiogenesis inhibitors (e.g. tasquinimod), tubuline inhibitors; DNA synthesis inhibitors, PARP inhibitors, topoisomerase inhibitors (e.g. epipodophyllotoxins such as for example etoposide and etopophos, teniposide, amsacrin, topotecan, irinotecan, mitoxantrone), serine/threonine kinase inhibitors (e.g. PDK 1 inhibitors, Raf inhibitors, A-Raf inhibitors, B-Raf inhibitors, C-Raf inhibitors, mTOR inhibitors, mTORC1/2 inhibitors, PI3K inhibitors, PI3Kα inhibitors, dual mTOR/PI3K inhibitors, STK 33 inhibitors, AKT inhibitors, PLK 1 inhibitors, inhibitors of CDKs, Aurora kinase inhibitors), tyrosine kinase inhibitors (e.g. PTK2/FAK inhibitors), protein protein interaction inhibitors (e.g. IAP activator, Mcl-1, MDM2/MDMX), MEK inhibitors, ERK inhibitors, KRAS inhibitors (e.g. KRAS G12C inhibitors), signalling pathway inhibitors (e.g. SOS1 inhibitors), FLT3 inhibitors, BRD4 inhibitors, IGF-1R inhibitors, TRAILR2 agonists, Bcl-xL inhibitors, Bcl-2 inhibitors, Bcl-2/Bcl-xL inhibitors, ErbB receptor inhibitors, BCR-ABL inhibitors, ABL inhibitors, Src inhibitors, rapamycin analogs (e.g. everolimus, temsirolimus, ridaforolimus, sirolimus), androgen synthesis inhibitors, androgen receptor inhibitors, DNMT inhibitors, HDAC inhibitors, ANG1/2 inhibitors, CYP17 inhibitors, radiopharmaceuticals, proteasome inhibitors, immunotherapeutic agents such as immune checkpoint inhibitors (e.g. CTLA4, PD1, PD-L1, PD-L2, LAG3, and TIM3 binding molecules/immunoglobulins, such as e.g. ipilimumab, nivolumab, pembrolizumab), ADCC (antibody-dependent cell-mediated cytotoxicity) enhancers (e.g. anti-CD33 antibodies, anti-CD37 antibodies, anti-CD20 antibodies), T-cell engagers (e.g. bi-specific T-cell engagers (BiTEs®) like e.g. CD3×BCMA, CD3×CD33, CD3×CD19), PSMA×CD3), tumor vaccines and various chemotherapeutic agents such as amifostin, anagrelid, clodronat, filgrastin, interferon, interferon alpha, leucovorin, procarbazine, levamisole, mesna, mitotane, pamidronate and porfimer.

In another aspect the invention relates to a pharmaceutical composition comprising at least one compound of Formula (I)—or a pharmaceutically acceptable salt thereof—and optionally at least one pharmaceutically acceptable carrier.

In another aspect the invention relates to a pharmaceutical composition comprising a compound of Formula (I)—or a pharmaceutically acceptable salt thereof—and at least one other cytostatic and/or cytotoxic active substance.

Suitable preparations for administering the compounds of the invention will be apparent to those with ordinary skill in the art and include for example tablets, pills, capsules, suppositories, lozenges, troches, solutions—particularly solutions for injection (s.c., i.v., i.m.) and infusion (injectables)—elixirs, syrups, sachets, emulsions, inhalatives or dispersible powders.

Suitable tablets may be obtained, for example, by mixing one or more compounds of Formula (I) with known excipients, for example inert diluents, carriers, disintegrants, adjuvants, surfactants, binders and/or lubricants.

The dosage range of the compounds of Formula (I) applicable per day is usually from 1 mg to 2000 mg, preferably from 10 to 1000 mg.

The dosage for intravenous use is from 1 mg to 1000 mg with different infusion rates, preferably between 5 mg and 500 mg with different infusion rates.

However, it may sometimes be necessary to depart from the amounts specified, depending on the body weight, age, the route of administration, severity of the disease, the individual response to the drug, the nature of its formulation and the time or interval over which the drug is administered (continuous or intermittent treatment with one or multiple doses per day). Thus, in some cases it may be sufficient to use less than the minimum dose given above, whereas in other cases the upper limit may have to be exceeded. When administering large amounts it may be advisable to divide them up into a number of smaller doses spread over the day.

GENERAL DEFINITIONS

Terms not specifically defined herein should be given the meanings that would be given to them by one of skilled in the art in light of the disclosure and the context. As used in the specification, however, unless specified to the contrary, the following terms have the meaning indicated and the following conventions are adhered to.

The asterisk may be used in sub-formulas to indicate the bond which is connected to the core molecule as defined.

In the groups, radicals, or moieties defined below, the number of carbon atoms is often specified preceding the group, for example, $C_{1-6}$ alkyl means an alkyl group or radical having 1 to 6 carbon atoms.

In groups like OH, $NH_2$, S(O), $S(O)_2$, CN (cyano), COOH, $CF_3$ or the like, the skilled artisan can see the radical attachment point(s) to the molecule from the free valences of the group itself.

In case a compound of the present invention is depicted in form of a chemical name and as a formula in case of any discrepancy the formula shall prevail. An asterisk may be used in subformulas to indicate the bond which is connected to the core molecule as defined.

The numeration of the atoms of a substituent starts with the atom which is closest to the core or to the group to which the substituent is attached.

The term "halogen" denotes fluorine, chlorine, bromine and/or iodine atoms.

The term "heterocyclyl" or "heterocycle" means a saturated or unsaturated mono- or polycyclic-ring systems including aromatic ring system containing one or more heteroatoms selected from N, O or $S(O)_r$, wherein r=0, 1 or 2, consisting of 3 to 14 ring atoms wherein none of the heteroatoms is part of the aromatic ring. The term "heterocyclyl" or "heterocycle" is intended to include all the possible isomeric forms.

Thus, the term "heterocyclyl" or "heterocycle" includes the following exemplary structures which are not depicted as radicals as each form are optionally attached through a covalent bond to any atom so long as appropriate valences are maintained:

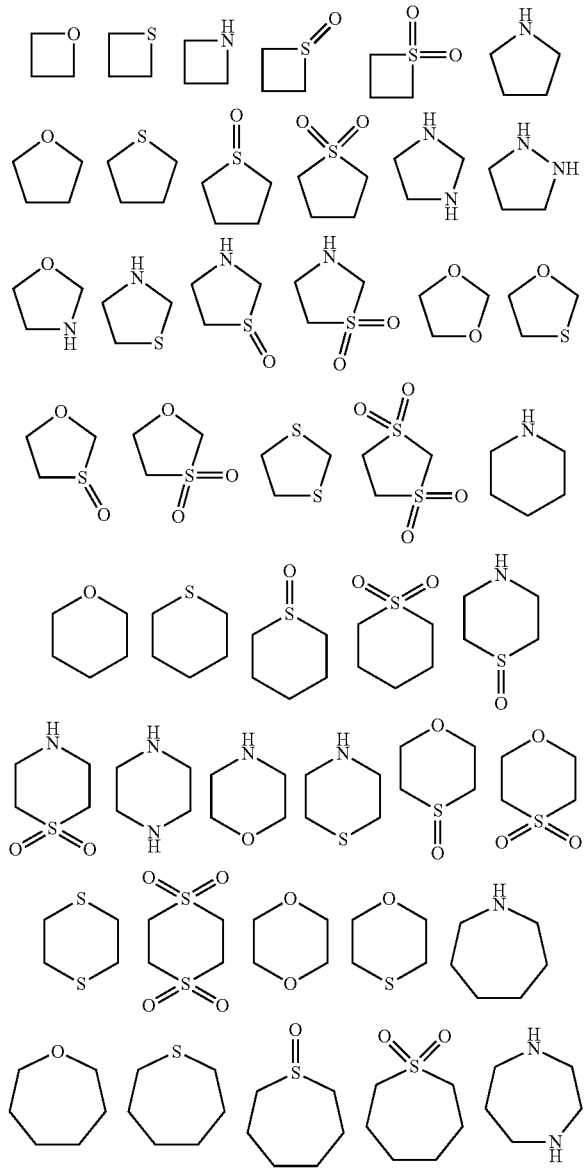

25
-continued
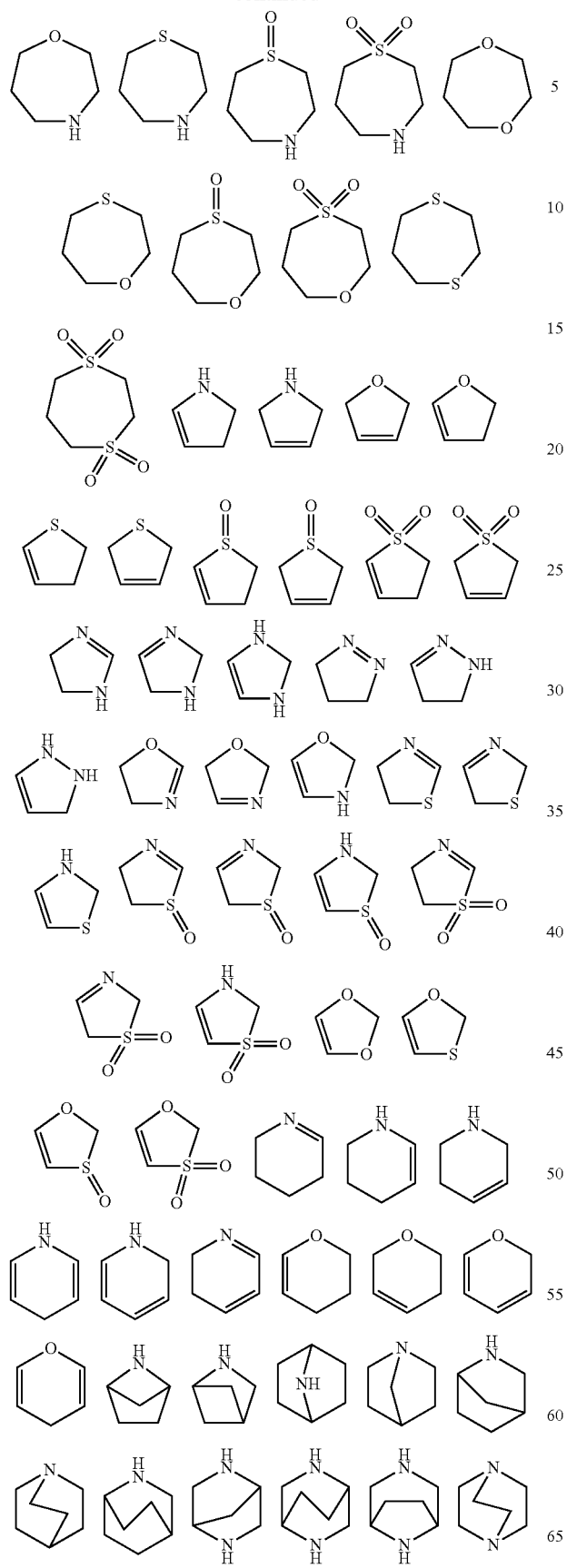
26
-continued
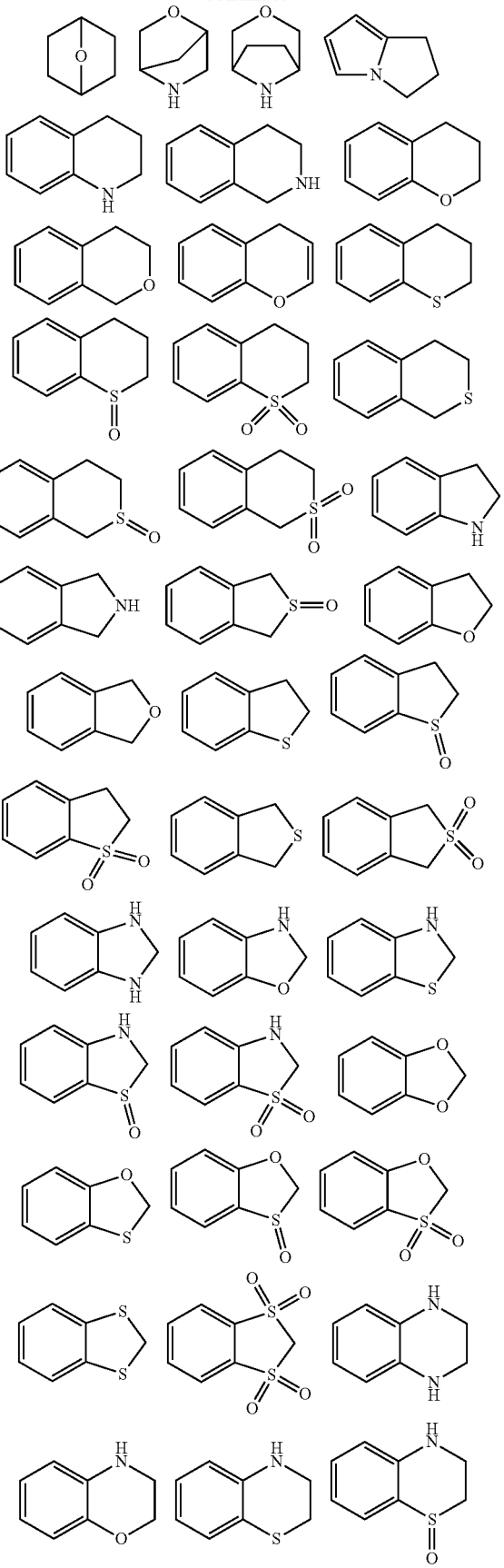

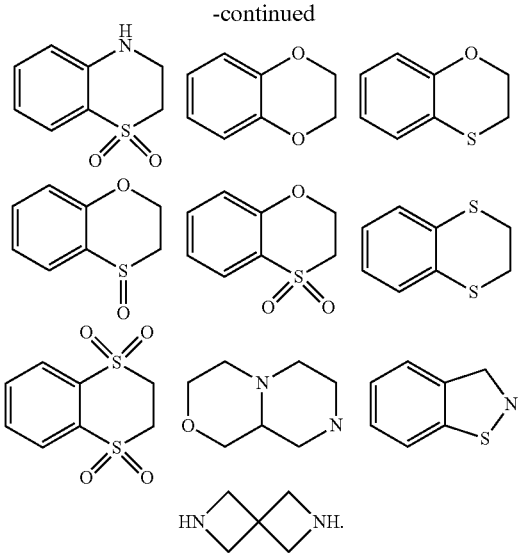

Many of the terms given above may be used repeatedly in the definition of a formula or group and in each case have one of the meanings given above, independently of one another.

The term "substituted" as used herein, means that any one or more hydrogens on the designated atom is replaced with a selection from the indicated group, provided that the designated atom's normal valence is not exceeded, and that the substitution results in a stable compound.

Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof, as well as mixtures in different proportions of the separate enantiomers, mixtures of diastereomers, or mixtures of any of the foregoing forms where such isomers and enantiomers exist, and solvates thereof, such as for instance hydrates of the free compound.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents.

Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases, or by resolution of a racemic mixture using an appropriate resolving agent, e.g. by means of diastereomeric salt formation of the racemic compound with optically active acids or bases, subsequent resolution of the salts and release of the desired compound from the salt, or by derivatization of the corresponding racemic compounds with optically active chiral auxiliary reagents, subsequent diastereomer separation and removal of the chiral auxiliary group, or by kinetic resolution of a racemate (e.g. by enzymatic resolution); by enantioselective crystallization from a conglomerate of enantiomorphous crystals under suitable conditions, or by (fractional) crystallization from a suitable solvent in the presence of an optically active chiral auxiliary.

The phrase "pharmaceutically acceptable" is employed herein to refer to those compounds, materials, compositions, and/or dosage forms which are, within the scope of sound medical judgement, suitable for use in contact with the tissues of human beings without excessive toxicity, irritation, allergic response, or other problem or complication, and commensurate with a reasonable benefit/risk ratio.

As used herein "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

The pharmaceutically acceptable salts of the present invention can be synthesized from the parent compound, which contains a basic or acidic moiety, by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts), also comprise a part of the invention.

Groups or substituents are frequently selected from among a number of alternative groups/substituents with a corresponding group designation (e.g. $R^a$, $R^b$ etc.). If such a group is used repeatedly to define a compound according to the invention in different parts of the molecule, it is pointed out that the various uses are to be regarded as totally independent of one another.

The term "therapeutically effective amount" as used herein refers to a quantity of substance that is capable of obviating symptoms of illness or of preventing or alleviating these symptoms, or which prolong the survival of a treated patient.

The term "prodrug" as used herein refers to (i) an inactive form of a drug that exerts its effects after metabolic processes within the body converting it to a usable or active form, or (ii) a substance that gives rise to a pharmacologically active metabolite, although not itself active (i.e. an inactive precursor).

The terms "prodrug" or "prodrug derivative" mean a covalently-bonded derivative, carrier or precursor of the parent compound or active drug substance which undergoes at least some biotransformation prior to exhibiting its pharmacological effect(s). Such prodrugs either have metabolically cleavable or otherwise convertible groups and are rapidly transformed in vivo to yield the parent compound, for example, by hydrolysis in blood or by activation via oxidation as in case of thioether groups. Most common prodrugs include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; Bioreversible Carriers in Drug Design, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans without undue toxicity, irritation, allergic response, and the like, commensurate with a reasonable benefit/risk ratio, and effective for their intended use, as well as the zwitter ionic forms, where possible.

The term "compound selective over EGFR wild type" as used herein refers to a compound exhibiting higher efficacy on HER2 compared to EGFR, where the efficacy of the compound can be determined in a biological assay such as a BA/F3 proliferation assay, or a tumor cell line proliferation assay as described below.

The term "sparing EGFR wild type" or "EGFR wild type sparing activity" as used herein refers to the low EGFR wild type efficacy of a compound, which can be determined in a biological assay such as a BA/F3 proliferation assay, or a tumor cell line proliferation assay as described below.

The term "cancer with HER2 amplification" as used herein refers to a cancer where the cancer cells exhibit more than 2 gene copies of ERBB2.

The term "cancer with HER2 overexpression" as used herein refers to a cancer, where the cells of the cancer express HER2 at levels detectable by immunohistochemistry and/or methods assaying ERBB2 messenger RNA.

The term "mutant HER2" or "HER2 carrying exon 20 mutation" as used herein refers to the mutant HER2 protein and concordant mutant DNA variant, whereas "HER2 exon 20 mutant" as used herein refers to the HER2 exon 20 mutant protein and concordant mutant DNA variant.

The term "HER2-mutant cancer" or "cancer with HER2 mutations" refers to a cancer where the cancer or tumor cells harbour HER2 mutation(s) including but not limited to the mutations listed in Table 1 and Table 2.

The term "cancer with HER2 exon 20 mutation" or "HER2 exon 20 mutant cancer" as used herein refers to a cancer where the cancer or tumor cells harbour at least one HER2 exon 20 mutation including but not limited to the mutations listed in Table 1.

ERBB2 (HER2) exon 20 encodes for a part of the kinase domain and ranges from amino acids 769 to 835. Every mutation, insertion, duplication or deletion within this region is defined as an exon 20 mutation including mutations listed in Table 1. In addition oncogenic HER2 mutations exist outside of exon 20 including mutations listed in Table 2.

TABLE 1

ERBB2 (HER2) exon 20 mutations ("p." is referring to the HER2 protein)

p.A772_G773insMMAY
p.Y772_A775_dup (YVMA)
p.A775_G776insYVMA
p.Y772insYVMA
p.M774delinsWLV
p.A775_G776insSVMA
p.A775_G776insVVMA
p.A775_G776insYVMS
p.A775_G776insC
p.A776_delinsVC
p.A776_delinsLC
p.A776_delinsVV
p.A776_delinsAVGC
p.A776_delinsIC
p.A776_V777delinsCVC
p.V777_insE
p.G778_P780dup (GSP)

TABLE 2

Alternative HER2 mutations ("p." is referring to the HER2 protein)

p.S310F
p.R678Q
p.L755S
p.S310Y
p.V842I
p.D769Y
p.D769H
p.R103Q
p.G1056S
p.I767M
p.L869R
p.L869R
p.T733I
p.T862A
p.V697L
p.R929W
p.D277H
p.D277Y
p.G660D

LIST OF ABBREVIATIONS

| | |
|---|---|
| APCI | atmospheric pressure chemical ionization |
| aq. | aqueous |
| Boc | tert-butyloxycarbonyl |
| DMF | N,N-dimethylformamide |
| DMSO | dimethylsulfoxide |
| ES | electrospray |
| ESI | electrospray ionization |
| FBS | Fetal bovine serum |
| h | hour(s) |
| HPLC | high performance liquid chromatography |
| LC | liquid chromatography |
| min | minutes |
| MS | mass spectrometry |
| MSD | mass selective detector |
| RP | reversed phase |
| sat. | saturated |

| | |
|---|---|
| tert | tertiary |
| THF | tetrahydrofuran |
| TLC | thin layer chromatography |
| $t_{Ret.}$ | retention time |
| UPLC | Ultra performance liquid chromatography |
| UV | ultraviolet |

Features and advantages of the present invention will become apparent from the following detailed examples, which illustrate the principles of the invention by way of example without restricting its scope:

Preparation of the Compounds According to the Invention

General

The compounds according to the present invention and their intermediates may be obtained using methods of synthesis which are known to the one skilled in the art and described in the literature of organic synthesis. Preferably, the compounds are obtained in analogous fashion to the methods of preparation explained more fully hereinafter, in particular as described in the experimental section. In some cases, the order in carrying out the reaction steps may be varied. Variants of the reaction methods that are known to the one skilled in the art, but not described in detail here, may also be used.

The general processes for preparing the compounds according to the invention will become apparent to the one skilled in the art studying the following schemes. Starting materials may be prepared by methods that are described in the literature or herein, or may be prepared in an analogous or similar manner Any functional groups in the starting materials or intermediates may be protected using conventional protecting groups. These protecting groups may be cleaved again at a suitable stage within the reaction sequence using methods familiar to the one skilled in the art.

General Reaction Schemes and Summary of the Synthesis Route

Compounds C according to the invention can be synthesized starting from commercially available para-flouronitrobenzenes (A) and alcohols, which are reacted in a substitution reaction and subsequent reduction of the nitro-group to yield the corresponding amines C (see e.g. Ishikawa et al., J. Med. Chem. 2011, 54 (23), 8030-8050; McDaniel et al., J. Med. Chem. 2017, 60 (20), 8369-8384).

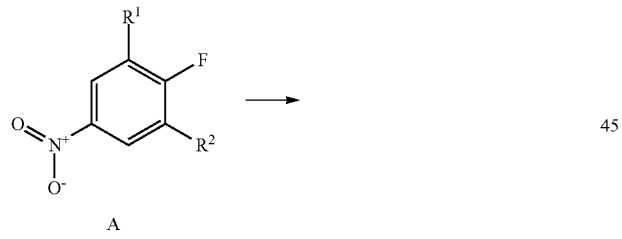

Scheme 3. General route 2 for the synthesis of compounds F-05-F-19

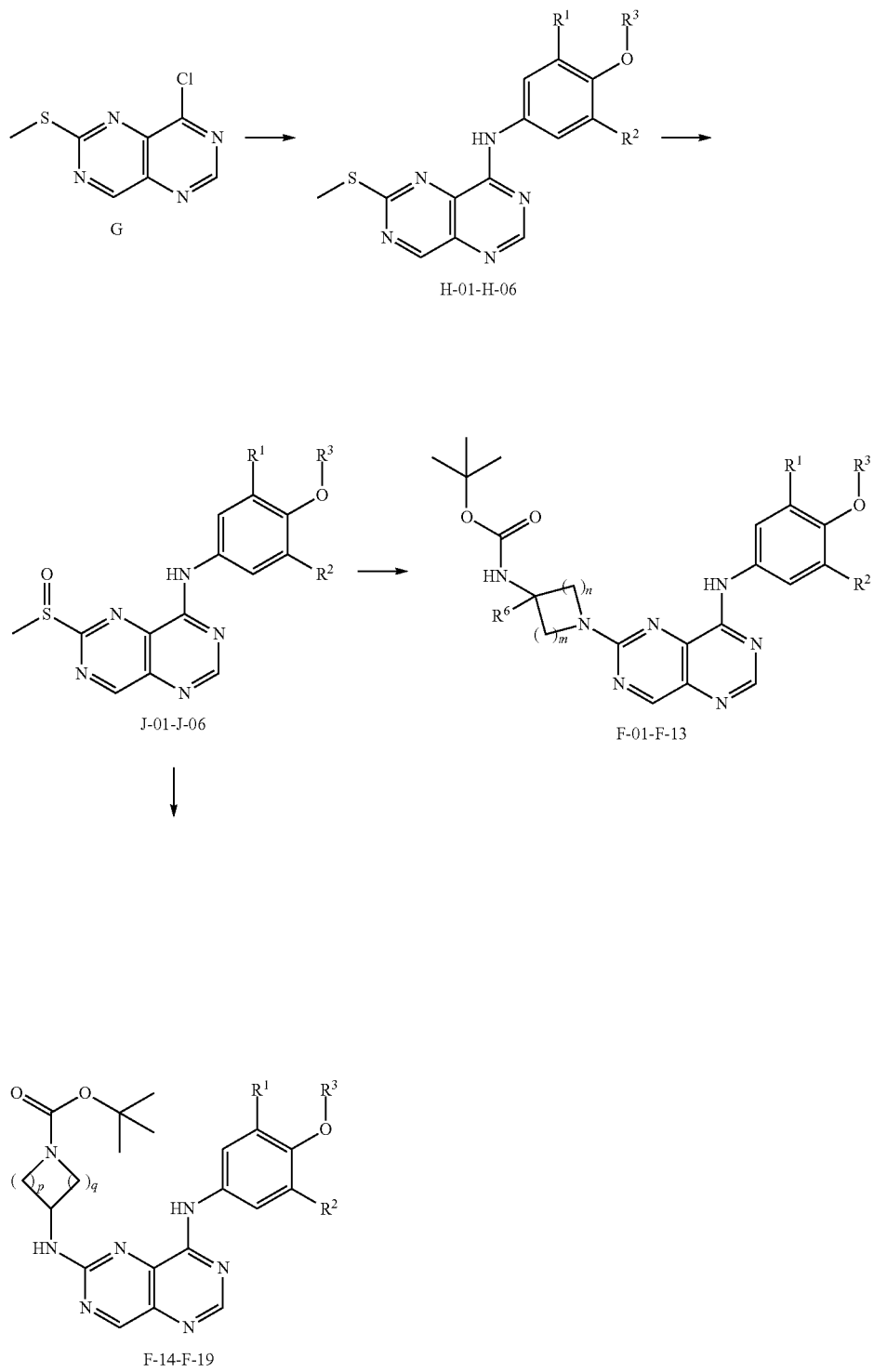

Compounds F according to the invention can be synthesized according to General Route 1 from compound D (see e.g. Wang et al. Bioorg. Med. Chem. Lett. 2016, 26 (11), 2589-2593, Wan et al., Org. Lett. 2006, 8, 11, 2425-2428). Alternatively, compounds F according to the invention can be synthesized according to General Route 2 from compound G, which is substituted with the relevant aniline (see e.g. Wang et al., Bioorg. Med. Chem. Lett. 2016, 26 (11), 2589-2593, Wan et al., Org. Lett. 2006, 8, 11, 2425-2428). The alkylsulfide H is oxidized to the sulfoxide J or sulfone and substituted with the substituted or unsubstituted amines (see e.g. Del Bello et al., Bioorg. Med. Chem. 2015, 23 (17), 5725-5733).

Scheme 4a. Synthesis of compounds I-01-I-13

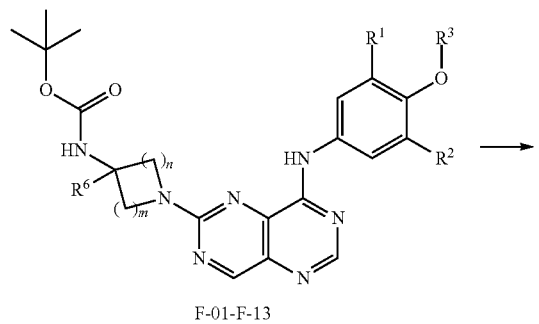

F-01-F-13

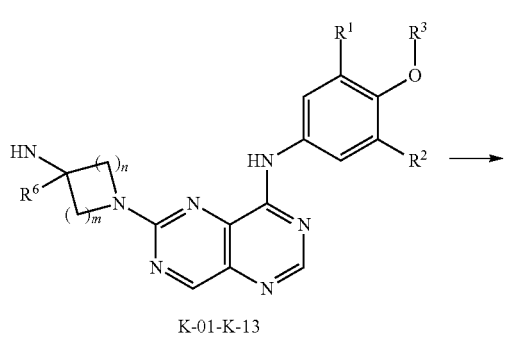

K-01-K-13

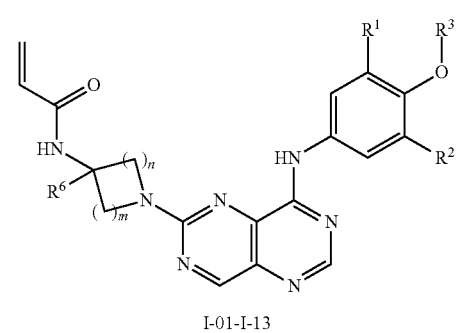

I-01-I-13

Scheme 4b. Synthesis of compounds I-14-I-19

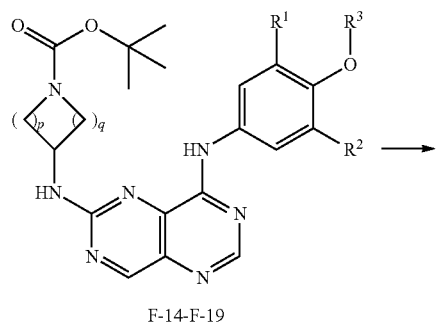

F-14-F-19

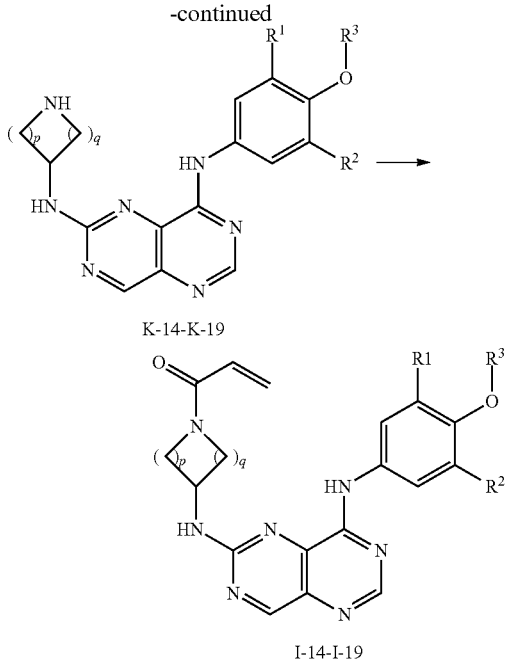

K-14-K-19

I-14-I-19

Compounds of Formula (I) according to the invention can be synthesized from compounds F by deprotecting the Boc-protected substituted or unsubstituted amine and subsequent reaction with acryloyl chloride or acryloyl anhydride (see e.g. Zhang et al., Eur. J. Med. Chem. 2019, 178, 417-432).

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

The compounds according to the invention are named in accordance with CAS rules using the software AutoNom (Beilstein) or MarvinSketch (ChemAxon, product version 17.24.3). If a compound is to be represented both by a structural formula and by its nomenclature, in the event of a conflict the structural formula is decisive.

The example compounds of Formula (I), I-01 to I-19, and intermediates are prepared by the methods of synthesis described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or their synthesis is described in the prior art or they may be prepared analogously to known prior art compounds or methods described herein, i.e. it is within the skills of an organic chemist to synthesize these compounds. Substances described in the literature can be prepared according to the published methods of synthesis.

Chromatography

Thin layer chromatography is carried out on ready-made silica gel 60 TLC plates on glass (with fluorescence indicator F-254) made by Merck.

Preparative high pressure chromatography (RP HPLC) of the example compounds is carried out on Agilent or Gilson systems with columns made by Waters (names: SunFire™

Prep C18, OBD™ 10 μm, 50×150 mm or SunFire™ Prep C18 OBD™ 5 μm, 30×50 mm or XBridge™ Prep C18, OBD™ 10 μm, 50×150 mm or XBridge™ Prep C18, OBD™ 5 μm, 30×150 mm or XBridge™ Prep C18, OBD™ 5 μm, 30×50 mm) and YMC (name: Actus-Triart Prep C18, 5 μm, 30×50 mm).

Different gradients of $H_2O$/acetonitrile are used to elute the compounds. For Agilent systems 5% acidic modifier (20 mL HCOOH to 1 L $H_2O$/acetonitrile (1/1)) is added to the water (acidic conditions). For Gilson systems 0.1% HCOOH is added to the water.

For the chromatography under basic conditions for Agilent systems $H_2O$/acetonitrile gradients are used, 5% basic modifier is added to the aqueous eluent (50 g $NH_4HCO_3$+50 mL $NH_3$ (25% in $H_2O$)+$H_2O$ for 1 L aqueous eluent). For Gilson systems the aqueous eluent consists of 5 mL $NH_4HCO_3$ solution (158 g in 1 L $H_2O$) and 2 mL $NH_3$ (28% in $H_2O$), replenished to 1 L with $H_2O$.

HPLC-MS columns used were from Waters (XBridge™ C18, 2.5 μm, 2.1×20 mm or XBridge™ C18, 2.5 μm, 2.1×30 mm or Aquity UPLC BEH C18, 1.7 μm, 2.1×50 mm), YMC (Triart C18, 3.0 μm, 2.0×30 mm) and Phenomenex (Luna C18, 5.0 μm, 2.0×30 mm).

HPLC-Mass Spectroscopy/UV-Spectrometry

The retention times/MS-ESI+ for characterizing the example compounds according to the invention are produced using an HPLC-MS apparatus (high performance liquid chromatography with mass detector). Compounds that elute at the injection peak are given the retention time $t_{Ret.}$=0.00.

| Method 1 | |
|---|---|
| HPLC | Agilent 1100/1200 system |
| MS | 1200 Series LC/MSD (MM-ES + APCI + 3000 V, Quadrupol, G6130) |
| MSD signal settings | Scan pos 150-750 |
| column | Waters; Part. No. 186003020; XBridge BEH C18, 3.5 μm, 30 × 2.1 mm column or Waters; Part. No. 186006028; XBridge BEH C18 XP, 2.5 μm, 30 × 2.1 mm column |
| eluent | 5 mM $NH_4HCO_3$/18 mM $NH_3$ (pH = 9.2) B: acetonitrile (HPLC grade) |
| detection signal | UV 254 nm (bandwidth 8, reference off) |
| spectrum | range: 190-400 nm; step: 2 nm |
| peak width | >0.0031 min (0.063 s) (80 Hz) |
| injection | 0.5 μL standard injection |
| flow | 1.4 mL/min |
| column temperature | 45° C. |
| gradient | 0.0-1.0 min 15% → 95% B 1.0-1.3 min 95% B Stop time: 1.3 min |

| Method 2 | |
|---|---|
| HPLC | Agilent 1100/1200 system |
| MS | 1200 Series LC/MSD (API-ES +/− 3000 V, Quadrupol, G6140) |
| MSD signal settings | Scan pos 150-750, Scan neg 150-750 |
| column | YMC; Part. No. TA12S03-0302WT; Triart C18, 3 μm, 12 nm; 30 × 2.0 mm column |
| eluent | A: $H_2O$ + 0.11% formic acid B: acetonitrile + 0.1% formic acid (HPLC grade) |
| detection signal | UV 254 nm (bandwidth 10, reference off) |
| spectrum | range: 190-400 nm; step: 4 nm |
| peak width | >0.005 min (0.1 s) |
| injection | 0.5 μL standard injection |
| flow | 1.4 mL/min |
| column temperature | 45° C. |
| gradient | 0.0-1.0 min 15% → 100% B 1.0-1.1 min 100% B Stop time: 1.23 min |

| Method 3 | |
|---|---|
| HPLC | Agilent 1100/1200 system |
| MS | 1200 Series LC/MSD (MM-ES + APCI +/− 4000 V, Quadrupol, G6130) |
| MSD signal settings | Scan pos 150-800, Scan neg 150-800 |
| column | Waters; Part. No. 186003020; XBridge BEH C18, 3.5 μm, 30 × 2.1 mm column or Waters; Part. No. 186006028; XBridge BEH C18 XP, 2.5 μm, 30 × 2.1 mm column |
| eluent | 5 mM $NH_4HCO_3$/18 mM $NH_3$ (pH = 9.2) B: acetonitrile (HPLC grade) |
| detection signal | UV 254 nm (bandwidth 8, reference off) |
| spectrum | range: 190-400 nm; step: 4 nm |
| peak width | >0.0031 min (0.063 s) |
| injection | 0.5 μL standard injection |
| flow | 1.4 mL/min |
| column temperature | 45° C. |
| gradient | 0.0-1.0 min 15% → 95% B 1.0-1.3 min 95% B Stop time: 1.3 min |

| Method 4 | |
|---|---|
| HPLC | Agilent 1100/1200 system |
| MS | 1200 Series LC/MSD (API-ES +/− 3000 V, Quadrupol, G6140) |
| MSD signal settings | Scan pos 150-750 |
| column | YMC; Part. No. TA12S03-0302WT; Triart C18, 3 μm, 12 nm; 30 × 2.0 mm column |
| eluent | A: $H_2O$ + 0.11% formic acid B: MeCN + 0.1% formic acid (HPLC grade) |
| detection signal | UV 254 nm (bandwidth 10, reference off) |
| spectrum | range: 190-400 nm; step: 4 nm |
| peak width | >0.005 min (0.1 s) |
| injection | 0.5 μL standard injection |
| flow | 1.4 mL/min |
| column temperature | 45° C. |
| gradient | 0.0-1.0 min 15% → 100% B 1.0-1.1 min 100% B Stop time: 1.23 min |

| Method 5 | |
|---|---|
| HPLC | Agilent 1260 system |
| MS | 1200 Series LC/MSD (API-ES +/− 3000 V, Quadrupol, G6140) |
| MSD signal settings | Scan pos/neg 120-900 m/z |
| column | Waters, Xbridge C18, 2.5 μm, 2.1 × 20 mm column |
| eluent | A: 20 mM $NH_4HCO_3$/$NH_3$ pH 9 B: acetonitrile HPLC grade |
| detection signal | 315 nm (bandwidth 170 nm, reference off) |
| spectrum | range: 230-400 nm |
| peak width | <0.01 min |
| injection | 5 μL standard injection |
| column temperature | 60° C. |
| flow | 1.00 mL/min |
| gradient | 0.00-1.50 min 10% → 95% B 1.50-2.00 min 95% B 2.00-2.10 min 95% → 10% B |

| Method 6 | |
|---|---|
| HPLC | Agilent 1100/1200 system |
| MS | 1200 Series LC/MSD (MM-ES + APCI +/− 3000 V, Quadrupol, G6130B) |

| | |
|---|---|
| MSD signal settings | Scan pos/neg 150-750 |
| column | Waters, Part. No. 186003389, XBridge BEH C18, 2.5 μm, 2.1 × 30 mm) column |
| eluent | A: 5 mM NH$_4$HCO$_3$/18 mM NH$_3$ (pH = 9.2)<br>B: acetonitrile (HPLC grade) |
| detection signal | UV 254 nm, 230 nm, 214 nm (bandwidth 8, reference off) |
| spectrum | range: 190-400 nm; slit: 4 nm |
| peak width | >0.0031 min (0.063 s response time, 80 Hz) |
| injection | 0.5 μL standard injection |
| flow | 1.4 mL/min |
| column temperature | 45° C. |
| gradient | 0.0-1.0 min 15% B → 95% B<br>1.0-1.1 min 95% B<br>Stop time: 1.3 min |
| | Method 7 |
| HPLC | Agilent 1100/1200 Series |
| MS | Agilent LC/MSD SL |
| column | Waters X-Bridge BEH C18, 2.5 μm, 2.1 × 30 mm XP |
| eluent | A: 5 mM NH$_4$HCO$_3$/19 mM NH$_3$ in H$_2$O;<br>B: acetonitrile (HPLC grade) |
| detection signal | MS: positive and negative mode |
| mass range | 100-1200 m/z |
| flow | 1.40 mL/min |
| column temperature | 45° C. |
| gradient | 0.00-1.00 min: 5% B → 100% B<br>1.00-1.37 min: 100% B<br>1.37-1.40 min: 100% B → 5% B |
| | Method 8 |
| HPLC | Agilent RRLC |
| MS | Agilent Technologies -6130 Quadrupole LC/MS |
| MSD signal settings | Scan positive 70-1200, Scan negative 70-1200 |
| column | X-Bridge C18, 4.6 × 75 mm, 3.5 μm |
| eluent | A: 10 mM NH$_4$HCO$_3$ in H$_2$O,<br>B: acetonitrile (HPLC grade) |
| detection signal | UV 215/254 nm (Bandwidth 4, Reference off) |
| spectrum | Range: 200-400 nm; step: 2 nm |
| peak width | >0.1 min (2.0 s response time) (2.5 Hz) |
| injection | 4.0 μL injection with needle wash |
| flow rate | 2.0 mL/min |
| column temperature | 35° C. |
| gradient | 0.0-0.2 min: 10% B<br>0.2-2.5 min: 10% → 75% B<br>2.5-3.0 min: 75% → 100% B<br>3.0-4.8 min: 100% B<br>4.8-5.0 min: 100% → 10% B |
| | Method 9 |
| HPLC | Waters Acquity-UPLC-SQ Detector-2 |
| column | AQUITY UPLC BEH C18 1.7 μm, 2.1 × 50 mm |
| eluent | A: 0.07% formic acid in acetonitrile,<br>B: 0.07% formic acid in water |
| flow rate | 0.6 mL/min |
| column temperature | 35° C. |
| gradient | 0.0-0.3 min: 97% B<br>0.3-2.2 min: 97% → 2% B<br>2.2-4.5 min: 2% B<br>4.5-4.51 min: 2% → 97% B |
| | Method 10 |
| HPLC | Thermo Scientific, Dionex Ultimate-3000 |
| MS | Thermo Scientific LCQ FLEET (Ion Trap) |
| MSD signal settings | ESI MODE, Scan Pos & Neg 100-1500 |
| column | X-Bridge C18 2.5 μm, 4.6 × 50 mm |
| eluent | A: 10 mM NH$_4$HCO$_3$ in H$_2$O,<br>B: acetonitrile (HPLC grade) |
| detection signal | Diode Array |
| spectrum | Range: 200-400 nm; Detection Signal: 215 & 254 nm |
| flow rate | 1.0 mL/min |
| column temperature | 35° C. |
| gradient | 0.0-0.80 min: 5% B<br>0.80-4.0 min: 5% → 75% B<br>4.0-5.0 min: 75% → 98% B<br>5.0-6.80 min: 98% B<br>6.80-8.0 min: 98% → 5% B |
| | Method 11 |
| HPLC -MS | Waters Acquity-Binary Solvent Manager-UPLC-SQ Detector-2 |
| MSD signal settings | Scan pos & Neg 100-1500 |
| column | AQUITY UPLC BEH C18 1.7 μm, 2.1 × 50 mm |
| eluent | A: 0.07% formic acid in acetonitrile,<br>B: 0.07% formic acid in water |
| detection signal | Diode Array |
| spectrum | Range: 200-400 nm; resolution: 1.2 nm |
| injection | 0.5 μL standard injection |
| flow rate | 0.6 mL/min |
| column temperature | 35° C. |
| gradient | 0.0-0.40 min: 97% B<br>0.40-2.50 min: 97% → 2% B<br>2.50-3.40 min: 2% B<br>3.40-3.50 min: 2% → 97% B<br>3.50-4.0 min: 97% B |

Synthesis of Compounds C

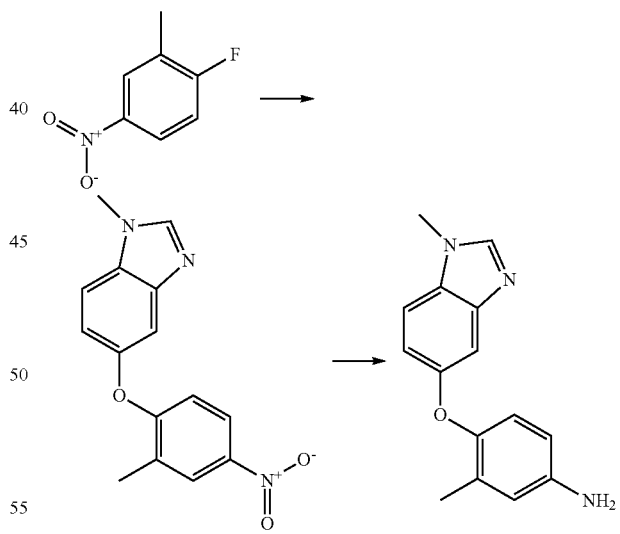

Synthesis of B-01

1-Methyl-1H-benzo[d]imidazol-5-ol (500 mg, 3.38 mmol), 1-fluoro-2-methyl-4-nitrobenzene (681 mg, 4.39 mmol) and potassium carbonate (1.16 g, 8.44 mmol) in DMF (5 mL) are stirred at 80° C. for 6 h. The reaction mixture is concentrated. The crude product is purified by column chromatography (SiO$_2$, cyclohexane/ethyl acetate gradient). Compounds B-02-B-09 (Table 1) are synthesized analogously to the procedure shown above.

TABLE 1

| Example Number | Structure | $t_{Ret}$ [min] | $[M + H]^+$ | Method |
|---|---|---|---|---|
| B-01 | 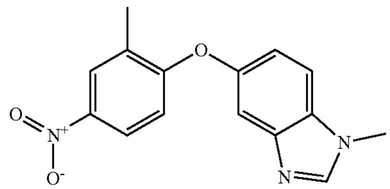 [SMILES: Cc1cc([N+](=O)[O-])ccc1Oc1ccc2c(c1)ncn2C] | 1.25 | 284 | 5 |
| B-02 | 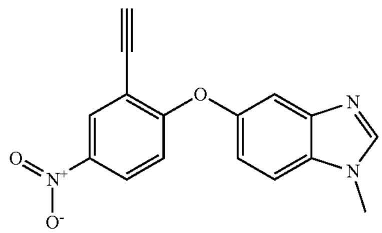 [SMILES: C#Cc1cc([N+](=O)[O-])ccc1Oc1ccc2c(c1)ncn2C] | 0.41 | 294 | 2 |
| B-03 | 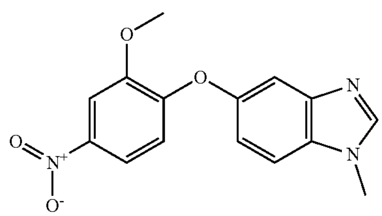 [SMILES: COc1cc([N+](=O)[O-])ccc1Oc1ccc2c(c1)ncn2C] | 1.09 | 300 | 5 |
| B-04 | 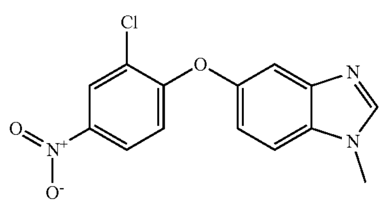 [SMILES: Cn1cnc2cc(Oc3ccc([N+](=O)[O-])cc3Cl)ccc21] | 2.66 | 304 | 8 |
| B-05 | 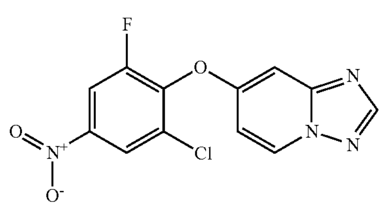 [SMILES: O=[N+]([O-])c1cc(F)c(Oc2ccn3ncnc3c2)c(Cl)c1] | 0.50 | 308 | 3 |
| B-06 | 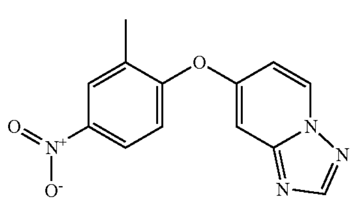 [SMILES: Cc1cc([N+](=O)[O-])ccc1Oc1ccn2ncnc2c1] | 0.50 | 271 | 3 |
| B-07 | 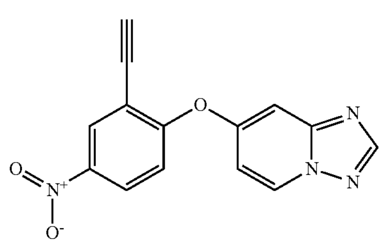 [SMILES: C#Cc1cc([N+](=O)[O-])ccc1Oc1ccn2ncnc2c1] | 2.35 | 281 | 9 |

TABLE 1-continued

| Example Number | Structure | $t_{Ret}$ [min] | $[M + H]^+$ | Method |
|---|---|---|---|---|
| B-08 | 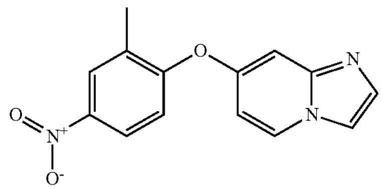 [SMILES: Cc1cc([N+](=O)[O-])ccc1Oc1ccn2ccnc2c1] | 1.15 | 270 | 5 |
| B-09 | 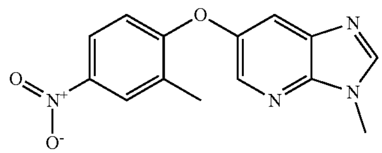 [SMILES: Cc1cc([N+](=O)[O-])ccc1Oc1cnc2c(c1)ncn2C] | 1.13 | 285 | 5 |

Synthesis of C-01 and C-05

Method 1—Synthesis of C-01

B-01 (950 mg, 3.35 mmol) and 10% Pd/C (100 mg) in ethanol (10 mL)/THF (10 mL) are stirred under a hydrogen atmosphere (3 bar) for 24 h at a temperature of 18-25° C. The reaction mixture is filtered and concentrated in vacuo.

Compounds C-03 and C-06-C-08 (Table 2) are synthesized analogously to the procedure shown above.

Method 2—Synthesis of C-05

B-05 (250 mg, 0.81 mmol) and iron (226 mg, 55.8 mmol) are suspended in ethanol and sat. aq. NH$_4$Cl solution. The resulting reaction mixture is stirred at 80° C. for 3 hours and subsequently at a temperature of 18-25° C. for 16 hours. The reaction mixture is filtered over a pad of celite and the filtrate is concentrated in vacuo. The resulting residue is used in the next synthetic step without further purification.

Compounds C-02, C-04, and C-09 (Table 2) are synthesized analogously to the procedure shown above.

TABLE 2

| Example Number | Structure | $t_{Ret}$ [min] | $[M + H]^+$ | Method |
|---|---|---|---|---|
| C-01 | 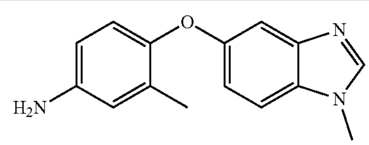 [SMILES: Cc1cc(N)ccc1Oc1ccc2c(c1)ncn2C] | 0.98 | 254 | 5 |
| C-02 | 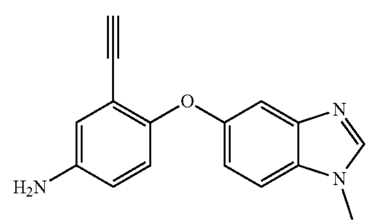 [SMILES: C#Cc1cc(N)ccc1Oc1ccc2c(c1)ncn2C] | 0.37 | 264 | 3 |
| C-03 | 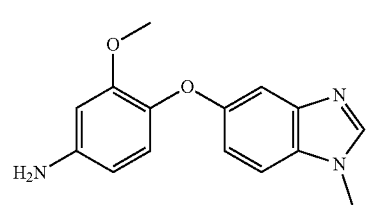 [SMILES: COc1cc(N)ccc1Oc1ccc2c(c1)ncn2C] | 0.84 | 270 | 5 |
| C-04 | 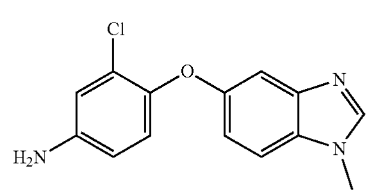 [SMILES: Cn1cnc2cc(Oc3ccc(N)cc3Cl)ccc21] | 0.43 | 274 | 3 |

TABLE 2-continued

| Example Number | Structure | $t_{Ret}$ [min] | $[M + H]^+$ | Method |
|---|---|---|---|---|
| C-05 | 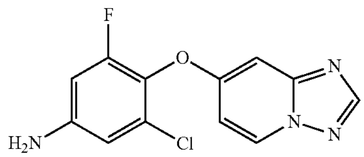 [SMILES: Nc1cc(F)c(Oc2ccn3ncnc3c2)c(Cl)c1] | 0.43 | 279 | 3 |
| C-06 | 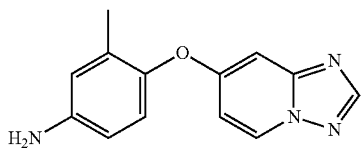 [SMILES: Cc1cc(N)ccc1Oc1ccn2ncnc2c1] | 0.86 | 241 | 5 |
| C-07 | 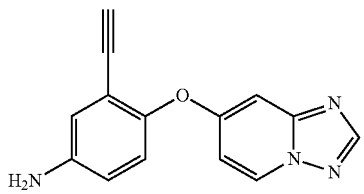 [SMILES: C#Cc1cc(N)ccc1Oc1ccn2ncnc2c1] | 1.90 | 251 | 9 |
| C-08 | 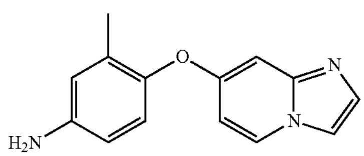 [SMILES: Cc1cc(N)ccc1Oc1ccn2ccnc2c1] | 0.93 | 240 | 5 |
| C-09 | 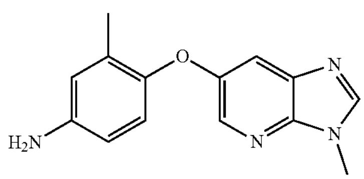 [SMILES: Cc1cc(N)ccc1Oc1cnc2c(c1)ncn2C] | 0.85 | 255 | 5 |

Synthesis of Compounds F

Synthesis of Compounds F According to General Route 1 (Scheme 2)

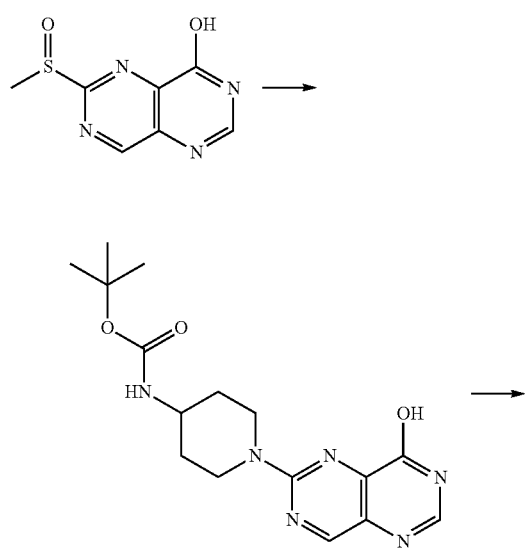

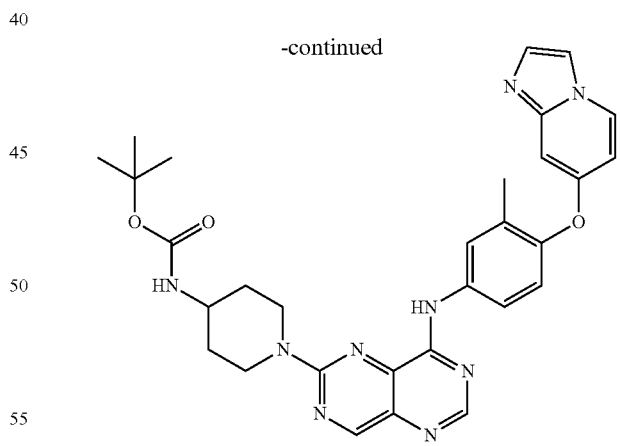

Synthesis of E-01

6-Methanesulfinyl[1,3]diazino[5,4-d]pyrimidin-4-ol (6-Methanesulfinylpyrimido[5,4-d]pyrimidin-4-ol, D, 211 mg, 1.00 mmol, prepared according to WO9732880) and tert-butyl-N-(piperidin-4-yl)carbamate (246 mg, 1.20 mmol) in dioxane (4 mL) are stirred under reflux for 16 h. The reaction mixture is concentrated under reduced pressure, and the crude product is purified by column chromatography (SiO₂, dichloromethane/methanol gradient). Compound E-02 (Table 3) is synthesized analogously to the procedure shown above.

TABLE 3

| Example Number | Structure | $t_{Ret}$ [min] | [M + H]⁺ | Method |
|---|---|---|---|---|
| E-01 | 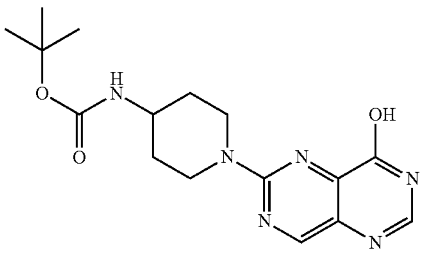 [SMILES: CC(C)(C)OC(=O)NC1CCN(c2ncc3ncnc(O)c3n2)CC1] | 0.93 | 347 | 5 |
| E-02 | 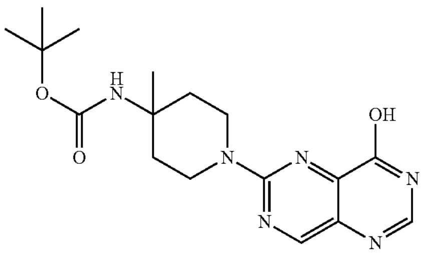 [SMILES: CC1(NC(=O)OC(C)(C)C)CCN(c2ncc3ncnc(O)c3n2)CC1] | 0.43 | 361 | 3 |

Synthesis of F-03

E-01 (200 mg, 0.55 mmol), benzotriazol-1-yloxytris(pyrrolidino)phosphonium hexafluorophosphate (441 mg, 0.83 mmol) and 1,8-diazabicyclo[5.4.0]endec-7-ene (126 mg, 0.83 mmol) in dry THF (4 mL) are stirred at a temperature of 18-25° C. for 30 minutes. C-03 (205 mg, 0.66 mmol) in dry THF (1 mL) is added, and the mixture is stirred at 70° C. for 16 h. The mixture is concentrated in vacuo, and the crude product is purified by preparative reversed phase HPLC.

Compounds F-04, F-06, and F-12 (Table 6) are synthesized analogously to the procedure shown above.

Synthesis of Compounds F According to General Route 2 (Scheme 3)

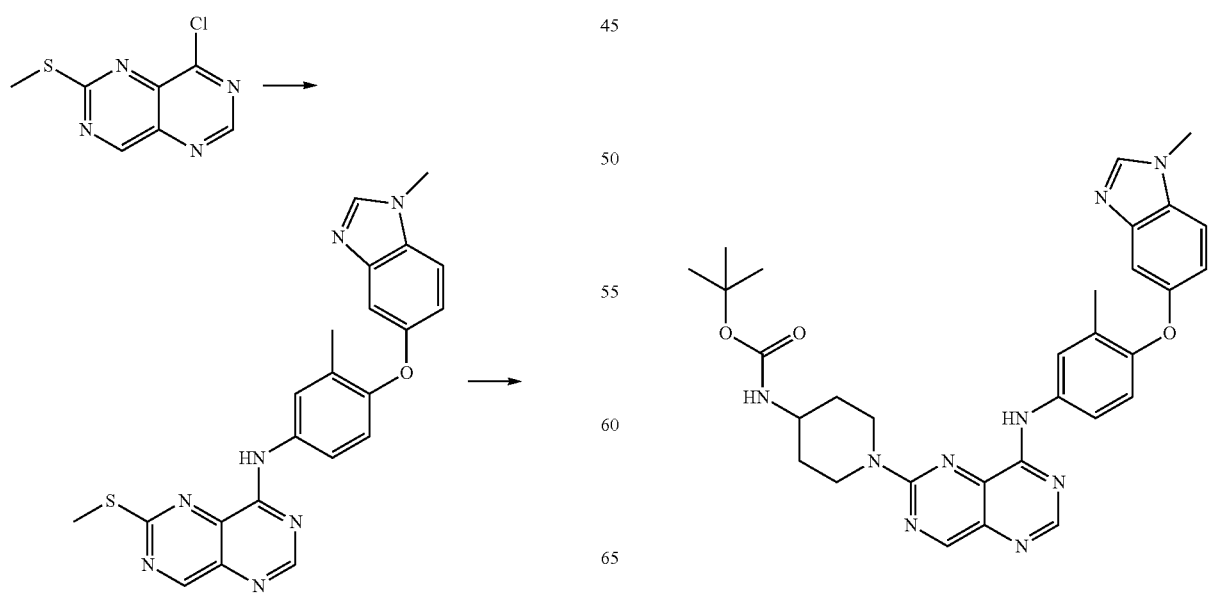

Synthesis of H-01

8-Chloro-2-(methylthio)pyrimido[5,4-d]pyrimidine (500 mg, 1.97 mmol) and C-01 (492 mg, 1.97 mmol) in isopropanol (10 mL) are stirred at 50° C. for 3 h. The precipitate is collected by filtration, and the crude product is purified by column chromatography (SiO$_2$, dichloromethane/methanol gradient) to give the product H-01.

Compounds H-02-H-06 (Table 4) are synthesized analogously to the procedure shown above. The product may also be isolated by partitioning the reaction mixture between organic solvent and aqueous layer, reducing the organic layer in vacuo, and column purification of the crude product.

TABLE 4

| Example Number | Structure | $t_{Ret}$ [min] | [M + H]$^+$ | Method |
|---|---|---|---|---|
| H-01 | 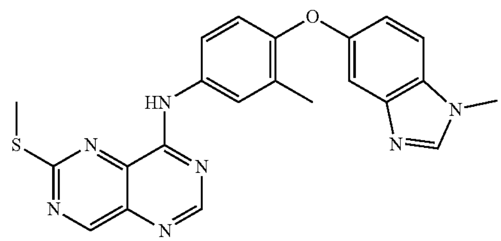 [SMILES: CSc1ncc2ncnc(Nc3ccc(Oc4ccc5c(c4)ncn5C)c(C)c3)c2n1] | 0.45 | 430 | 3 |
| H-02 | 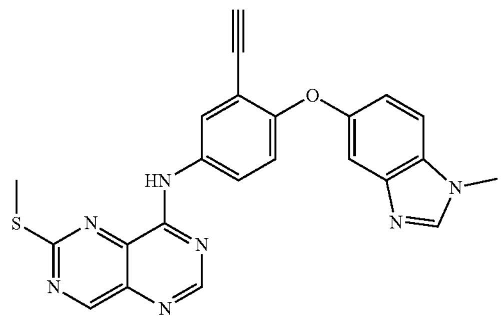 [SMILES: C#Cc1cc(Nc2ncnc3cnc(SC)nc23)ccc1Oc1ccc2c(c1)ncn2C] | 2.47 | 441 | 9 |
| H-03 | 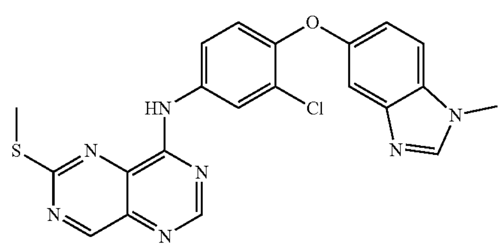 [SMILES: CSc1ncc2ncnc(Nc3ccc(Oc4ccc5c(c4)ncn5C)c(Cl)c3)c2n1] | 4.39 | 450 | 10 |
| H-04 | 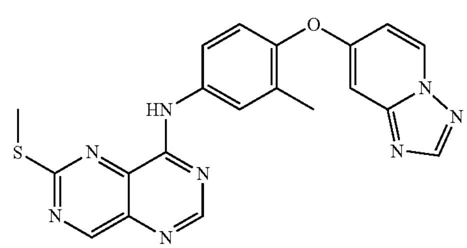 [SMILES: CSc1ncc2ncnc(Nc3ccc(Oc4ccn5ncnc5c4)c(C)c3)c2n1] | 0.59 | 417 | 3 |
| H-05 | 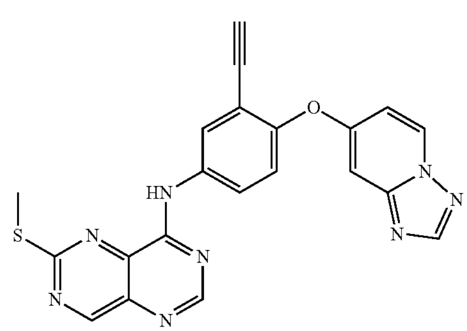 [SMILES: C#Cc1cc(Nc2ncnc3cnc(SC)nc23)ccc1Oc1ccn2ncnc2c1] | 1.82 | 427 | 11 |

TABLE 4-continued

| Example Number | Structure | $t_{Ret}$ [min] | $[M + H]^+$ | Method |
|---|---|---|---|---|
| H-06 | 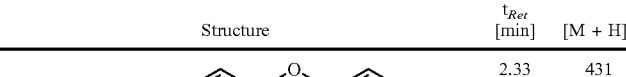 | 2.33 | 431 | 9 |

Synthesis of J-01

To H-01 (860 mg, 1.80 mmol) in dichloromethane (30 mL), m-chloroperbenzoic acid (77%, 444 mg, 1.98 mmol) is added at 5° C., and the reaction mixture is stirred at a temperature of 18-25° C. for 2 h. Sat. aq. NaHCO₃ solution (200 mL) is added, and the aqueous layer is extracted with dichloromethane several times. The combined organic layer is washed with water, dried (Mg₂SO₄), filtered, and concentrated in vacuo. The crude product J-01 is used in the next step without further purification.

Compounds J-02-J-06 (Table 5) are synthesized analogously to the procedure shown above.

TABLE 5

| Example Number | Structure | $t_{Ret}$ [min] | $[M + H]^+$ | Method |
|---|---|---|---|---|
| J-01 | 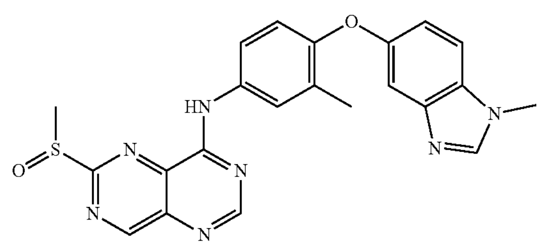 [SMILES: Cc1cc(Nc2ncnc3cnc(S(C)=O)nc23)ccc1Oc1ccc2c(c1)ncn2C] | 0.46 | 446 | 3 |
| J-02 | 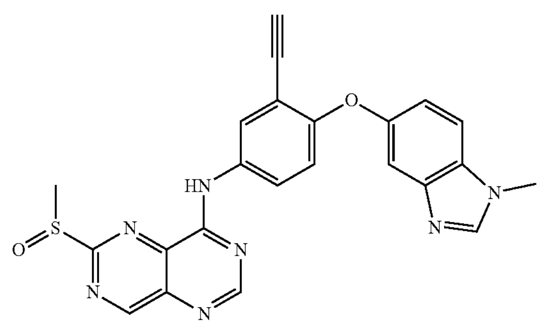 [SMILES: C#Cc1cc(Nc2ncnc3cnc(S(C)=O)nc23)ccc1Oc1ccc2c(c1)ncn2C] | 1.35 | 456 | 11 |
| J-03 | 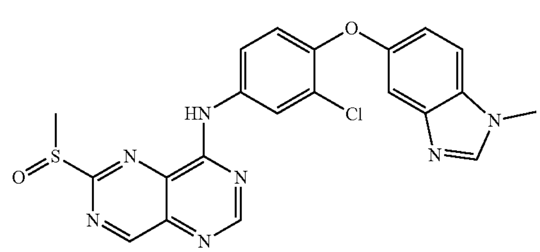 [SMILES: Cn1cnc2cc(Oc3ccc(Nc4ncnc5cnc(S(C)=O)nc45)cc3Cl)ccc21] | 2.29 | 466 | 8 |

TABLE 5-continued

| Example Number | Structure | $t_{Ret}$ [min] | $[M + H]^+$ | Method |
|---|---|---|---|---|
| J-04 | 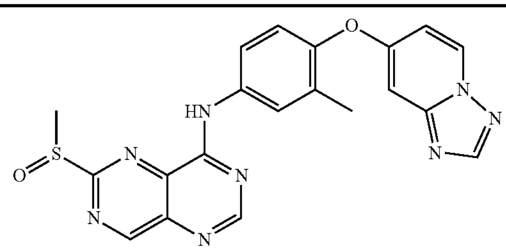 | 0.94 | 433 | 5 |
| J-05 | 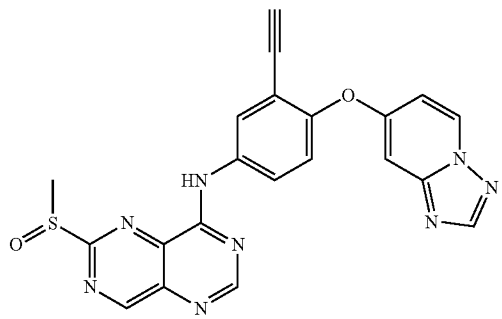 [SMILES: C#Cc1cc(Nc2ncnc3cnc(S(C)=O)nc23)ccc1Oc1ccn2ncnc2c1] | 4.78 | 443 | 9 |
| J-06 | 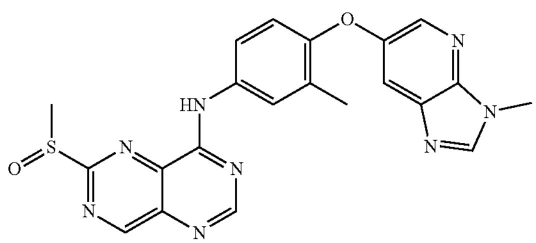 [SMILES: Cc1cc(Nc2ncnc3cnc(S(C)=O)nc23)ccc1Oc1cnc2c(c1)ncn2C] | 1.41 | 447 | 11 |

Synthesis of F-01

J-01 (5.42 g, 9.74 mmol), tert-butyl-N-(piperidin-4-yl) carbamate (2.39 g, 11.7 mmol) and N-ethyl-diisopropylamine (2.51 g, 19.4 mmol) in DMF (50 mL) are stirred at 60° C. for 16 h. The reaction mixture concentrated in vacuo, and the crude product is used without further purification for the next step.

Compounds F-02, F-05, F-07-F-11, and F-13-F-19 (Table 6) are synthesized analogously to the procedure shown above.

TABLE 6

| Example Number | Structure | $t_{Ret}$ [min] | $[M + H]^+$ | Method |
|---|---|---|---|---|
| F-01 | 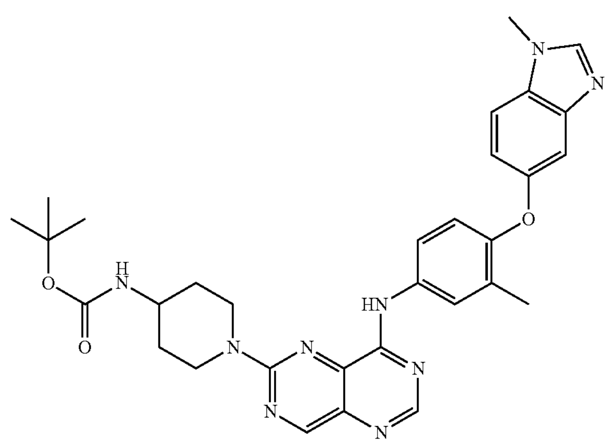 [SMILES: Cc1cc(Nc2ncnc3cnc(N4CCC(NC(=O)OC(C)(C)C)CC4)nc23)ccc1Oc1ccc2c(c1)ncn2C] | 1.43 | 582 | 5 |

TABLE 6-continued
| Example Number | Structure | $t_{Ret}$ [min] | [M + H]⁺ | Method |
|---|---|---|---|---|
| F-02 | 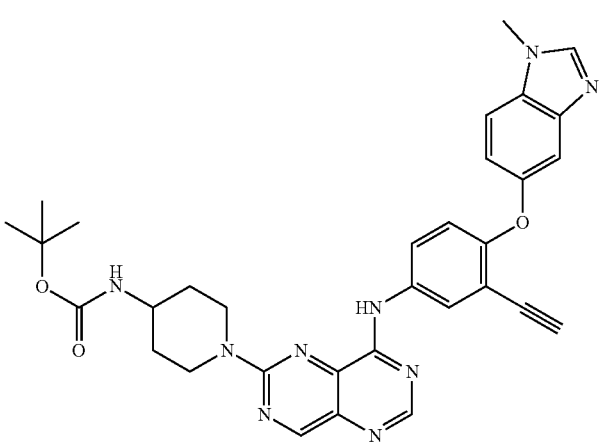 [SMILES: C#Cc1cc(Nc2ncnc3cnc(N4CCC(NC(=O)OC(C)(C)C)CC4)nc23)ccc1Oc1ccc2c(c1)ncn2C] | 0.70 | 592 | 1 |
| F-03 | 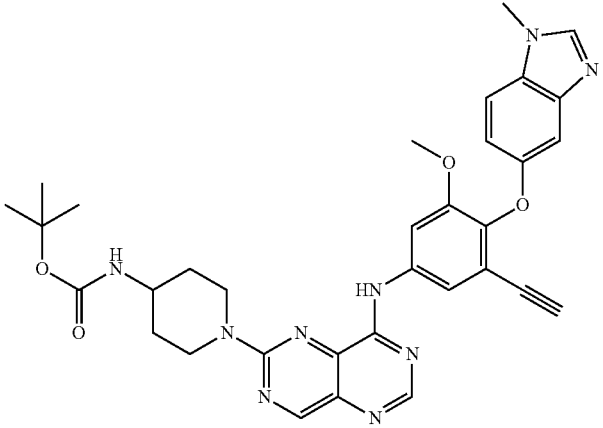 [SMILES: C#Cc1cc(Nc2ncnc3cnc(N4CCC(NC(=O)OC(C)(C)C)CC4)nc23)cc(OC)c1Oc1ccc2c(c1)ncn2C] | 1.29 | 598 | 5 |
| F-04 | 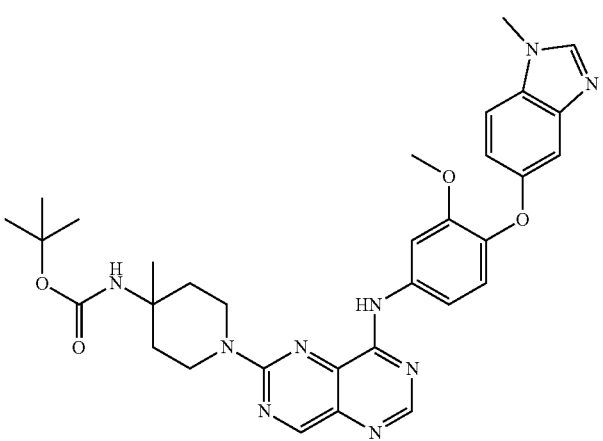 [SMILES: COc1cc(Nc2ncnc3cnc(N4CCC(C)(NC(=O)OC(C)(C)C)CC4)nc23)ccc1Oc1ccc2c(c1)ncn2C] | 1.43 | 612 | 5 |

TABLE 6-continued

| Example Number | Structure | $t_{Ret}$ [min] | [M + H]⁺ | Method |
|---|---|---|---|---|
| F-05 | 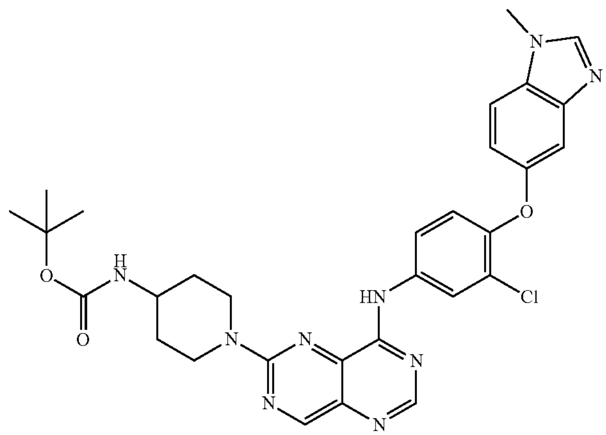 [SMILES: Cn1cnc2cc(Oc3ccc(Nc4ncnc5cnc(N6CCC(NC(=O)OC(C)(C)C)CC6)nc45)cc3Cl)ccc21] | 0.78 | 602 | 6 |
| F-06 | 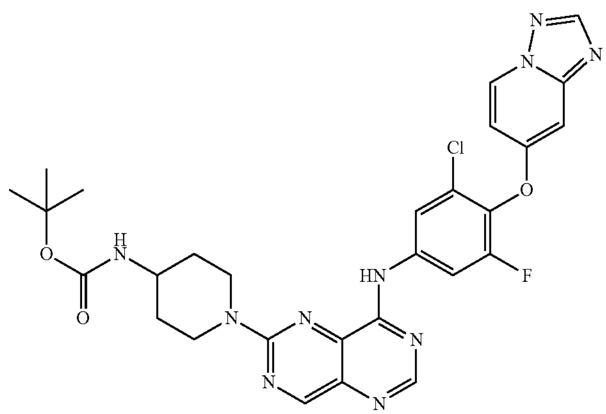 [SMILES: CC(C)(C)OC(=O)NC1CCN(c2ncc3ncnc(Nc4cc(F)c(Oc5ccn6ncnc6c5)c(Cl)c4)c3n2)CC1] | 0.75 | 607 | 6 |
| F-07 | 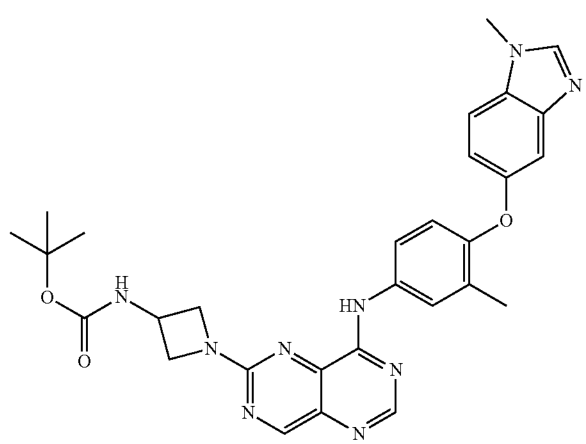 [SMILES: Cc1cc(Nc2ncnc3cnc(N4CC(NC(=O)OC(C)(C)C)C4)nc23)ccc1Oc1ccc2c(c1)ncn2C] | 0.65 | 554 | 3 |

TABLE 6-continued

| Example Number | Structure | $t_{Ret}$ [min] | [M + H]⁺ | Method |
|---|---|---|---|---|
| F-08 | 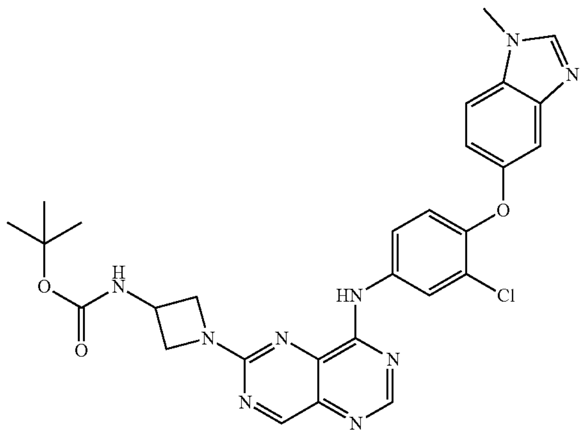 [SMILES: Cn1cnc2cc(Oc3ccc(Nc4ncnc5cnc(N6CC(NC(=O)OC(C)(C)C)C6)nc45)cc3Cl)ccc21] | 0.73 | 574 | 3 |
| F-09 | 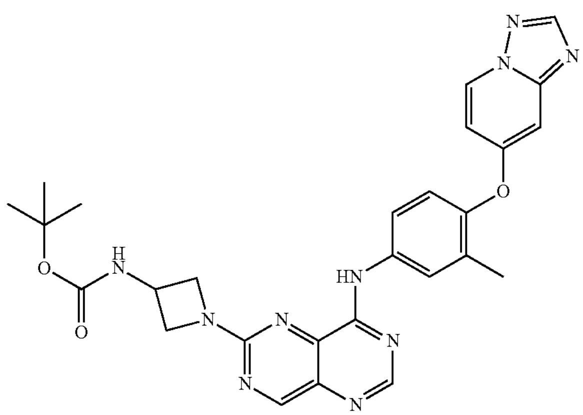 [SMILES: Cc1cc(Nc2ncnc3cnc(N4CC(NC(=O)OC(C)(C)C)C4)nc23)ccc1Oc1ccn2ncnc2c1] | 1.27 | 541 | 5 |
| F-10 | 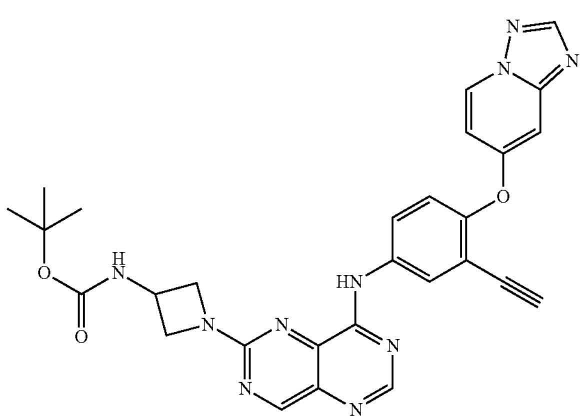 [SMILES: C#Cc1cc(Nc2ncnc3cnc(N4CC(NC(=O)OC(C)(C)C)C4)nc23)ccc1Oc1ccn2ncnc2c1] | 0.65 | 551 | 6 |

TABLE 6-continued
| Example Number | Structure | $t_{Ret}$ [min] | $[M + H]^+$ | Method |
|---|---|---|---|---|
| F-11 | 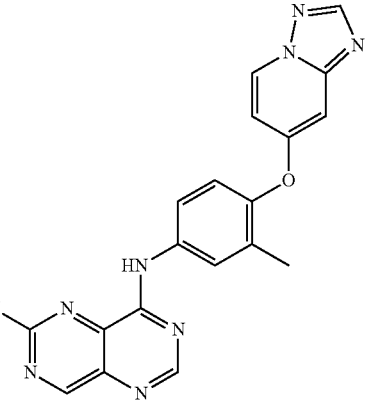 | 0.69 | 569 | 3 |
| F-12 | 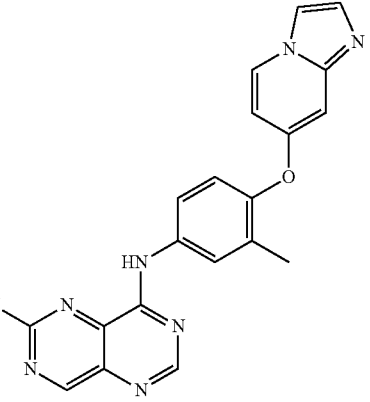 | 1.39 | 568 | 5 |
| F-13 | 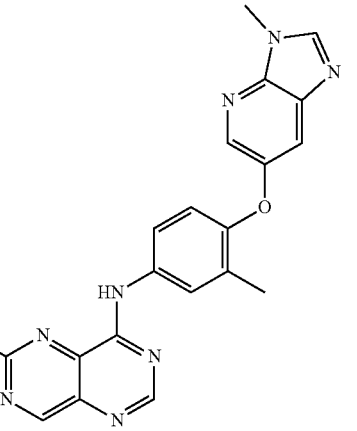 | 0.89 | 555 | 7 |

TABLE 6-continued

| Example Number | Structure | $t_{Ret}$ [min] | $[M + H]^+$ | Method |
|---|---|---|---|---|
| F-14 | 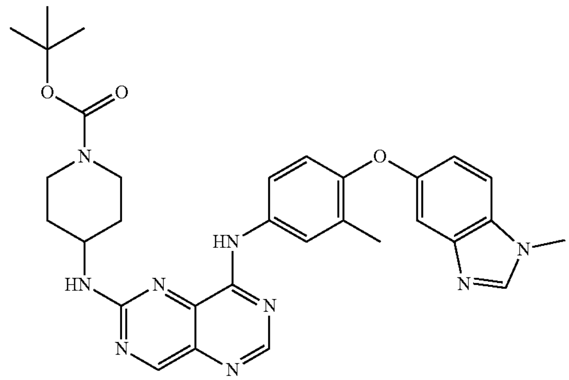 [SMILES: Cc1cc(Nc2ncnc3cnc(NC4CCN(C(=O)OC(C)(C)C)CC4)nc23)ccc1Oc1ccc2c(c1)ncn2C] | 0.75 | 582 | 6 |
| F-15 | 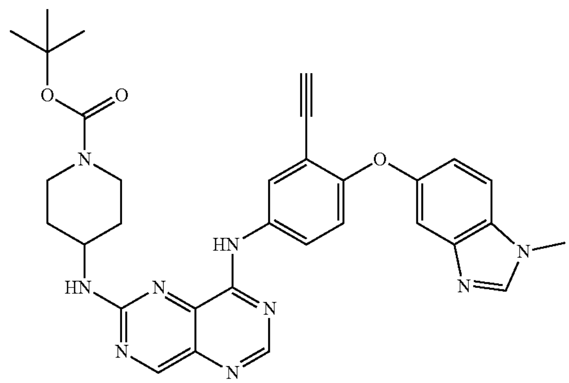 [SMILES: C#Cc1cc(Nc2ncnc3cnc(NC4CCN(C(=O)OC(C)(C)C)CC4)nc23)ccc1Oc1ccc2c(c1)ncn2C] | 0.60 | 592 | 4 |
| F-16 | 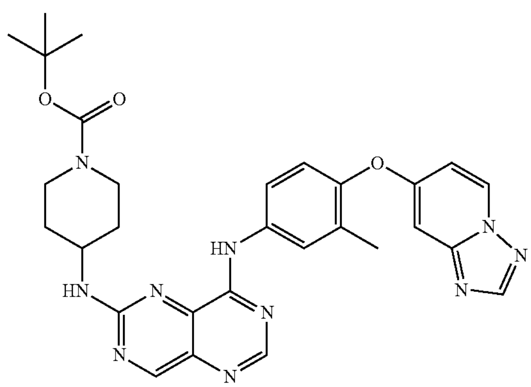 [SMILES: Cc1cc(Nc2ncnc3cnc(NC4CCN(C(=O)OC(C)(C)C)CC4)nc23)ccc1Oc1ccn2ncnc2c1] | 0.69 | 569 | 1 |
| F-17 | 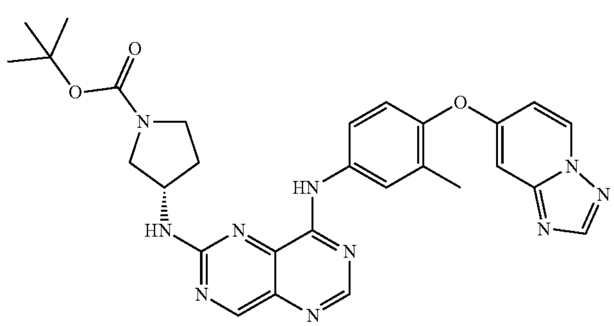 [SMILES: Cc1cc(Nc2ncnc3cnc(N[C@H]4CCN(C(=O)OC(C)(C)C)C4)nc23)ccc1Oc1ccn2ncnc2c1] | 0.65 | 555 | 1 |

TABLE 6-continued

| Example Number | Structure | $t_{Ret}$ [min] | [M + H]⁺ | Method |
|---|---|---|---|---|
| F-18 | 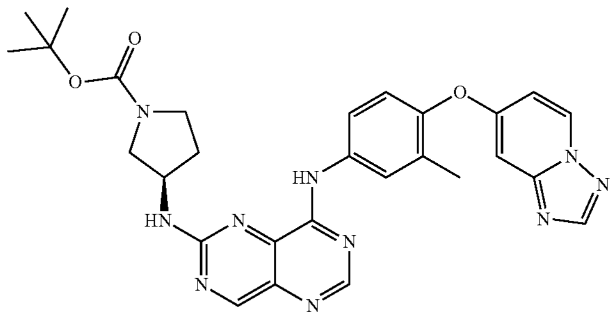 [SMILES: Cc1cc(Nc2ncnc3cnc(N[C@@H]4CCN(C(=O)OC(C)(C)C)C4)nc23)ccc1Oc1ccn2ncnc2c1] | 0.65 | 555 | 1 |
| F-19 | 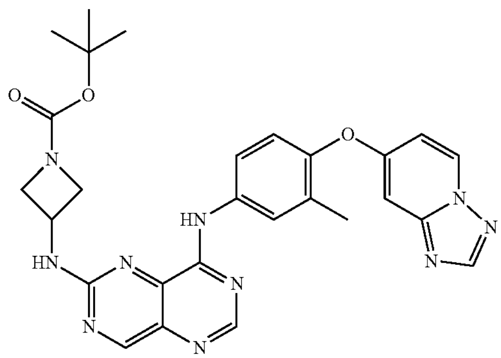 [SMILES: Cc1cc(Nc2ncnc3cnc(NC4CN(C(=O)OC(C)(C)C)C4)nc23)ccc1Oc1ccn2ncnc2c1] | 0.61 | 541 | 6 |

Synthesis of I-01-I-19

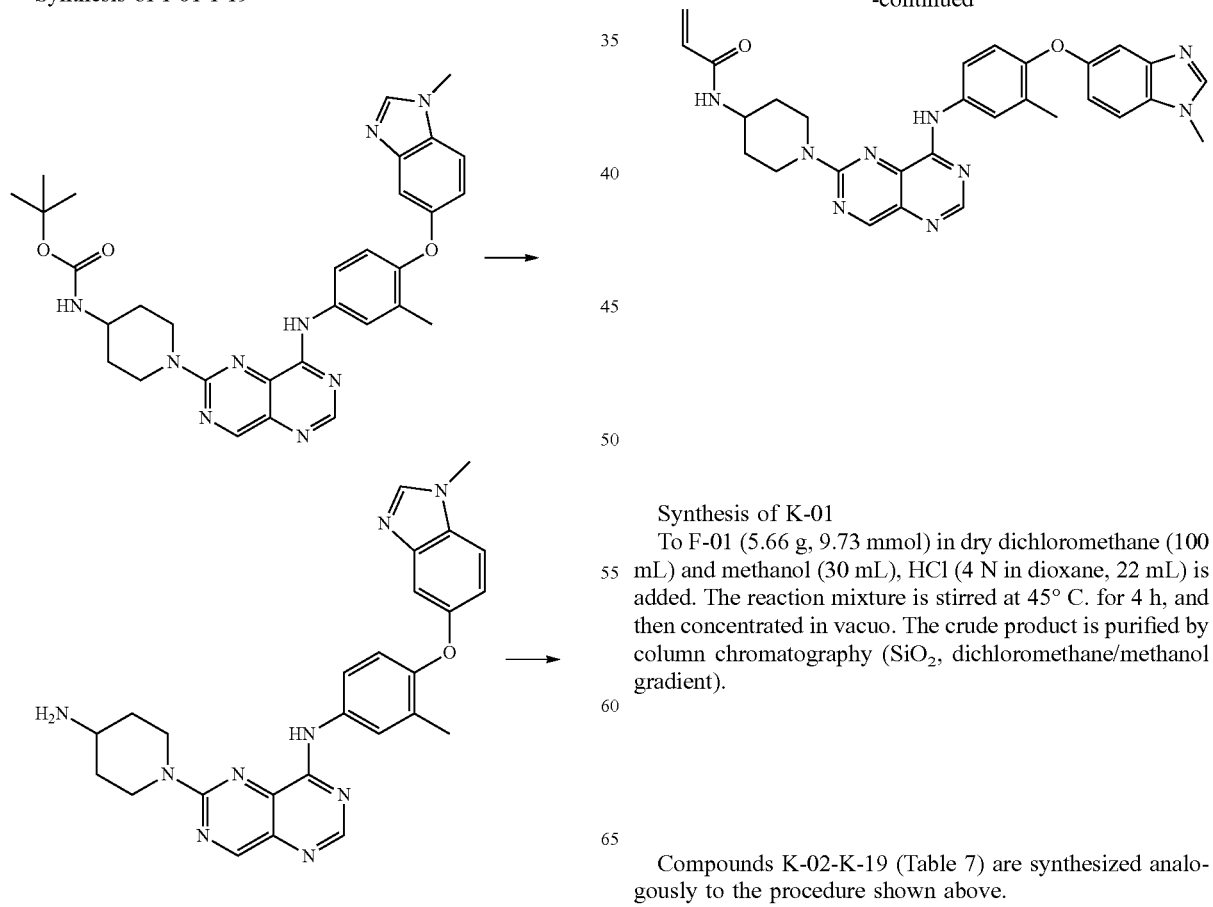

Synthesis of K-01

To F-01 (5.66 g, 9.73 mmol) in dry dichloromethane (100 mL) and methanol (30 mL), HCl (4 N in dioxane, 22 mL) is added. The reaction mixture is stirred at 45° C. for 4 h, and then concentrated in vacuo. The crude product is purified by column chromatography (SiO₂, dichloromethane/methanol gradient).

Compounds K-02-K-19 (Table 7) are synthesized analogously to the procedure shown above.

TABLE 7
| Example Number | Structure | $t_{Ret}$ [min] | $[M + H]^+$ | Method |
|---|---|---|---|---|
| K-01 | 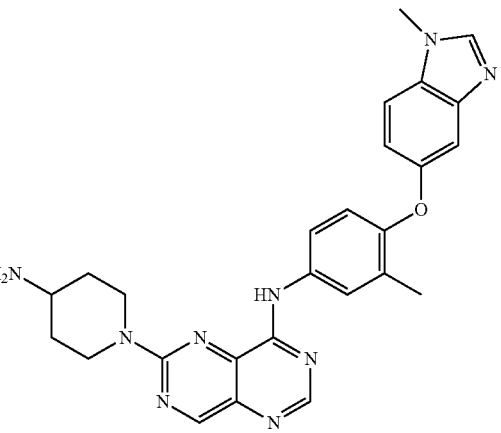 | 1.14 | 482 | 5 |
| K-02 | 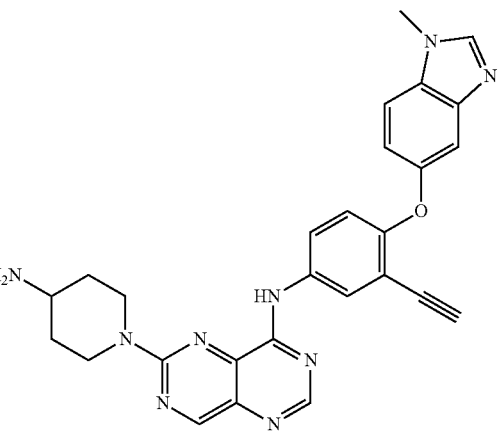 | 1.08 | 492 | 5 |
| K-03 | 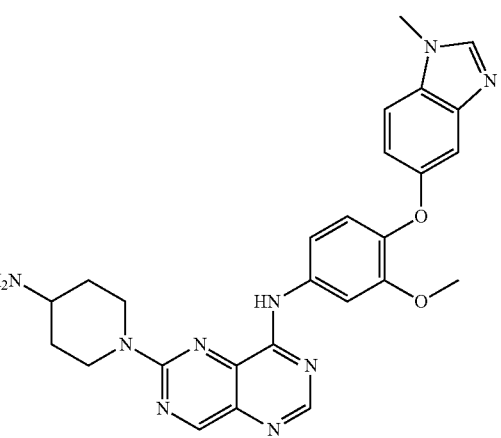 | 1.01 | 498 | 5 |

TABLE 7-continued

| Example Number | Structure | $t_{Ret}$ [min] | $[M + H]^+$ | Method |
|---|---|---|---|---|
| K-04 | 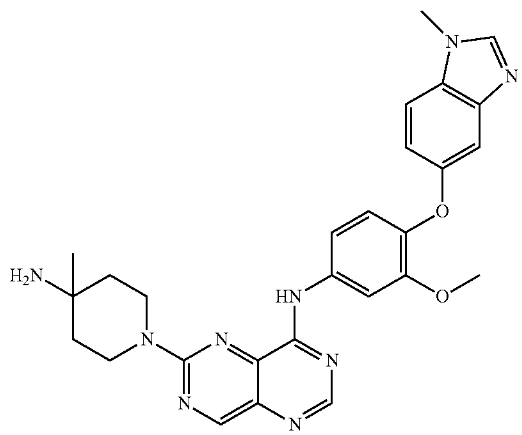 [SMILES: COc1cc(Nc2ncnc3cnc(N4CCC(C)(N)CC4)nc23)ccc1Oc1ccc2c(c1)ncn2C] | 0.49 | 512 | 3 |
| K-05 | 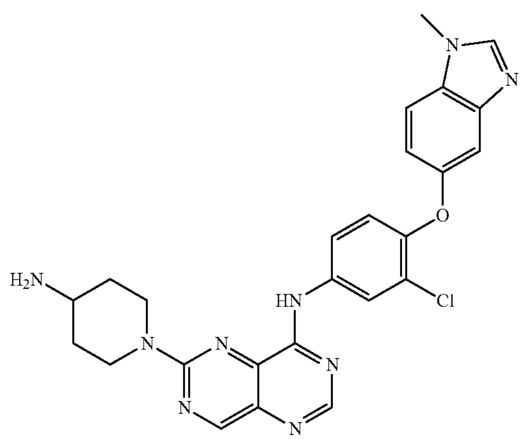 [SMILES: Cn1cnc2cc(Oc3ccc(Nc4ncnc5cnc(N6CCC(N)CC6)nc45)cc3Cl)ccc21] | 0.56 | 502 | 6 |
| K-06 | 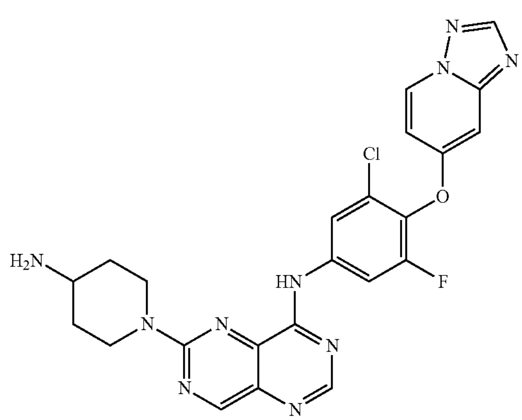 [SMILES: NC1CCN(c2ncc3ncnc(Nc4cc(F)c(Oc5ccn6ncnc6c5)c(Cl)c4)c3n2)CC1] | 1.14 | 507 | 5 |

TABLE 7-continued

| Example Number | Structure | $t_{Ret}$ [min] | $[M + H]^+$ | Method |
|---|---|---|---|---|
| K-07 | 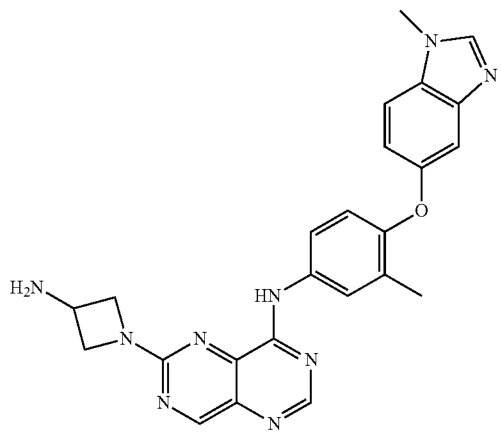 [SMILES: Cc1cc(Nc2ncnc3cnc(N4CC(N)C4)nc23)ccc1Oc1ccc2c(c1)ncn2C] | 0.45 | 454 | 3 |
| K-08 | 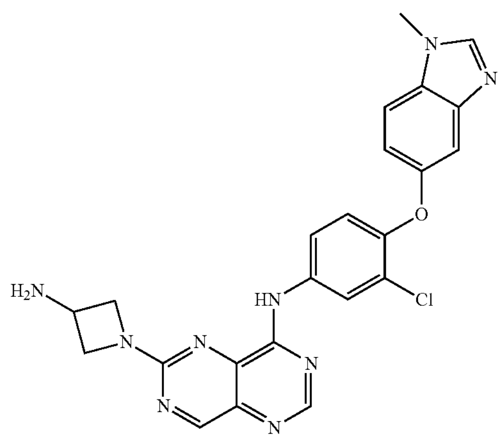 [SMILES: Cn1cnc2cc(Oc3ccc(Nc4ncnc5cnc(N6CC(N)C6)nc45)cc3Cl)ccc21] | 0.50 | 474 | 3 |
| K-09 | 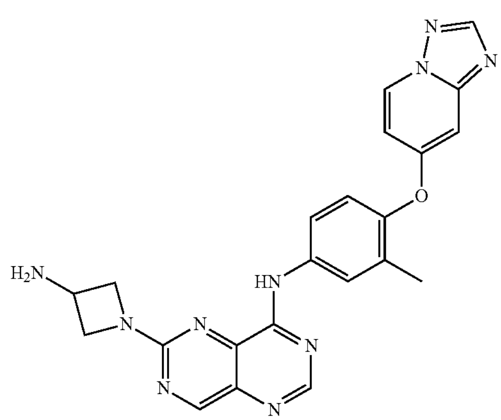 [SMILES: Cc1cc(Nc2ncnc3cnc(N4CC(N)C4)nc23)ccc1Oc1ccn2ncnc2c1] | 0.97 | 441 | 5 |

TABLE 7-continued

| Example Number | Structure | $t_{Ret}$ [min] | $[M + H]^+$ | Method |
|---|---|---|---|---|
| K-10 | 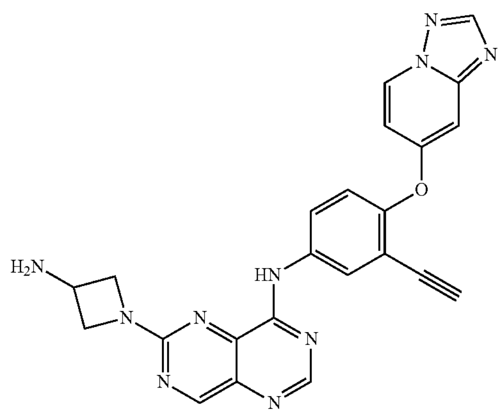 [SMILES: C#Cc1cc(Nc2ncnc3cnc(N4CC(N)C4)nc23)ccc1Oc1ccn2ncnc2c1] | 0.43 | 451 | 6 |
| K-11 | 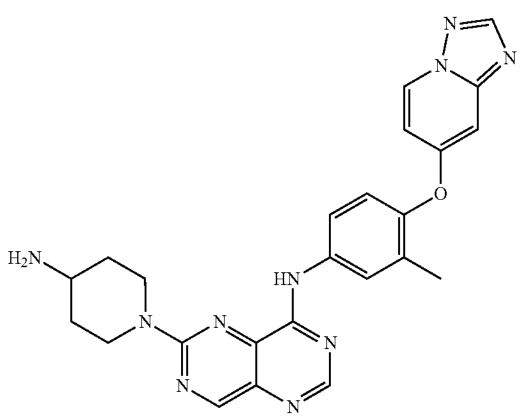 [SMILES: Cc1cc(Nc2ncnc3cnc(N4CCC(N)CC4)nc23)ccc1Oc1ccn2ncnc2c1] | 0.44 | 469 | 3 |
| K-12 | 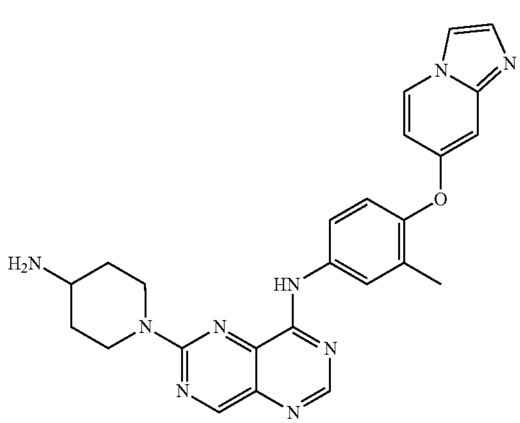 [SMILES: Cc1cc(Nc2ncnc3cnc(N4CCC(N)CC4)nc23)ccc1Oc1ccn2ccnc2c1] | 0.49 | 468 | 3 |

TABLE 7-continued

| Example Number | Structure | $t_{Ret}$ [min] | [M + H]⁺ | Method |
|---|---|---|---|---|
| K-13 | 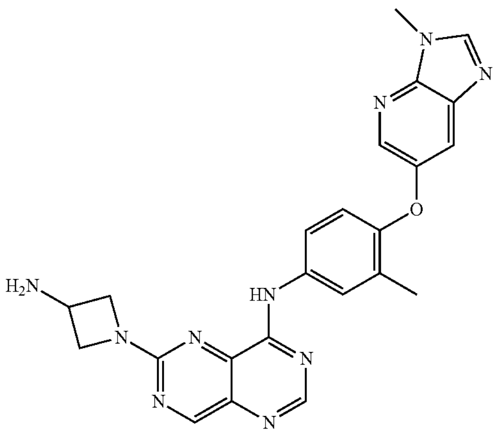 [SMILES: Cc1cc(Nc2ncnc3cnc(N4CC(N)C4)nc23)ccc1Oc1cnc2c(c1)ncn2C] | 0.95 | 455 | 5 |
| K-14 | 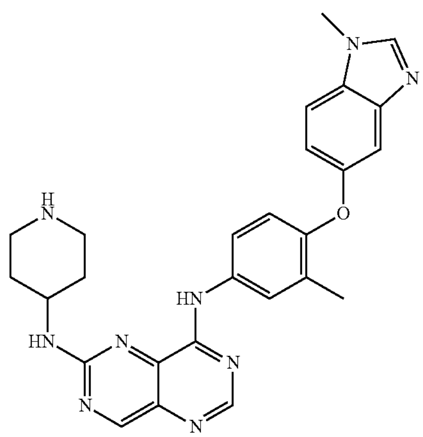 [SMILES: Cc1cc(Nc2ncnc3cnc(NC4CCNCC4)nc23)ccc1Oc1ccc2c(c1)ncn2C] | 0.50 | 482 | 3 |
| K-15 | 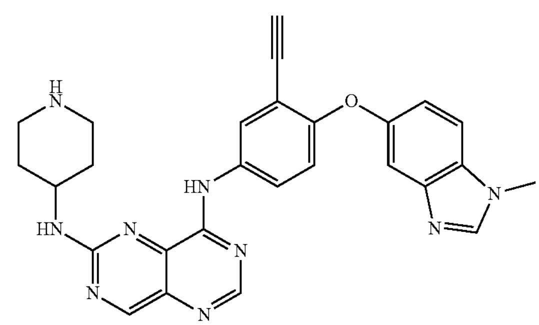 [SMILES: C#Cc1cc(Nc2ncnc3cnc(NC4CCNCC4)nc23)ccc1Oc1ccc2c(c1)ncn2C] | 0.99 | 492 | 5 |
| K-16 | 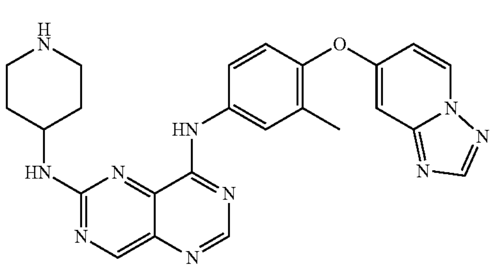 [SMILES: Cc1cc(Nc2ncnc3cnc(NC4CCNCC4)nc23)ccc1Oc1ccn2ncnc2c1] | 1.14 | 469 | 5 |

TABLE 7-continued

| Example Number | Structure | $t_{Ret}$ [min] | $[M + H]^+$ | Method |
|---|---|---|---|---|
| K-17 | 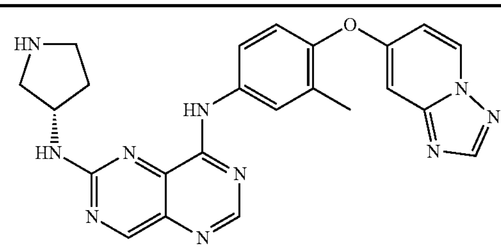 | 1.00 | 455 | 5 |
| K-18 | 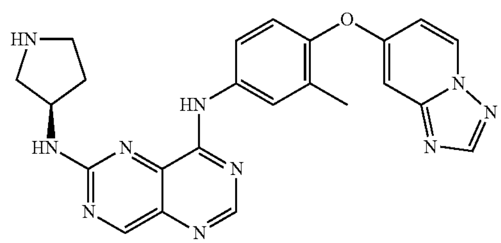 [SMILES: Cc1cc(Nc2ncnc3cnc(N[C@@H]4CCNC4)nc23)ccc1Oc1ccn2ncnc2c1] | 1.00 | 455 | 5 |
| K-19 | 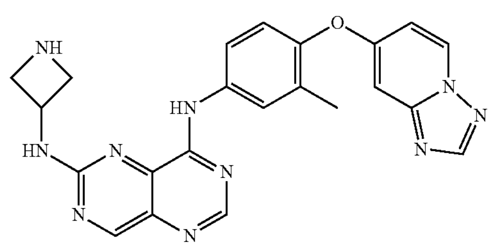 [SMILES: Cc1cc(Nc2ncnc3cnc(NC4CNC4)nc23)ccc1Oc1ccn2ncnc2c1] | 0.30 | 441 | 2 |

Synthesis of I-01

To K-01 (168 mg, 0.15 mmol) in dry dichloromethane (2 mL) acryloyl chloride (13 µL, 0.16 mmol) and diisopropylethylamine (149 µL, 0.88 mmol) are added and stirred stirred at a temperature of 18-25° C. for 1 h. The reaction mixture is concentrated in vacuo, and the crude product is purified by preparative RP-HPLC-MS.

Compounds I-02-I-19 (Table 8) are synthesized analogously to the procedure shown above.

TABLE 8

| Name | Structure | $t_{Ret}$ [min] | $[M + H]^+$ | Method |
|---|---|---|---|---|
| I-01 | 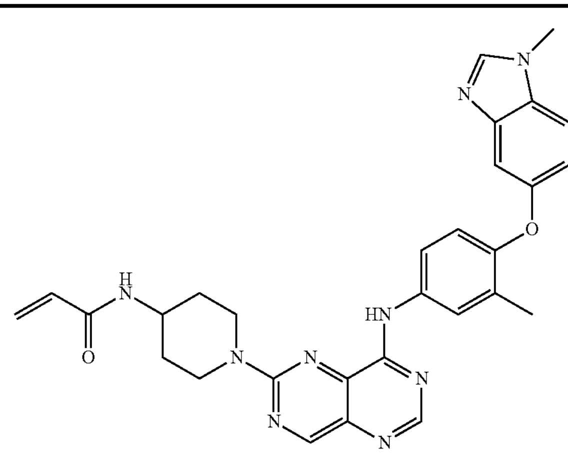 | 1.18 | 536 | 5 |

TABLE 8-continued
| Name | Structure | $t_{Ret}$ [min] | [M + H]⁺ | Method |
|---|---|---|---|---|
| I-02 | 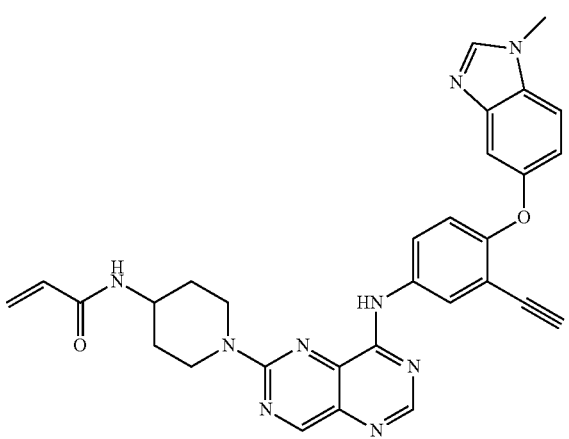 [SMILES: C#Cc1cc(Nc2ncnc3cnc(N4CCC(NC(=O)C=C)CC4)nc23)ccc1Oc1ccc2c(c1)ncn2C] | 1.13 | 546 | 5 |
| I-03 | 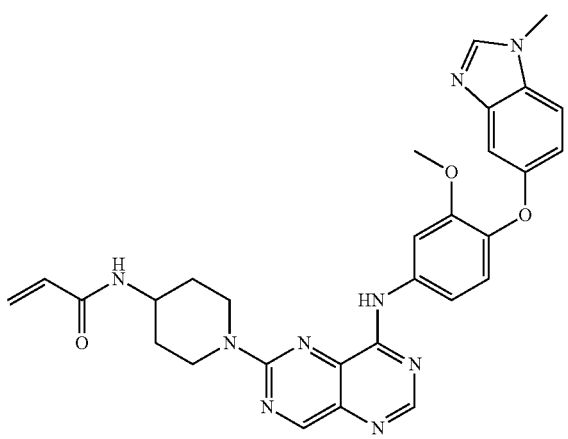 [SMILES: C=CC(=O)NC1CCN(c2ncc3ncnc(Nc4ccc(Oc5ccc6c(c5)ncn6C)c(OC)c4)c3n2)CC1] | 1.09 | 552 | 5 |
| I-04 | 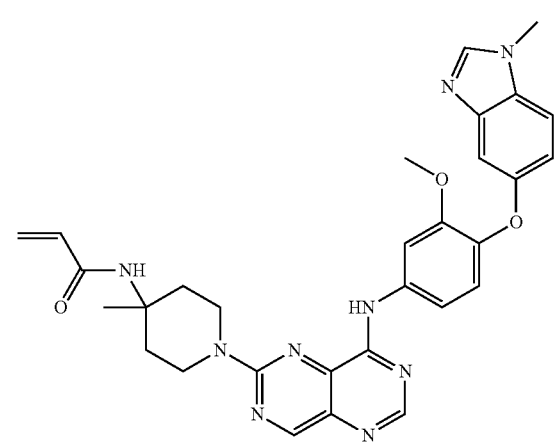 [SMILES: C=CC(=O)NC1(C)CCN(c2ncc3ncnc(Nc4ccc(Oc5ccc6c(c5)ncn6C)c(OC)c4)c3n2)CC1] | 1.20 | 566 | 5 |

TABLE 8-continued

| Name | Structure | $t_{Ret}$ [min] | $[M + H]^+$ | Method |
|---|---|---|---|---|
| I-05 | 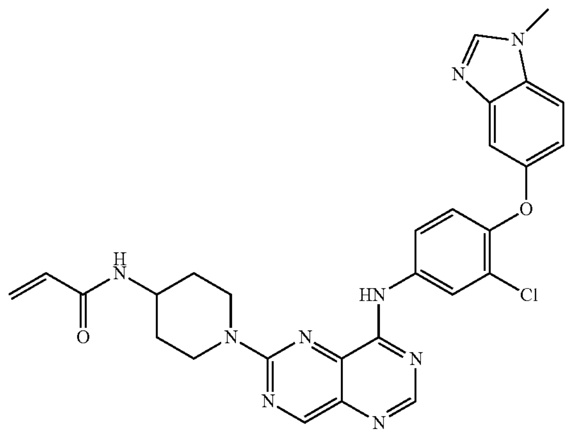 [SMILES: C=CC(=O)NC1CCN(c2ncc3ncnc(Nc4ccc(Oc5ccc6c(c5)ncn6C)c(Cl)c4)c3n2)CC1] | 1.21 | 556 | 5 |
| I-06 | 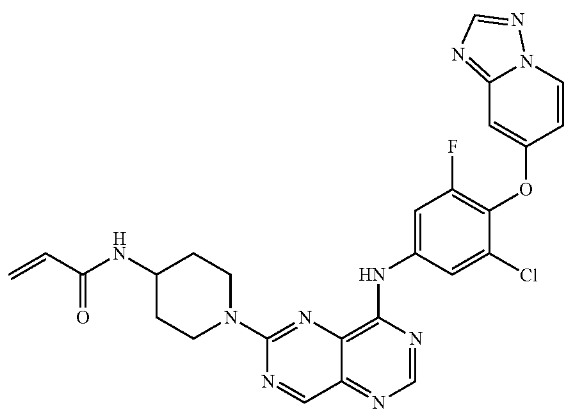 [SMILES: C=CC(=O)NC1CCN(c2ncc3ncnc(Nc4cc(F)c(Oc5ccn6ncnc6c5)c(Cl)c4)c3n2)CC1] | 1.19 | 561 | 5 |
| I-07 | 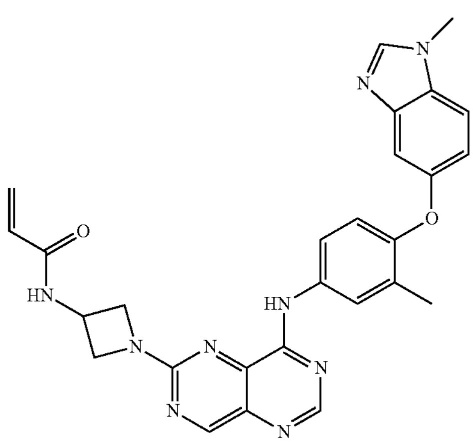 [SMILES: C=CC(=O)NC1CN(c2ncc3ncnc(Nc4ccc(Oc5ccc6c(c5)ncn6C)c(C)c4)c3n2)C1] | 1.11 | 508 | 5 |

TABLE 8-continued

| Name | Structure | t_Ret [min] | [M + H]⁺ | Method |
|---|---|---|---|---|
| I-08 | 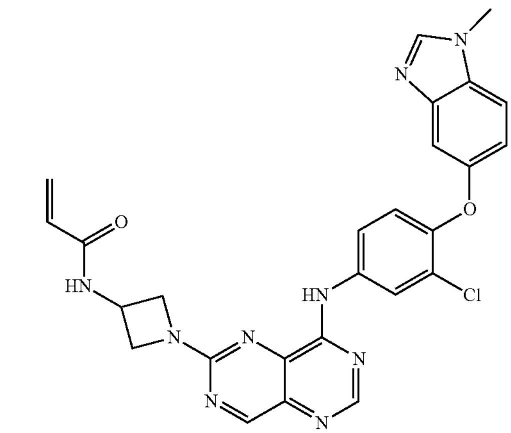 [SMILES: C=CC(=O)NC1CN(c2ncc3ncnc(Nc4ccc(Oc5ccc6c(c5)ncn6C)c(Cl)c4)c3n2)C1] | 1.13 | 528 | 5 |
| I-09 | 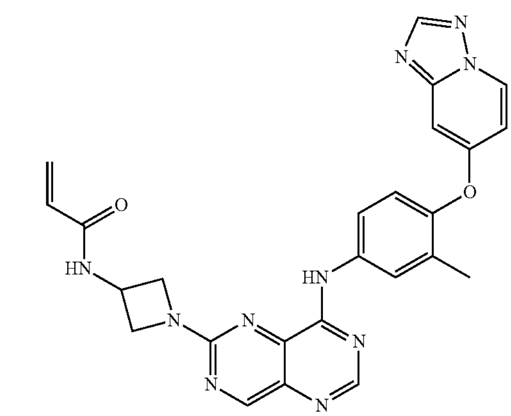 [SMILES: C=CC(=O)NC1CN(c2ncc3ncnc(Nc4ccc(Oc5ccn6ncnc6c5)c(C)c4)c3n2)C1] | 1.04 | 495 | 5 |
| I-10 | 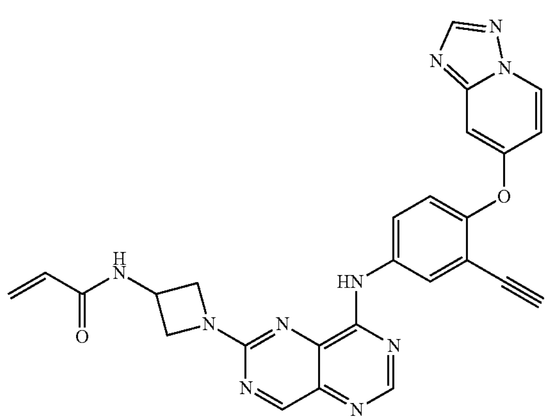 [SMILES: C#Cc1cc(Nc2ncnc3cnc(N4CC(NC(=O)C=C)C4)nc23)ccc1Oc1ccn2ncnc2c1] | 1.02 | 505 | 5 |

TABLE 8-continued

| Name | Structure | $t_{Ret}$ [min] | [M + H]⁺ | Method |
|------|-----------|-----------------|----------|--------|
| I-11 | 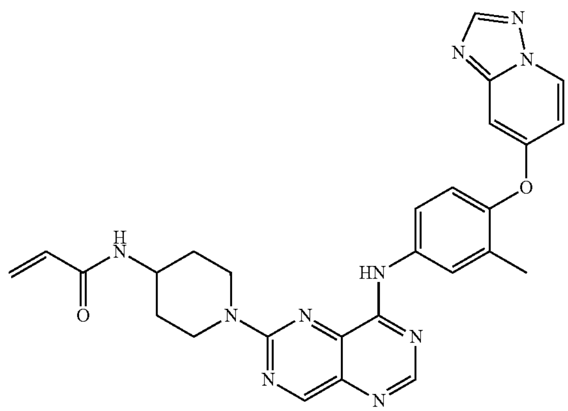 [SMILES: C=CC(=O)NC1CCN(c2ncc3ncnc(Nc4ccc(Oc5ccn6ncnc6c5)c(C)c4)c3n2)CC1] | 1.12 | 523 | 5 |
| I-12 | 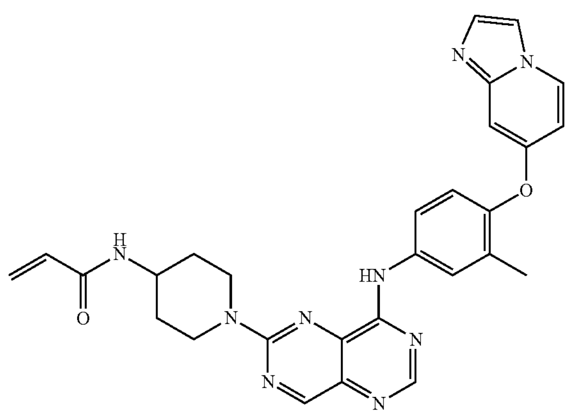 [SMILES: C=CC(=O)NC1CCN(c2ncc3ncnc(Nc4ccc(Oc5ccn6ccnc6c5)c(C)c4)c3n2)CC1] | 1.15 | 522 | 5 |
| I-13 | 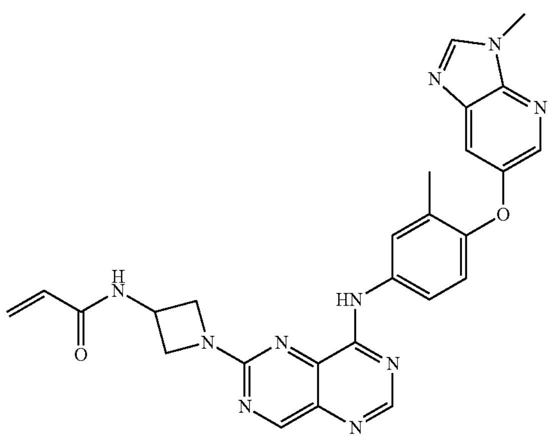 [SMILES: C=CC(=O)NC1CN(c2ncc3ncnc(Nc4ccc(Oc5cnc6c(c5)ncn6C)c(C)c4)c3n2)C1] | 1.02 | 509 | 5 |
| I-14 | 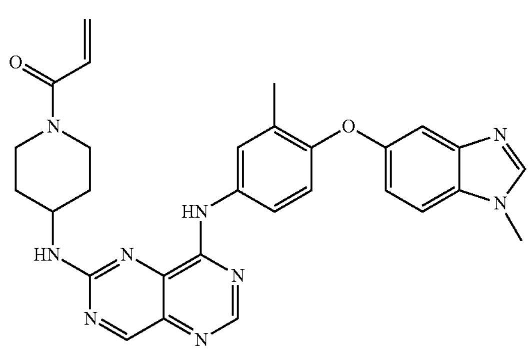 [SMILES: C=CC(=O)N1CCC(Nc2ncc3ncnc(Nc4ccc(Oc5ccc6c(c5)ncn6C)c(C)c4)c3n2)CC1] | 1.16 | 536 | 5 |

TABLE 8-continued

| Name | Structure | t_Ret [min] | [M + H]+ | Method |
|---|---|---|---|---|
| I-15 | 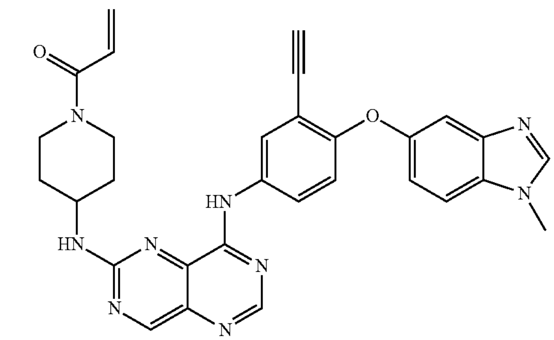 [SMILES: C#Cc1cc(Nc2ncnc3cnc(NC4CCN(C(=O)C=C)CC4)nc23)ccc1Oc1ccc2c(c1)ncn2C] | 1.10 | 546 | 5 |
| I-16 | 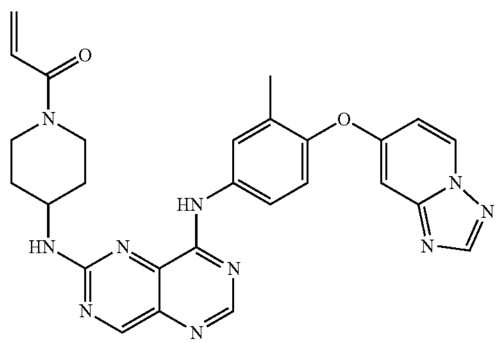 [SMILES: C=CC(=O)N1CCC(Nc2ncc3ncnc(Nc4ccc(Oc5ccn6ncnc6c5)c(C)c4)c3n2)CC1] | 1.12 | 523 | 5 |
| I-17 | 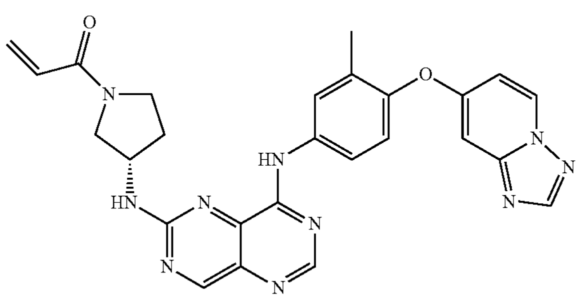 [SMILES: C=CC(=O)N1CC[C@H](Nc2ncc3ncnc(Nc4ccc(Oc5ccn6ncnc6c5)c(C)c4)c3n2)C1] | 1.09 | 509 | 5 |
| I-18 | 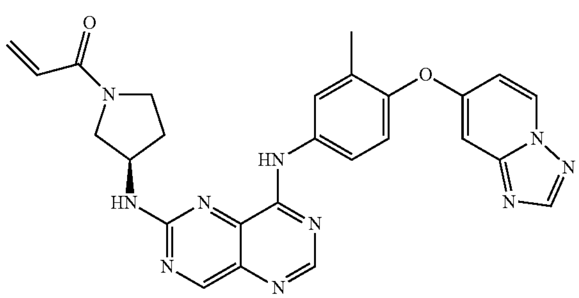 [SMILES: C=CC(=O)N1CC[C@@H](Nc2ncc3ncnc(Nc4ccc(Oc5ccn6ncnc6c5)c(C)c4)c3n2)C1] | 1.09 | 509 | 5 |

TABLE 8-continued

| Name | Structure | $t_{Ret}$ [min] | $[M + H]^+$ | Method |
|------|-----------|-----------------|-------------|--------|
| I-19 | 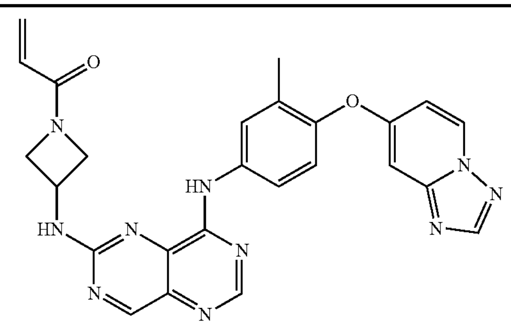 | 1.03 | 495 | 5 |

Biological Assays

Ba/F3 Cell Model Generation and Proliferation Assays

Ba/F3 cells were ordered from DSMZ (ACC300) and are grown in RPMI-1640 (ATCC 30-2001)+10% FBS+10 ng/ml IL-3 at 37° C. in 5% $CO_2$ atmosphere. Plasmids containing HER2 mutants and EGFR WT were obtained from GeneScript. To generate EGFR/HER2-dependent Ba/F3 models, Ba/F3 cells are transduced with retroviruses containing vectors that harbor EGFR WT, HER2 WT or HER2 mutants (YVMA). Platinum-E cells (Cell Biolabs) are used for retrovirus packaging. Retrovirus is added to Ba/F3 cells. To ensure infection, 4 µg/mL polybrene is added and cells are spin-infected. Infection efficiency is confirmed by measuring GFP-positive cells using a cell analyzer. Cells with an infection efficiency of 10% to 20% are further cultivated and puromycin selection with 1 µg/mL is initiated. As a control, parental Ba/F3 cells are used to assess the selection status. Selection is considered successful when parental Ba/F3 cells cultures die. To evaluate the transforming potential of HER2 mutations, the growth medium is no longer supplemented with IL-3. Ba/F3 cells harboring the empty vector are used as a control. A switch from IL-3 to EGF is performed for Ba/F3 cells expressing EGFR WT known for its dependency on EGF ligand. Approximately ten days before conducting the experiments, puromycin is left out. For proliferation assays (data in tables 10 and 12), Ba/F3 cells are seeded into 96-well plates at 5×10³ cells/100 µL in growth media. Compounds are added by using a HP D3000 Digital Dispenser. All treatments are performed in technical triplicates. Treated cells are incubated for 72 h at 37° C. with 5% $CO_2$. A CellTiter-Glo® Luminescent Cell Viability Assay (Promega) is performed and chemoluminescence is measured by using the multilabel Plate Reader VICTOR X4. The raw data are imported into and analyzed with the Boehringer Ingelheim proprietary software MegaLab (curve fitting based on the program PRISM, GraphPad Inc.).

pEGFR Assay

This assay quantifies the phosphorylation of EGFR at Tyr1068 and is used to measure the inhibitory effect of compounds on the transgenic EGFR wild type (WT) protein expressed in HEK cells.

Human HEK cells (ATCC CRL-1573) are grown in Minimum essential Medium Eagle, MEM Eagle EBSS, without L-Glutamine, with non essential amino acids and sodium pyruvate (EMEM Lonza BE12-662F)+5 ml GlutaMax (Gibco 35050-038; L-alanyl-L-glutamine)+5 ml Sodium Pyruvat (Gibco; 100 mM)+10% FBS at 37° C. in 5% $CO_2$ atmosphere and transduced with a retroviral vector encoding EGFR WT. Transduced cells are selected using puromycin. p-EGFR Tyr1068 is determined using the AlphaScreen Surefire pEGF Receptor (Tyr1068) Assay (PerkinElmer, TGRERS). For the assay, HEK EGFR WT cells are seeded in MEM medium with 10% FBS. 60 nL compound dilutions were added to each well of Greiner TC 384 plates using the Echo platform. Subsequently, 60.000 cells/well in 60 µL are added. Cells are incubated with compound for 4 h at 37° C. Following centrifugation and removal of the medium supernatant, 20 µL of 1.6-fold lysis buffer from TGR/Perkin Elmer kit with protease inhibitors is added. The mixture is incubated at a temperature of 20-25° C. with shaking (700 rpm) for 20 min. After centrifugation, 4 µL of the lysate are transferred to Proxiplates. 5 µL of Acceptor Mix (Activation Buffer diluted 1:25 in combined Reaction Buffer 1 and Reaction Buffer 2 (TGRERS Assay Kit, PerkinElmer) plus 1:50 of Protein A Acceptor Beads 6760137, Perkin Elmer) are added to each well. Plates are shaken for 1 min (1400 rpm) and incubated for 2 h at a temperature of (20-25° C.) in the dark. 3 µL of donor mix (AlphaScreen Streptavidin-coated Donor Beads (6760002, PerkinElmer) 1:50 diluted in Dilution Buffer (TGRERS Assay Kit, PerkinElmer)) are added to each well. Plates are shaken for 1 min (1400 rpm) and incubated for 2 h at a temperature of (20-25° C.) in the dark. Plates are subsequently analyzed using an Envision reader platform. Results are computed in the following way: The ratio of the value of the test compound and the value of the negative control (DMSO) is calculated. $IC_{50}$ values are computed from these values in the MEGASTAR $IC_{50}$ application using a 4 parametric logistic model.

This cellular phospho-EGFR (pEGFR) compound dose-response assay quantifies the phosphorylation of EGFR at Tyr1068 in HEK cells expressing EGFR WT. The results of the assay are provided as $IC_{50}$ values. The higher the pEGFR $IC_{50}$ values for a given compound, the higher the EGFR WT sparing activity.

pHER2 (ERBB2) YVMA Assay

This assay quantifies the phosphorylation of HER2 YVMA at Tyr1221/1222 and is used to measure the inhibitory effect of compounds on the transgenic HER2 YVMA protein expressed in HEK cells using a Doxycycline inducible expression system.

Human HEK cells are grown in Minimum essential Medium Eagle, MEM Eagle EBSS, without L-Glutamine, with non essential amino acids and sodium pyruvate (EMEM Lonza BE12-662F)+5 mL GlutaMax (Gibco 35050-038; L-alanyl-L-glutamine)+5 mL Sodium Pyruvat (Gibco; 100 mM)+10% FBS at 37° C. in 5% CO2 atmosphere and transduced with a retroviral vector encoding HER2 YVMA. Transduced cells are selected using puromycin. p-ERBB2 Tyr1221/1222 is determined using the AlphaScreen Surefire ErbB2 (Tyr1221/1222) Assay (PerkinElmer, TGREB2S). For the assay, HEK HER2 YVMA cells are seeded in MEM medium with 10% FBS. 4 hours prior to compound addition, HER2 YVMA expression is induced using 1 µg/mL Doxycycline. 60 nL compound dilutions are added to each well of Greiner TC 384 plates using the Echo platform. Subsequently, 60.000 cells/well in 60 µL are added. Cells are incubated with compound for 4 h at 37° C. Following centrifugation and removal of the medium supernatant, 20 µL of 1.6-fold lysis buffer from TGR/Perkin Elmer kit with protease inhibitors are added. The mixture is incubated at a temperature of 20-25° C. with shaking (700 rpm) for 20 min. After centrifugation, 4 µL of the lysate are transferred to Proxiplates. 5 µL of Acceptor Mix (Activation Buffer diluted 1:25 in combined Reaction Buffer 1 and Reaction Buffer 2 (TGREB2S Assay Kit, PerkinElmer) plus 1:50 of Protein A Acceptor Beads 6760137, PerkinElmer) are added to each well. Plates are shaken for 1 min (1400 rpm) and incubated for 2 h at a temperature of 20-25° C. in the dark. 3 µL of donor mix (AlphaScreen Streptavidin-coated Donor Beads (6760002, PerkinElmer) 1:50 diluted in Dilution Buffer (TGRERS Assay Kit, PerkinElmer)) are added to each well. Plates are shaken for 1 min (1400 rpm) and incubated for 2 h at a temperature of 20-25° C. in the dark. Plates are subsequently analyzed using an Envision reader platform. Results are computed in the following way: The ratio of the value of the test compound and the value of the negative control (DMSO) is calculated. $IC_{50}$ values are computed from these values in the MEGASTAR $IC_{50}$ application using a 4 parametric logistic model. This cellular phospho-HER2 YVMA (pHER2 YVMA) compound dose-response assay quantifies the phosphorylation of HER2 YVMA at Tyr1221/1222 in HEK cells expressing HER2 YVMA. The results of the assay are provided as $IC_{50}$ values. The lower the reported pHER2 YVMA $IC_{50}$ values for a given compound, the stronger the inhibitory effect of a compound on HER2 YVMA kinase activity.

HER2 YVMA Tumor Cell Line Model Generation and Proliferation Assays

HER2 WT-dependent NCI-H2170 cells were ordered from (ATCC, CRL-5928) and are grown in RPMI-1640 (Gibco #A10491) ATCC-Formulation+10% FCS at 37° C. in 5% CO2 atmosphere. Homology-directed genome engineering is employed to insert a 12 nucleotide sequence encoding YVMA into Exon 20 of the genomic HER2 locus in NCI-H2170 cells. This results in the change from HER2 WT to the HER2 YVMA variant representing HER2 p.A775_G776insYVMA. The DNA template containing the HER2 exon 20 YVMA insertion variant was obtained from GenScript. PCR followed by Sanger sequencing is used to confirm the presence of the 12-nucleotide insertion in HER2 Exon 20 resulting in the YVMA amino acid duplication.

For proliferation assays, NCI-H2170 (HER2 wild type), NCI-H2170 HER2 YVMA and EGFR WT dependent A431 cells are used. NCI-H2170 HER2 YVMA or NCI-H2170 cells are seeded into 96-well plates at 750 cells/60 µL in growth media (RPMI ATCC+10% FCS, +Penicillin/Streptomycin). A431 cells (ATCC CRL-1555) (DMEM (Sigma #D6429)+5 mL Sodium Pyruvat Gibco 11360-039) are plated at a density of 5000 cells per well (200 µL) in a 96-well plate. Compounds are added by using a HP D3000 Digital Dispenser one day after plating the cells. All treatments are performed in technical triplicates. Treated cells are incubated for 72 h at 37° C. with 5% CO2. CellTiter-Glo® Luminescent Cell Viability Assay (Promega) is performed and chemoluminescence is measured by using the multilabel Plate Reader VICTOR X4. The raw data are imported into and analyzed with the Boehringer Ingelheim proprietary software MegaLab (curve fitting based on the program PRISM, GraphPad Inc.).

TABLE 9

Biomarker Assay

| Name | IC50 HEK pHER2 YVMA [nM] | IC50 HEK pEGFR [nM] |
|---|---|---|
| I-01 | 13 | 579 |
| I-02 | 34 | 628 |
| I-03 | 20 | 916 |
| I-04 | 26 | 495 |
| I-05 | 10 | 315 |
| I-06 | 44 | 773 |
| I-07 | 20 | 1170 |
| I-08 | 58 | 336 |
| I-09 | 26 | 715 |
| I-10 | 24 | 217 |
| I-11 | 22 | 521 |
| I-12 | 16 | 230 |
| I-13 | 28 | 429 |
| I-14 | 11 | 73 |
| I-15 | 12 | 86 |
| I-16 | 5 | 23 |
| I-17 | 2 | 94 |
| I-18 | 4 | 137 |
| I-19 | 8 | 41 |

TABLE 10

Proliferation Assays

| Name | GI50 NCI H-2170 HER2 wt amp. [nM] | GI50 NCI H-2170 HER2 YVMA [nM] | GI50 A431 EGFR wt amp. [nM] | GI50 BAF3 HER2 WT [nM] | GI50 BAF3 HER2 YVMA [nM] | GI50 BAF3 EGF dep. [nM] |
|---|---|---|---|---|---|---|
| I-01 | 6 | 33 | >5000 | 1 | 16 | 1540 |
| I-02 | 13 | 228 | >5000 | 1 | 37 | 3010 |
| I-03 | 11 | 139 | >5000 | 2 | 38 | >5000 |
| I-04 | 12 | 99 | >5000 | 3 | 32 | >5000 |
| I-05 | 8 | 55 | >5000 | 1 | 21 | 1880 |
| I-06 | 12 | 215 | >5000 | 1 | 31 | >5000 |
| I-07 | 17 | 73 | >5000 | 3 | 42 | 1500 |
| I-08 | 8 | 44 | 1500 | 2 | 36 | 2300 |
| I-09 | 9 | 75 | >5000 | 1 | 29 | 2240 |
| I-10 | 12 | 126 | 1460 | 3 | 35 | 1650 |
| I-11 | 8 | 172 | 1250 | 2 | 28 | >2000 |
| I-12 | 8 | 71 | >5000 | 2 | 18 | 1750 |
| I-13 | 19 | 82 | >5000 | 1 | 32 | >2000 |
| I-14 | 10 | 37 | >2000 | 2 | 17 | 756 |
| I-15 | 13 | 44 | 948 | 2 | 18 | 425 |
| I-16 | 4 | 19 | 660 | 1 | 10 | 375 |
| I-17 | 9 | 39 | >2000 | 2 | 14 | 1100 |
| I-18 | 10 | 87 | >2000 |  | 29 | 3270 |
| I-19 | 8 | 34 | 752 | 2 | 11 | 206 |

TABLE 11
Biomarker Assay
| Name | Structure | IC50 HEK pHER2 YVMA [nM] | IC50 HEK pEGFR [nM] |
|---|---|---|---|
| Allitinib | 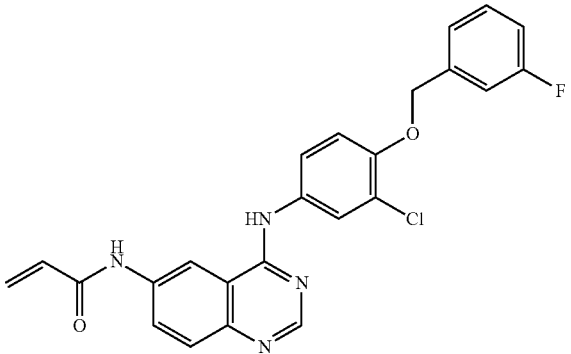 [SMILES: C=CC(=O)Nc1ccc2ncnc(Nc3ccc(OCc4cccc(F)c4)c(Cl)c3)c2c1] | 3 | 1 |
| Ibrutinib | 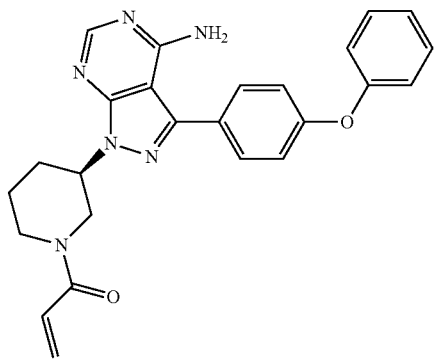 [SMILES: C=CC(=O)N1CCC[C@@H](n2nc(-c3ccc(Oc4ccccc4)cc3)c3c(N)ncnc32)C1] | 26 | 21 |
| Neratinib | 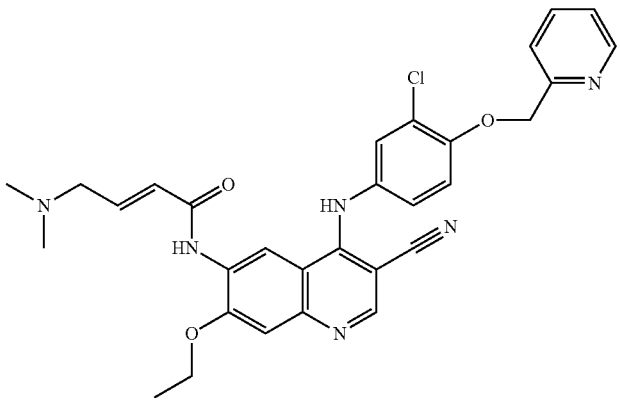 [SMILES: CCOc1cc2ncc(C#N)c(Nc3ccc(OCc4ccccn4)c(Cl)c3)c2cc1NC(=O)/C=C/CN(C)C] | 1 | 4 |
| Allitinib | 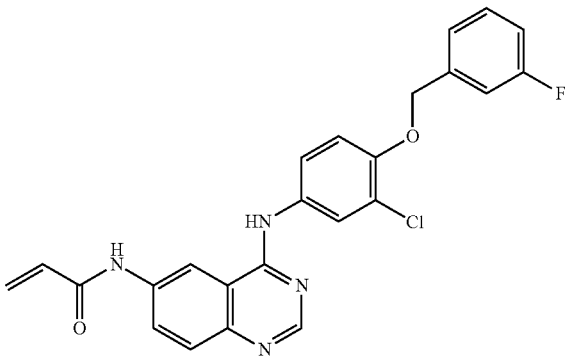 [SMILES: C=CC(=O)Nc1ccc2ncnc(Nc3ccc(OCc4cccc(F)c4)c(Cl)c3)c2c1] | 3 | 1 |

TABLE 11-continued

| | Biomarker Assay | | |
|---|---|---|---|
| Name | Structure | IC50 HEK pHER2 YVMA [nM] | IC50 HEK pEGFR [nM] |
| Poziotinib | | 5 | 1 |
| WO 2019/046775 Comp. 2 | | 11 | 7 |
| Allitinib | | 3 | 1 |
| Tucatinib | | 4 | 1410 |

TABLE 11-continued

Biomarker Assay

| Name | Structure | IC50 HEK pHER2 YVMA [nM] | IC50 HEK pEGFR [nM] |
|---|---|---|---|
| WO 2007/059257 Ex. 185 | 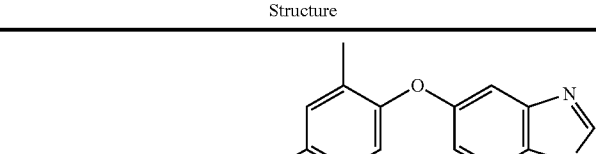 | 33 | 317 |

TABLE 12

Tumour Cell Proliferation Assay

| Name | GI50 NCI H-2170 HER2 wt amp. [nM] | GI50 NCI H-2170 HER2 YVMA [nM] | GI50 A431 EGFR wt amp. [nM] | GI50 BAF3 HER2 WT [nM] | GI50 BAF3 HER2 YVMA [nM] | GI50 BAF3 EGF dep. [nM] |
|---|---|---|---|---|---|---|
| allitinib | 36 | 203 | 403 | | 17 | 31 |
| ibrutinib | 16 | 132 | 199 | | 44 | 70 |
| neratinib | 3 | 37 | 55 | 1 | 5 | 14 |
| poziotinib | 1 | 5 | 1 | 1 | 2 | 1 |
| WO 2019/046775 Comp. 2 | 22 | 34 | 16 | 3 | 14 | 13 |
| tucatinib | 58 | 798 | 4220 | 10 | 338 | 2970 |
| WO 2007/059257 Ex. 185 | 108 | 926 | >5000 | | 60 | 1190 |

Example of Pharmaceutical Formulation

| Ingredient | Amount |
|---|---|
| Active substance | 100 mg |
| lactose | 140 mg |
| corn starch | 240 mg |
| polyvinylpyrrolidone | 15 mg |
| magnesium stearate | 5 mg |

The active substance is grounded and mixed together with lactose and some of the corn starch. The mixture is sieved, then wet granulated with polyvinylpyrrolidone solution. The granules, the remaining corn starch and the magnesium stearate are mixed together. The mixture is compressed to produce tablets of suitable shape and size.

In Claim 10, at Column 100, Lines 38-47, the chemical structure shown as:
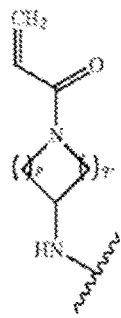
Should be replaced with the corrected chemical structure below:
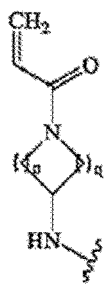
In Claim 16, at Column 104, Lines 56-65, the chemical structure I-01 shown as:
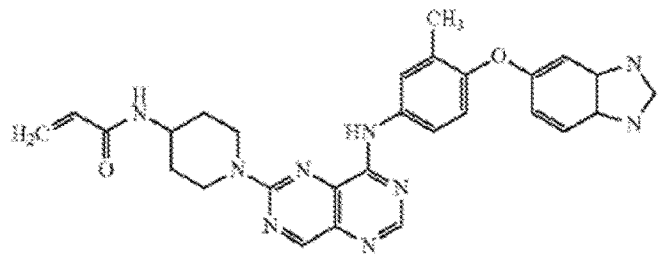
Should be replaced with the corrected chemical structure I-01 below:
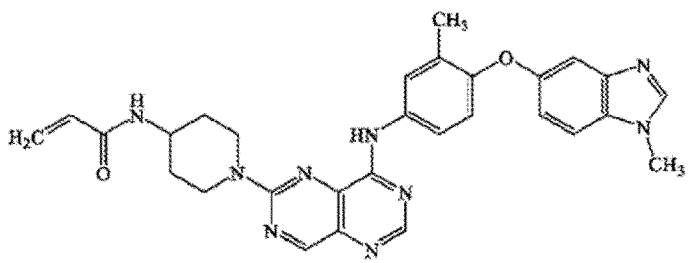
In Claim 18, at Column 105, Lines 20-30, the chemical structure I-03 shown as:
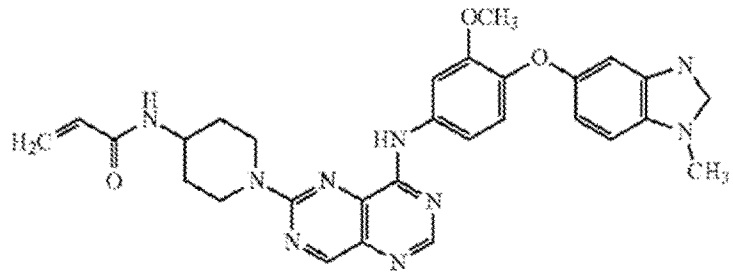

Should be replaced with the corrected chemical structure I-03 below:
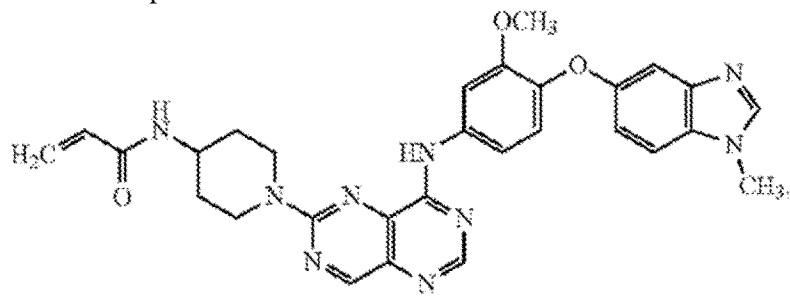
In Claim 20, at Column 105, Lines 55-65, the chemical structure I-04 shown as:
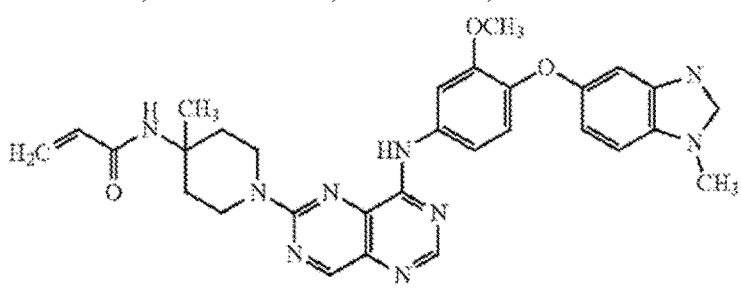
Should be replaced with the corrected chemical structure I-04 below:
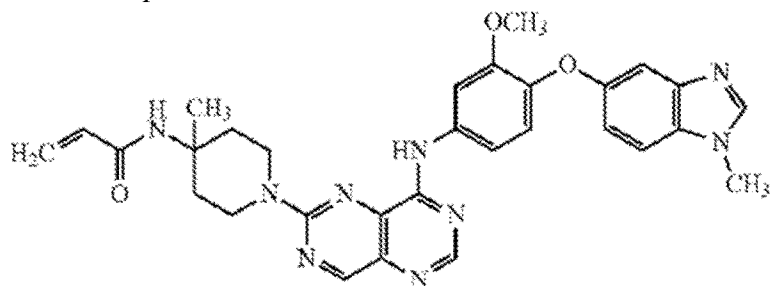
In Claim 22, at Column 106, Lines 20-30, the chemical structure I-05 shown as:
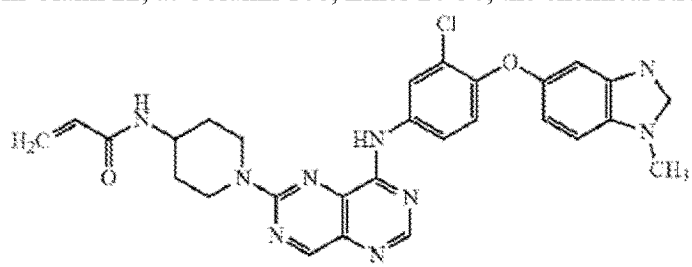
Should be replaced with the corrected chemical structure I-05 below:
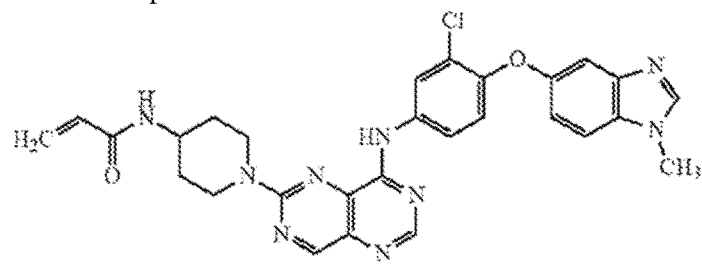

In Claim 23, at Column 106, Lines 40-50, the chemical structure I-07 shown as:
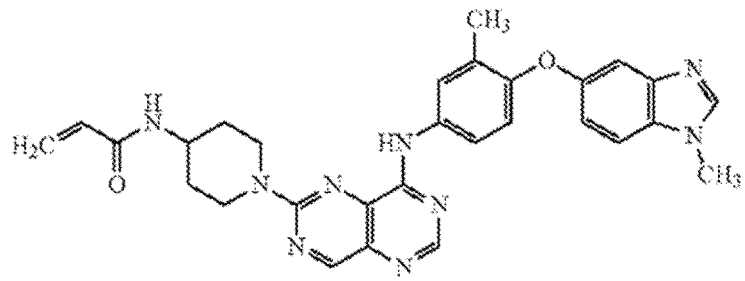
Should be replaced with the corrected chemical structure I-07 below:
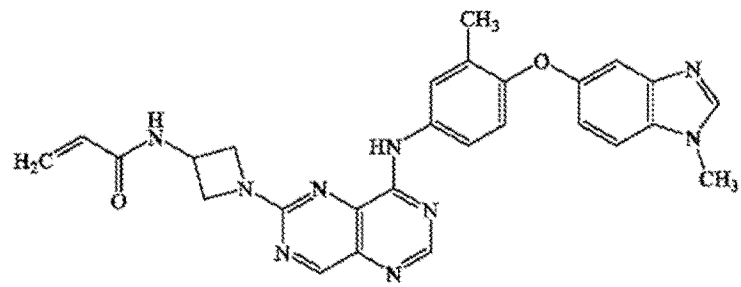
In Claim 24, at Column 106, Lines 55-65, the chemical structure I-07 shown as:
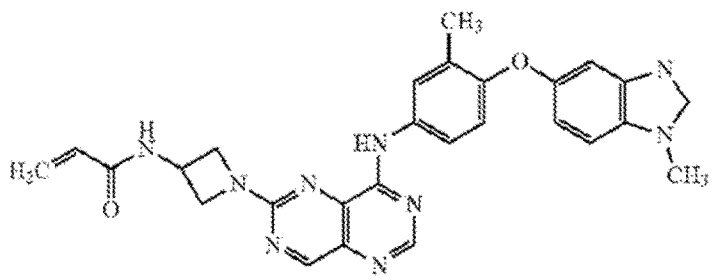
Should be replaced with the corrected chemical structure I-07 below:
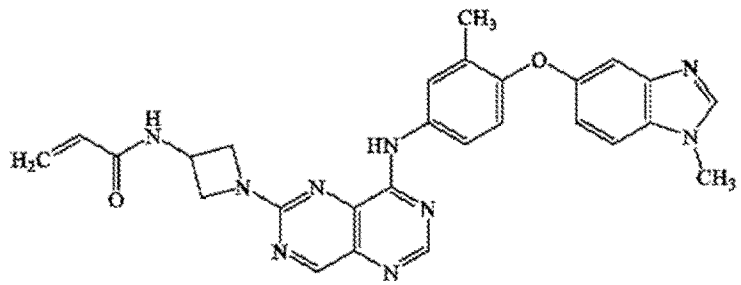

In Claim 26, at Column 107, Lines 20-30, the chemical structure I-09 shown as:
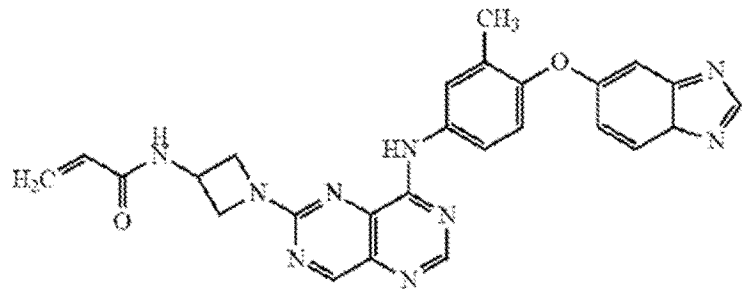
Should be replaced with the corrected chemical structure I-09 below:
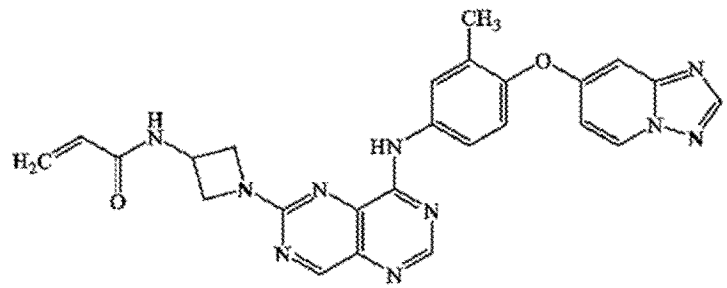
In Claim 28, at Column 107, Lines 55-65, the chemical structure I-13 shown as:
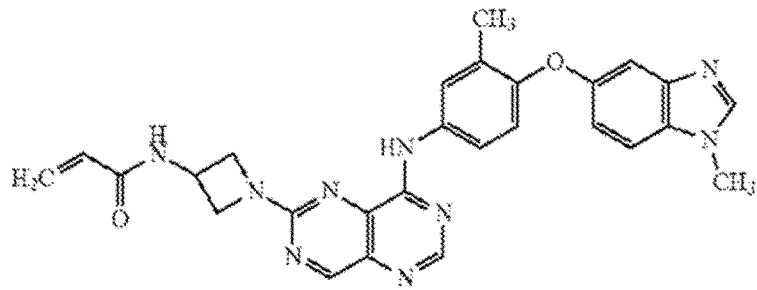
Should be replaced with the corrected chemical structure I-13 below:
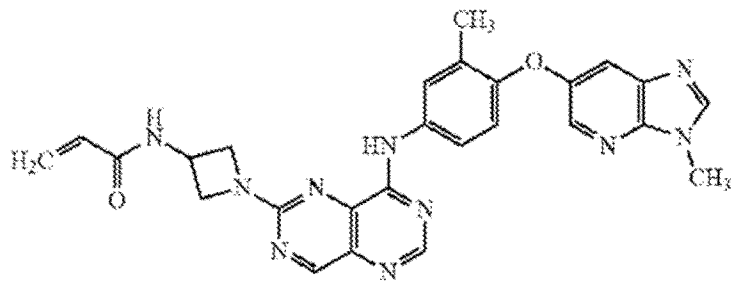

In Claim 29, at Column 108, Lines 5-15, the chemical structure I-14 shown as:
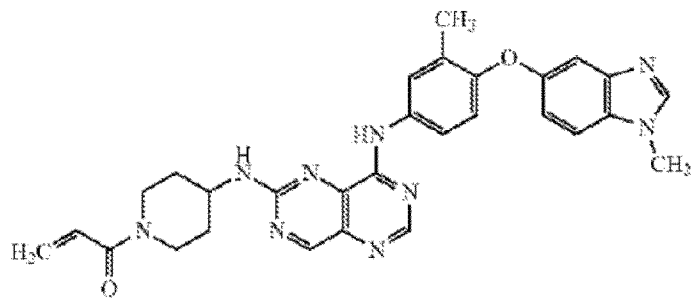
Should be replaced with the corrected chemical structure I-14 below:
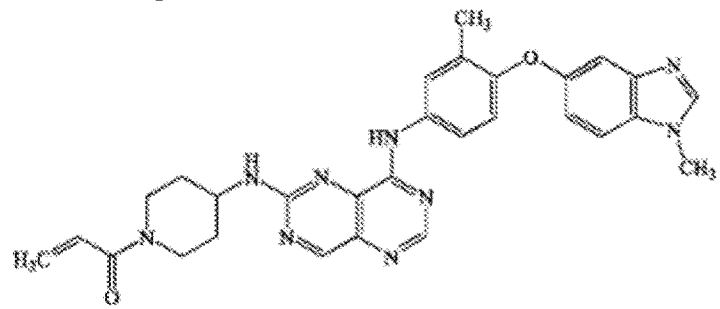

The invention claimed is:
1. A compound of Formula (I):

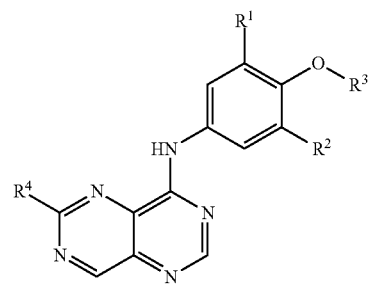

(I)

or a pharmaceutically acceptable salt or stereoisomer thereof,
wherein:
$R^1$ H, halogen, $CH_3$, C≡CH, or $OCH_3$;
$R^2$ is H or halogen;
$R^3$ is formula (i.1), formula (i.2), formula (i.3), or formula (i.4):

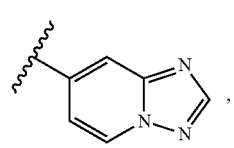

(i.1)

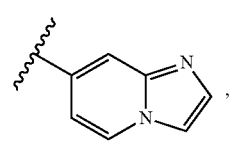

(i.2)

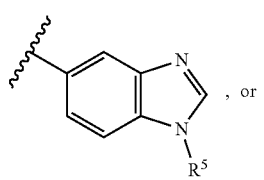

(i.3)

-continued

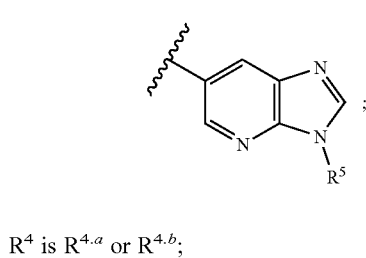
(i.4)

R⁴ is R⁴·ᵃ or R⁴·ᵇ;

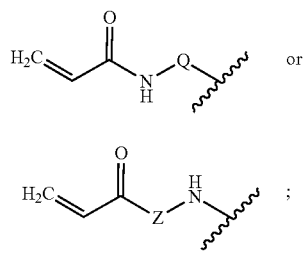
Rᵃ or

Rᵇ

Q is a 4- to 6-membered heterocyclyl, wherein the 4- to 6-membered heterocyclyl contains one nitrogen heteroatom, and further wherein one carbon atom of the 4- to 6-membered heterocyclyl is optionally substituted with $CH_3$;

Z is a 4- to 6-membered heterocyclyl, wherein the 4- to 6-membered heterocyclyl contains one nitrogen heteroatom, and further wherein one carbon atom of the 4- to 6-membered heterocyclyl is optionally substituted with $CH_3$; and $R^5$ is H or $CH_3$;

with the proviso that at least one of $R^1$ and $R^2$ is not H.

2. The compound according to claim 1, or a pharmaceutically acceptable salt or stereoisomer thereof, wherein $R^1$ is halogen, $CH_3$, C≡CH, or $OCH_3$.

3. The compound according to claim 1, or a pharmaceutically acceptable salt or stereoisomer thereof, wherein $R^1$ is F.

4. A The compound according to claim 1, or a pharmaceutically acceptable salt or stereoisomer thereof, wherein $R^1$ is Cl.

5. The compound according to claim 1, or a pharmaceutically acceptable salt or stereoisomer thereof, wherein $R^1$ is $CH_3$.

6. A The compound according to claim 1, or a pharmaceutically acceptable salt or stereoisomer thereof, wherein $R^1$ is C≡CH.

7. A The compound according to claim 1, or a pharmaceutically acceptable salt or stereoisomer thereof, wherein $R^1$ is $OCH_3$.

8. A The compound according to claim 1, or a pharmaceutically acceptable salt or stereoisomer thereof, wherein $R^2$ is H.

9. A The compound according to claim 1, or a pharmaceutically acceptable salt or stereoisomer thereof, wherein $R^2$ is Cl.

10. A The compound according to claim 1, or a pharmaceutically acceptable salt or stereoisomer thereof, wherein $R^4$ is $R^{4.a}$ or $R^{4.b}$:

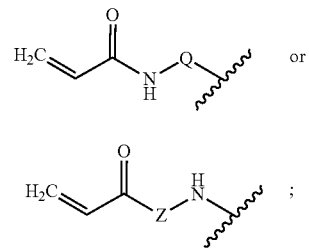
Rᵃ or

Rᵇ wherein:
$R^{4.a}$ is $R^{4.a.1}$

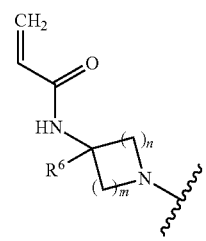
$R^{4.a.1}$ wherein:
$R^6$ is H or $CH_3$;
m is 1 or 2; and
n is 1 or 2;
and
$R^{4.b}$ is $R^{4.b.1}$:

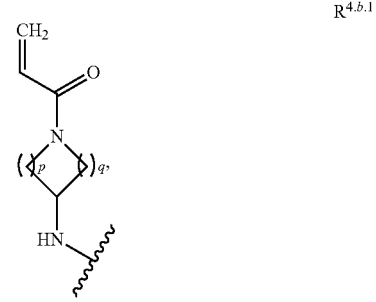
$R^{4.b.1}$ wherein:
p is 1 or 2; and
q is 1 or 2.

11. The compound according to claim 1, or a stereoisomer thereof, wherein the compound, or stereoisomer thereof, is selected from the group consisting of:

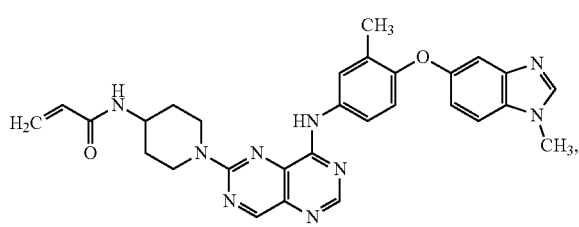
I-01

-continued
I-02
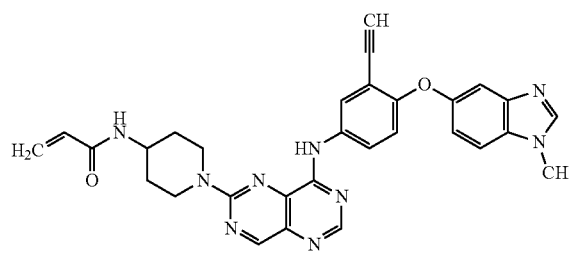
I-03
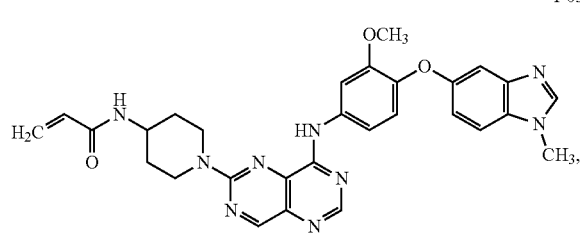
I-04
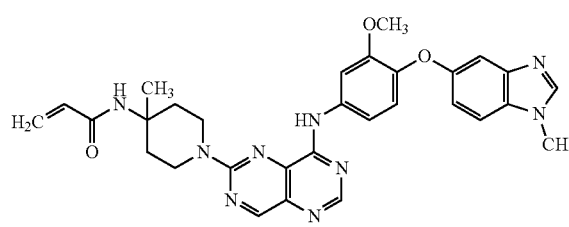
I-05
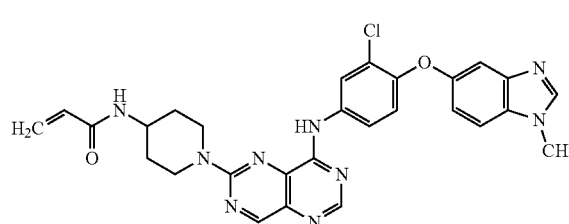
I-06
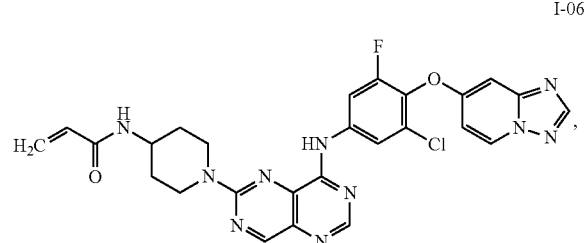
I-07
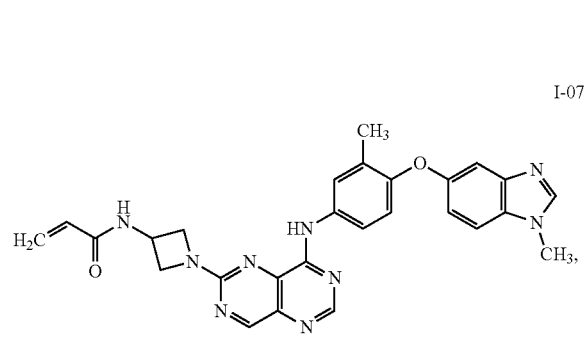
-continued
I-08
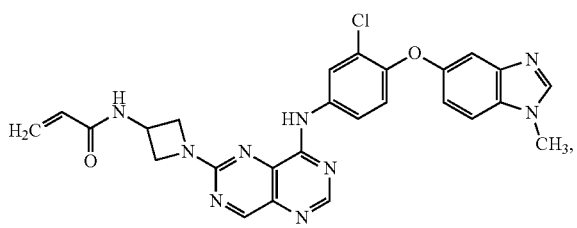
I-09
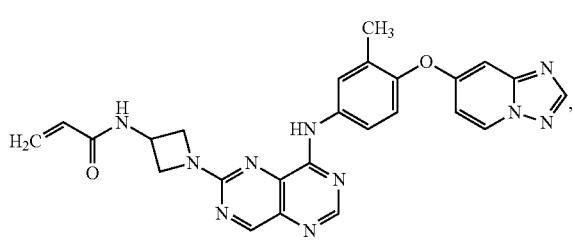
I-10
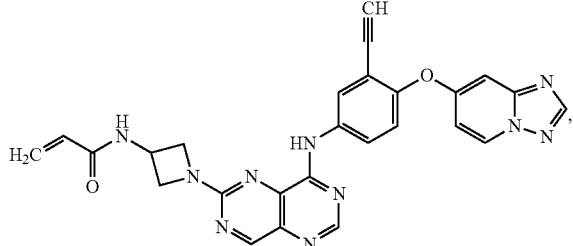
I-11
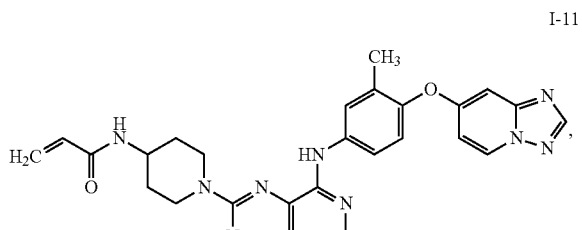
I-12
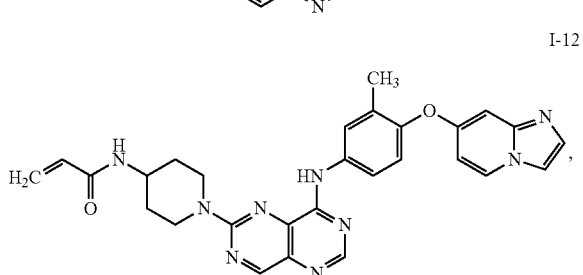
I-13
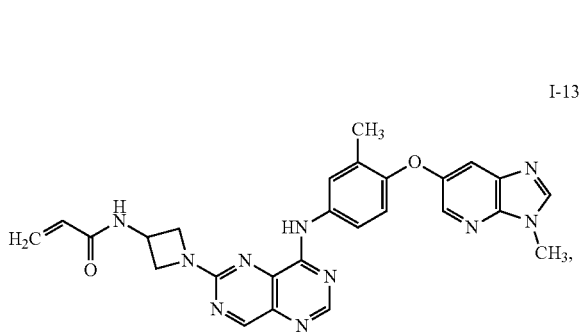

-continued

I-14
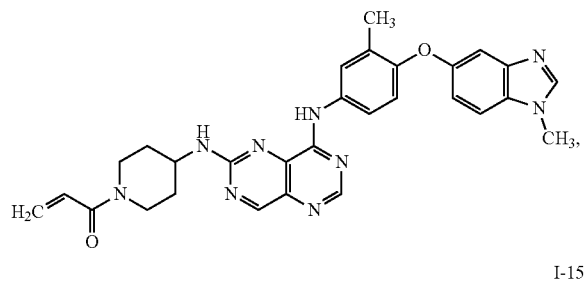

I-15
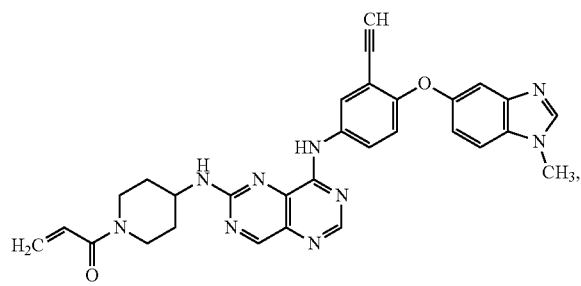

I-16
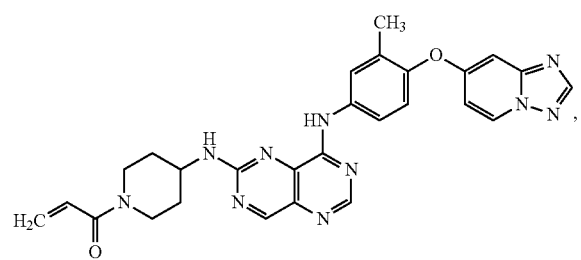

I-17
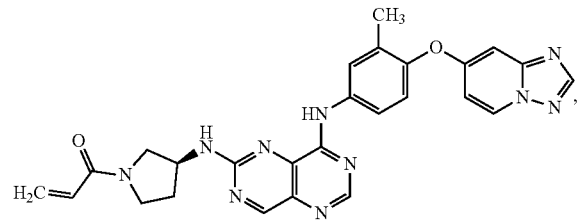

I-18
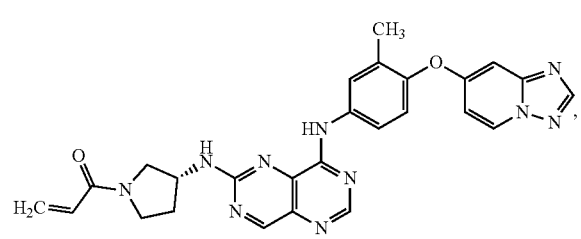

-continued
and

I-19
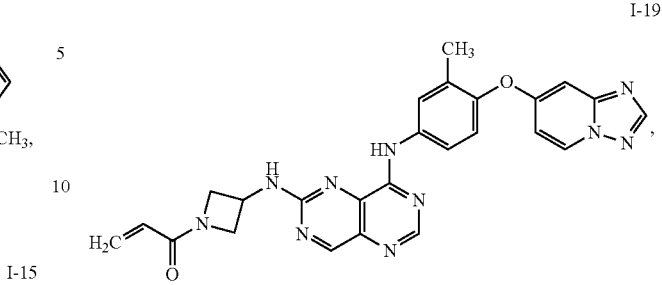

or a pharmaceutically acceptable salt thereof.

12. A pharmaceutical composition comprising one or more pharmaceutically acceptable excipients and a therapeutically effective amount of a compound according to claim 1, or a pharmaceutically acceptable salt or stereoisomer thereof.

13. A pharmaceutical composition comprising a therapeutically effective amount of a compound according to claim 1, or a pharmaceutically acceptable salt or stereoisomer thereof, and a pharmaceutically active substance selected from the group consisting of a cytostatic active substance and a cytotoxic active substance.

14. A method for treating cancer in a patient, wherein the method comprises administering to the patient in need thereof a therapeutically effective amount of a compound according to claim 1, or a pharmaceutically acceptable salt or stereoisomer thereof; wherein the cancer is selected from the group consisting of biliary cancer, bladder cancer, brain cancer, breast cancer, cervical cancer, colorectal cancer, endometrial cancer, an esophagus tumor, a gallbladder tumor, gastrointestinal cancer, a head and neck tumor, kidney cancer, liver cancer, lung cancer, prostate cancer, and skin cancer.

15. A compound having the following structure:

I-01
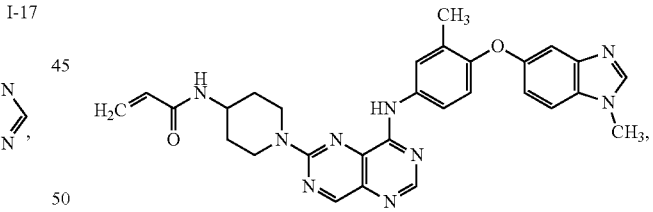

or a pharmaceutically acceptable salt thereof.

16. A compound having the following structure:

I-01
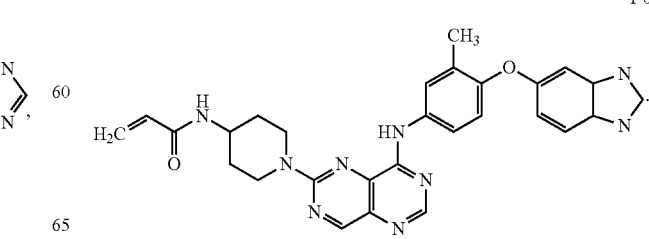

17. A compound having the following structure:

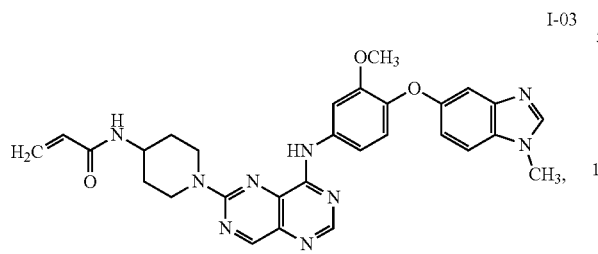

I-03 or a pharmaceutically acceptable salt thereof.

18. A compound having the following structure:

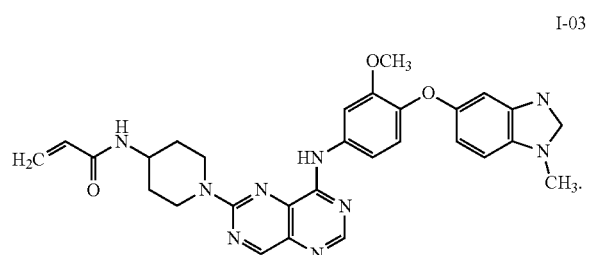

I-03

19. A compound having the following structure:

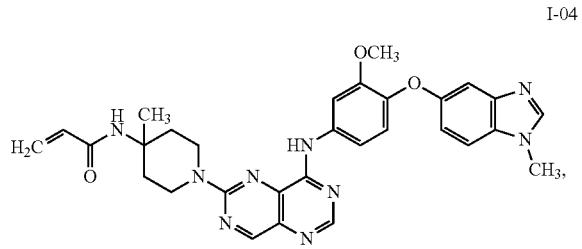 [SMILES: C=CC(=O)NC1(C)CCN(c2ncc3ncnc(Nc4ccc(Oc5ccc6c(c5)ncn6C)c(OC)c4)c3n2)CC1]

I-04 or a pharmaceutically acceptable salt thereof.

20. A compound having the following structure:

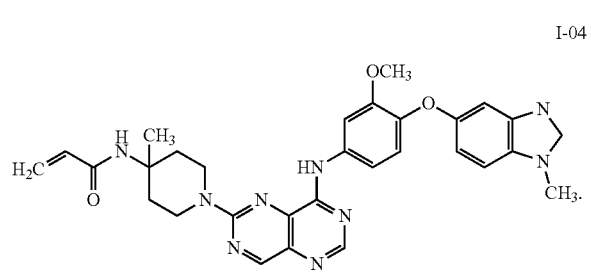 [SMILES: C=CC(=O)NC1(C)CCN(c2ncc3ncnc(Nc4ccc(Oc5ccc6c(c5)NCN6C)c(OC)c4)c3n2)CC1]

I-04

21. A compound having the following structure:

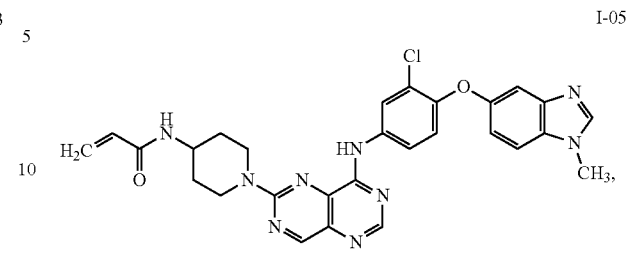

I-05 or a pharmaceutically acceptable salt thereof.

22. A compound having the following structure:

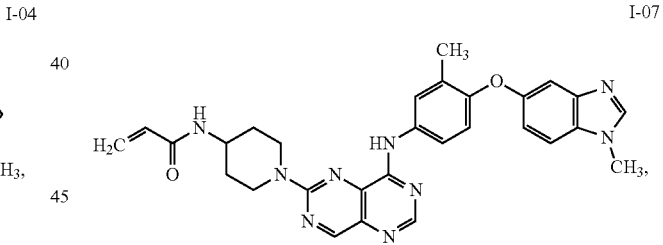

I-05

23. A compound having the following structure:

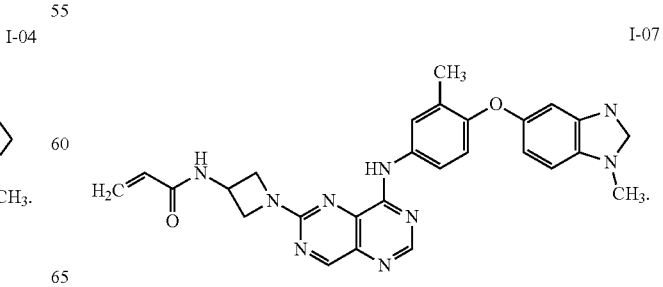

I-07 or a pharmaceutically acceptable salt thereof.

24. A compound having the following structure:

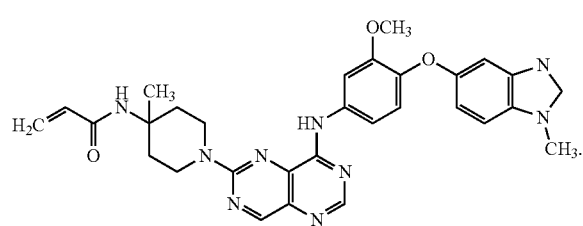

I-07

25. A compound having the following structure:

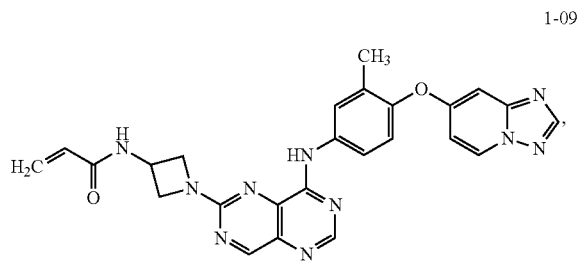 [SMILES: C=CC(=O)NC1CN(c2ncc3ncnc(Nc4ccc(Oc5ccn6ncnc6c5)c(C)c4)c3n2)C1]

I-09 or a pharmaceutically acceptable salt thereof.

26. A compound having the following structure:

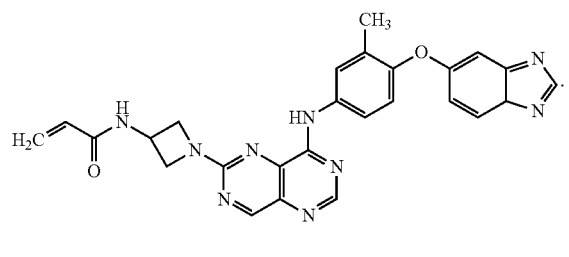

I-09

27. A compound having the following structure:

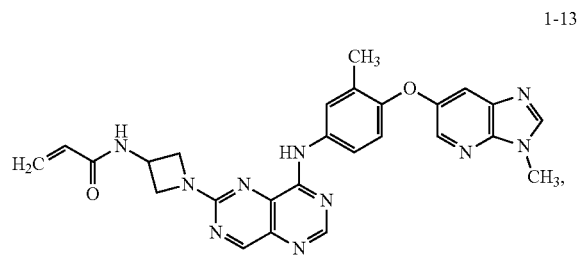 [SMILES: C=CC(=O)NC1CN(c2ncc3ncnc(Nc4ccc(Oc5cnc6c(c5)ncn6C)c(C)c4)c3n2)C1]

I-13 or a pharmaceutically acceptable salt thereof.

28. A compound having the following structure:

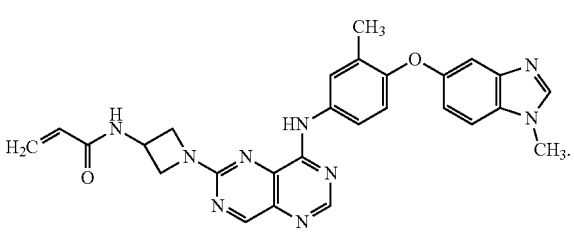

I-13

29. A compound having the following structure:

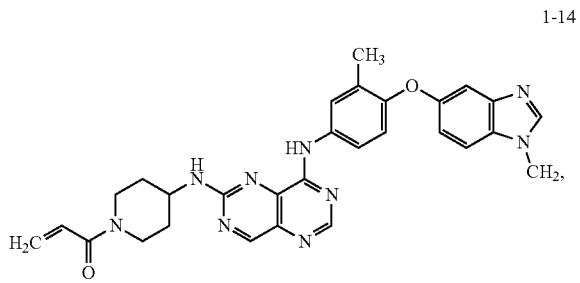

I-14 or a pharmaceutically acceptable salt thereof.

30. A compound having the following structure:

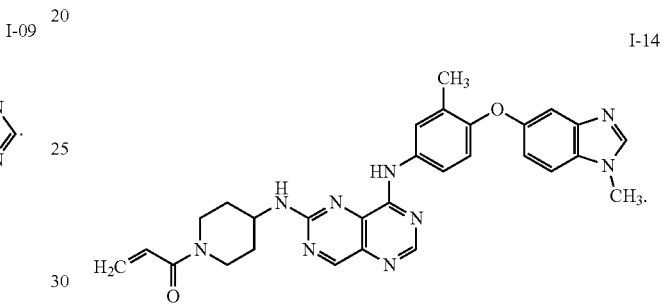

I-14

31. A compound having the following structure:

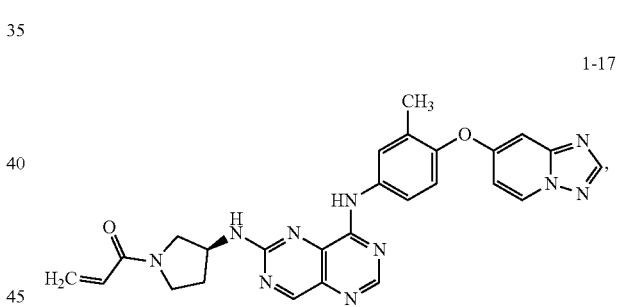

I-17 or a pharmaceutically acceptable salt thereof.

32. A compound having the following structure:

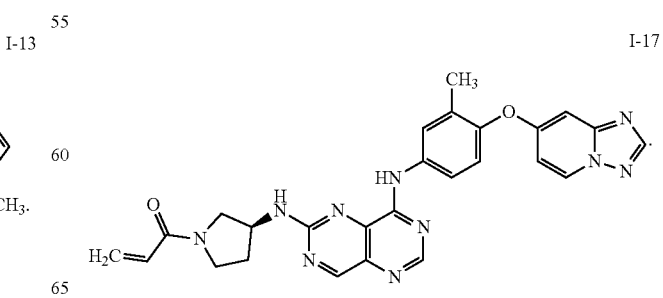

I-17

33. A compound having the following structure:
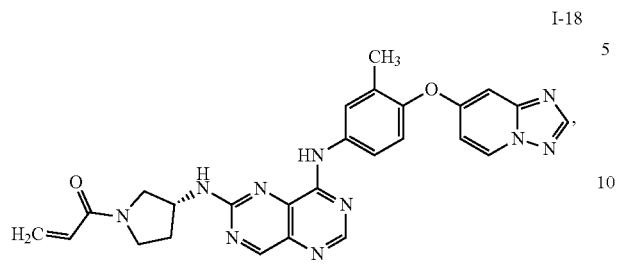
I-18
or a pharmaceutically acceptable salt thereof.
34. A compound having the following structure:
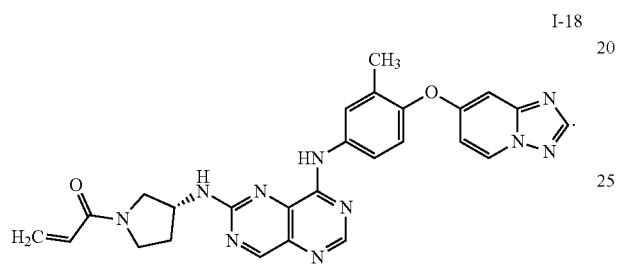
I-18
* * * * *

UNITED STATES PATENT AND TRADEMARK OFFICE
CERTIFICATE OF CORRECTION

PATENT NO. : 11,608,343 B2
APPLICATION NO. : 17/223132
DATED : March 21, 2023
INVENTOR(S) : Birgit Wilding et al.

It is certified that error appears in the above-identified patent and that said Letters Patent is hereby corrected as shown below:

In the Claims

In Claim 1, at Column 98, Line 42, the text "$R^1$ H, halogen, $CH_3$, C≡CH, or $OCH_3$;" should be replaced with the text, "$R^1$ is H, halogen, $CH_3$, C≡CH, or $OCH_3$;".

In Claim 1, at Column 99, Line 14, the text "$R^{.a}$" should be replaced with the text, "$R^{4.a}$".

In Claim 1, at Column 99, Line 19, the text "$R^{.b}$" should be replaced with "$R^{4.b}$".

In Claim 4, at Column 99, Line 45, the text "A The compound according to claim 1," should be replaced with the text, "The compound according to claim 1,".

In Claim 6, at Column 99, Line 52, the text "A The compound according to claim 1," should be replaced with the text, "The compound according to claim 1,".

In Claim 7, at Column 99, Line 55, the text "A The compound according to claim 1," should be replaced with the text, "The compound according to claim 1,".

In Claim 8, at Column 99, Line 58, the text "A The compound according to claim 1," should be replaced with "The compound according to claim 1,".

In Claim 9, at Column 99, Line 62, the text "A The compound according to claim 1," should be replaced with "The compound according to claim 1,".

In Claim 10, at Column 99, Line 65, the text "A The compound according to claim 1," should be replaced with "The compound according to claim 1,".

In Claim 10, at Column 100, Line 2, the text "$R^{.a}$" should be replaced with "$R^{4.a}$".

In Claim 10, at Column 100, Line 8, the text "$R^{.b}$" should be replaced with "$R^{4.b}$".

Signed and Sealed this
Eighteenth Day of July, 2023

Katherine Kelly Vidal
*Director of the United States Patent and Trademark Office*